(12) United States Patent
Bretschneider et al.

(10) Patent No.: US 7,947,704 B2
(45) Date of Patent: May 24, 2011

(54) 2,4,6-PHENYL-SUBSTITUTED CYCLIC KETOENOLS

(75) Inventors: Thomas Bretschneider, Lohmar (DE); Reiner Fischer, Monheim (DE); Oliver Gaertzen, Köln (DE); Klaus Kunz, Düsseldorf (DE); Stefan Lehr, Liederbach (DE); Dieter Feucht, Eschborn (DE); Peter Lösel, Leverkusen (DE); Olga Malsam, Rösrath (DE); Guido Bojack, Wiesbaden (DE); Christian Arnold, Langenfeld (DE); Thomas Auler, Leichlingen (DE); Martin Jeffrey Hills, Idstein (DE); Heinz Kehne, Hofheim (DE); Chris Rosinger, Hofheim (DE)

(73) Assignee: Bayer CropScience AG, Monheim (DE)

( * ) Notice: Subject to any disclaimer, the term of this patent is extended or adjusted under 35 U.S.C. 154(b) by 707 days.

(21) Appl. No.: 10/594,251

(22) PCT Filed: Mar. 11, 2005

(86) PCT No.: PCT/EP2005/002605
§ 371 (c)(1),
(2), (4) Date: Sep. 10, 2007

(87) PCT Pub. No.: WO2005/092897
PCT Pub. Date: Oct. 6, 2005

(65) Prior Publication Data
US 2007/0298968 A1    Dec. 27, 2007

(30) Foreign Application Priority Data
Mar. 25, 2004 (DE) .......................... 10 2004 014 620

(51) Int. Cl.
C07D 207/38 (2006.01)
A01N 43/36 (2006.01)

(52) U.S. Cl. ........ 514/294; 514/299; 514/409; 514/411; 514/413; 514/423; 548/112; 548/428; 548/408; 548/413; 548/513; 548/544; 546/94; 546/183

(58) Field of Classification Search .................. 548/112, 548/428, 408, 413, 513, 544; 546/94, 183; 514/294, 299, 409, 411, 413, 423
See application file for complete search history.

(56) References Cited

U.S. PATENT DOCUMENTS

| 3,542,809 A | 11/1970 | Nakanishi |
| 4,021,224 A | 5/1977 | Pallos et al. |
| 4,091,006 A | 5/1978 | Durden, Jr. et al. |
| 4,175,135 A | 11/1979 | Haines |
| 4,186,130 A | 1/1980 | Teach |
| 4,209,432 A | 6/1980 | Roth |
| 4,209,532 A | 6/1980 | Wheeler |
| 4,256,657 A | 3/1981 | Wheeler |
| 4,256,658 A | 3/1981 | Wheeler |
| 4,256,659 A | 3/1981 | Wheeler |
| 4,257,858 A | 3/1981 | Wheeler |
| 4,283,348 A | 8/1981 | Wheeler |
| 4,303,669 A | 12/1981 | D'Silva |
| 4,338,122 A | 7/1982 | Wheeler |
| 4,351,666 A | 9/1982 | Koerwer |
| 4,409,153 A | 10/1983 | Hodakowski |
| 4,436,666 A | 3/1984 | Wheeler |
| 4,526,723 A | 7/1985 | Wheeler et al. |
| 4,551,547 A | 11/1985 | Wheeler |
| 4,613,617 A | 9/1986 | Sousa |
| 4,623,727 A | 11/1986 | Hübele |
| 4,632,698 A | 12/1986 | Wheeler |
| 4,639,266 A | 1/1987 | Heubach et al. |
| 4,659,372 A | 4/1987 | Wheeler |
| 4,881,966 A | 11/1989 | Nyffeler et al. |
| 4,891,057 A | 1/1990 | Sohn et al. |
| 4,902,340 A | 2/1990 | Hubele |
| 4,925,868 A | 5/1990 | Terao et al. |
| 4,985,063 A | 1/1991 | Fischer et al. |
| 5,045,560 A | 9/1991 | Fischer et al. |
| 5,094,681 A | 3/1992 | Krämer et al. |
| 5,116,836 A | 5/1992 | Fischer et al. |
| 5,225,434 A | 7/1993 | Bertram et al. |
| 5,258,527 A | 11/1993 | Krauskopf et al. |
| 5,262,383 A | 11/1993 | Fischer et al. |

(Continued)

FOREIGN PATENT DOCUMENTS

| CA | 2 382 432 A1 | 3/2001 |
| CA | 2 492 096 A1 | 1/2004 |
| CA | 2 497 074 A1 | 3/2004 |

(Continued)

OTHER PUBLICATIONS

Clive, D.L. and Wang, J., "Synthesis of natural (−)-hamigeran B," *Tetrahedron Lett.* 44:7731-7733, Elsevier Ltd. (Oct. 2003).

(Continued)

*Primary Examiner* — Kahsay T Habte
(74) *Attorney, Agent, or Firm* — Sterne, Kessler, Goldstein & Fox P.L.L.C.

(57) ABSTRACT

The invention relates to novel 2,4,6-phenyl-substituted cyclic ketoenols of the formula (I),

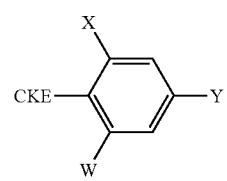

in which
CKE, W, X and Y are as defined above,
to a plurality of processes and intermediates for their preparation and to their use as pesticides and/or herbicides, and also to selective herbicidal compositions comprising firstly the 2,4,6-phenyl-substituted cyclic ketoenols and secondly at least one compound which improves crop plant tolerance.

5 Claims, No Drawings

U.S. PATENT DOCUMENTS

| | | |
|---|---|---|
| 5,314,863 A | 5/1994 | Löher et al. |
| 5,332,720 A | 7/1994 | Krüger et al. |
| 5,380,852 A | 1/1995 | Schütze et al. |
| 5,393,729 A | 2/1995 | Fischer et al. |
| 5,401,700 A | 3/1995 | Sohn et al. |
| 5,407,897 A | 4/1995 | Cary et al. |
| 5,494,890 A | 2/1996 | Cederbaum et al. |
| 5,504,057 A | 4/1996 | Fischer et al. |
| 5,516,750 A | 5/1996 | Willms et al. |
| 5,565,450 A | 10/1996 | Fischer et al. |
| 5,567,671 A | 10/1996 | Fischer et al. |
| 5,589,469 A | 12/1996 | Fischer et al. |
| 5,610,122 A | 3/1997 | Fischer et al. |
| 5,622,917 A | 4/1997 | Fischer et al. |
| 5,677,449 A | 10/1997 | Fischer et al. |
| 5,683,965 A | 11/1997 | Bachmann et al. |
| 5,700,758 A | 12/1997 | Rösch et al. |
| 5,739,079 A | 4/1998 | Holdgrün et al. |
| 5,808,135 A | 9/1998 | Fischer et al. |
| 5,811,374 A | 9/1998 | Bertram et al. |
| 5,830,825 A | 11/1998 | Fischer et al. |
| 5,830,826 A | 11/1998 | Fischer et al. |
| 5,840,661 A | 11/1998 | Fischer et al. |
| 5,922,732 A | 7/1999 | Urch et al. |
| 5,945,444 A | 8/1999 | Fischer et al. |
| 5,960,443 A | 9/1999 | Young et al. |
| 5,977,029 A | 11/1999 | Fischer et al. |
| 6,071,937 A | 6/2000 | Bretschneider et al. |
| 6,114,374 A | 9/2000 | Lieb et al. |
| 6,133,296 A | 10/2000 | Lieb et al. |
| 6,140,358 A | 10/2000 | Lieb et al. |
| 6,200,932 B1 | 3/2001 | Fischer et al. |
| 6,235,680 B1 | 5/2001 | Ziemer et al. |
| 6,251,827 B1 | 6/2001 | Ziemer et al. |
| 6,251,833 B1 | 6/2001 | Erdelen et al. |
| 6,316,486 B1 | 11/2001 | Lieb et al. |
| 6,358,887 B1 | 3/2002 | Fischer et al. |
| 6,410,480 B1 | 6/2002 | Mühlebach et al. |
| 6,472,419 B1 | 10/2002 | Fischer et al. |
| 6,515,184 B1 | 2/2003 | Fischer et al. |
| 6,555,499 B1 | 4/2003 | Glock et al. |
| 6,589,976 B1 | 7/2003 | Fischer et al. |
| 6,861,391 B1 | 3/2005 | Fischer et al. |
| 7,138,360 B2 | 11/2006 | Jäger et al. |
| 2002/0022575 A1 | 2/2002 | Fischer et al. |
| 2002/0061913 A1 | 5/2002 | Urch et al. |
| 2002/0072617 A1 | 6/2002 | Hagemann et al. |
| 2002/0188136 A1 | 12/2002 | Lieb et al. |
| 2003/0045432 A1 | 3/2003 | Fischer et al. |
| 2003/0073851 A1 | 4/2003 | Lieb et al. |
| 2003/0096806 A1 | 5/2003 | Lieb et al. |
| 2003/0171219 A1 | 9/2003 | Lieb et al. |
| 2003/0171220 A1 | 9/2003 | Ziemer et al. |
| 2003/0199572 A1 | 10/2003 | Lieb et al. |
| 2003/0216620 A1 | 11/2003 | Ruther et al. |
| 2003/0228984 A1 | 12/2003 | Hagemann et al. |
| 2004/0266624 A1 | 12/2004 | Hofer |
| 2005/0090399 A1 | 4/2005 | Friedmann et al. |
| 2005/0164883 A1 | 7/2005 | Maetzke et al. |
| 2005/0164886 A1 | 7/2005 | Glock |
| 2006/0160847 A1 | 7/2006 | Fischer et al. |
| 2006/0166829 A1 | 7/2006 | Fischer et al. |
| 2007/0066488 A1 | 3/2007 | Fischer et al. |

FOREIGN PATENT DOCUMENTS

| | | |
|---|---|---|
| CA | 2 518 620 A1 | 9/2004 |
| EP | 0 346 620 A1 | 12/1989 |
| GB | 2 266 888 A | 11/1993 |
| JP | 2000-53670 A | 2/2000 |
| WO | WO 94/29268 A1 | 12/1994 |
| WO | WO 96/02539 A1 | 2/1996 |
| WO | WO 96/11574 A1 | 4/1996 |
| WO | WO 96/21652 A1 | 7/1996 |
| WO | WO 01/17351 A1 | 3/2001 |
| WO | WO 01/17972 A2 | 3/2001 |
| WO | WO 01/58264 A2 | 8/2001 |
| WO | WO 02/02536 A1 | 1/2002 |
| WO | WO 02/17718 A1 | 3/2002 |

OTHER PUBLICATIONS

Askani, R., "Reaction of 1,3-cyclohexadiene with azodicarboxylic acid diethyl ester," Chem. Berichte 98:2551-2555, Verlag Chemie (1965).

Baciocchi, E., et al., "Dimethyl Arylmalonates from Cerium(IV) Ammonium Nitrate Promoted Reactions of Dimethyl Malonate with Aromatic Compounds in Methanol," Tetrahedron Lett. 27:2763-2766, Pergamon Journals Ltd. (1986).

Bhattacharya, B., "Isoquinoline Derivatives: Part XVIII—Formation of I-Alkyl-(or alkaryl or aryl)-3-methyl-7-chloro-(or 5-chloro)-isoquinolines," Indian J. Chem. 6:341-345, Council of Scientific & Industrial Research (1968).

Campbell, A.C., et al., "Synthesis of (E)- and (Z)-Pulvinones," J. Chem. Soc. Perkin Trans. 1:1567-1585, The Chemical Society (1985).

Chambers, M.S., et al., "An Asymmetric Synthesis of Thiotetronic Acids using Chirality Transfer via an Allyl Xanthate-to-Dithiocarbonate Rearrangement. X-Ray Crystal Structure of (5R)-2,5-Dihydro-4-hydroxy-5-methyl-3-phenyl-5-prop-1'-enyl-2-oxothiophene," J. Chem. Soc., Chem. Commun., pp. 1228-1230, Royal Society of Chemistry (1987).

Chirazi, a.M., et al., "Zur Synthese von Kawalactonderivaten," Arch. Pharm. 309:558-564, Deutschen Apotheker-Vereins (1976).

Clive, D.L.J., and Wang, J., "Synthesis of natural (−)-hamigeran B," Tetrahedron Lett. 44:7731-7733, Elsevier Ltd. (2003).

Compagnon, P.L., and Miocque, M., "Addition des Réactifs Nucléophiles Sur la Triple Liaison Nitrile," Ann. Chim. 5:11-22, Societa Chimica Italiana (1970).

Dannenberg, V.H. and Dannenberg-Von Dresler, D., "Verusche zur Synthese des „Steranthrens" III, Justus Liebigs Ann. Chem. 585:1-15, Verlag Chemie (1954).

Diels, V.O., et al., "Über das aus Cyclopentadien und Azoester entestehende Endomethylen-piperidazin und seine Überführung in 1,3-Diamino-cyclopentan," Justus Liebigs Ann. Chem. 443:242-262, Verlag Chemie (1925).

Edward, J.T., and Jitrangsri, C., "Stereochemistry of the Bucherer-Bergs and Strecker Reactions of 4-tert-Butylcyclohexanone," Can. J. Chem. 53:3339-3350, NRC Research Press (1975).

Edwards, R.L., et al., "Constituents of the Higher Fungi. Part IV. Involutin, a Diphenylcyclopenteneone from Paxillus involutus (Oeder ex Fries)," J. Chem. Soc. (C), pp. 405-409, Royal Society of Chemistry (1967).

Harrison, H.R., et al., "Use of molecular sieves in the methyl esterification of carboxylic acids," Chem. Ind., p. 1568, Society of Chemical Industry (1968).

Ketcham, R., et al., "Synthesis of Heterocycles. 174 (1,2) Substituted Thiazines and Bisthiazinyls from Dithiooxamide and Trichlorophenyl Malonates," Heterocycl. Chem. 10:223-224, Hetero Corporation (1973).

Micklefield, J., et al., "Alkylation and Acylation of 5-Phenylsulphonyl- and 5-Cyanobutyrolactones," Tetrahedron 48:7519-7526, Pergamon Press Ltd. (1992).

Munday, L., "Aminio-acids of the Cyclohexane Series. Part I.," J. Chem. Soc., pp. 4372-4379, Royal Society of Chemistry (1961).

Nakanishi, S., and Butler, K., "Synthesis of Chlorocarbonyl Ketenes," Organic Preparations and Procedures Int. 7:155-158, Organic Preparations and Procedures, Inc. (1975).

Schmierer, R., and Mildenberger, H., "Cyclisierung von N-Acylalanin- und N-Acylglycinestern," Liebigs Ann. Chem. 1985:1095-1098, VCH Verlagsgesellschaft mbH (1985).

Sonntag, N.O.V., "The Reactions of Aliphatic Acid Chlorides," Chem. Rev. 52:237-416, American Chemical Society (1953).

Sousa, A.A., et al., "Esters of 3-Hydroxy-2-Arlindones, a New Class of Acaricide," J. Economic Entomol. 66:584-586, Entomological Society of America (1973).

Suzuki, S., et al., "Studies on Antiviral Agents. IV. Biological Activity of Tenuazonic Acid Derivativs.," Chem Pharm. Bull. 15:1120-1122, Pharmaceutical Society of Japan (1967).

Tsuzuki, K., and Ōmura, S., "Syntheses and Biological Activities of Thiotetromycin Analogs," *J. Antibiot.* XXXVI:1589-1591, Japan Antibiotics Research Association (1983).

Wheeler, T.N., "Novel Photochemical Synthesis of 2-Aryl-1,3-cyclohexanediones," *J. Org. Chem.* 44:4906-4912, American Chemical Society (1979).

International Search Report for International Application No. PCT/EP2005/002605, European Patent Office, Netherlands, mailed on Jul. 13, 2005.

STNEasy Database, Accession No. 1965:463065, English language abstract for Askani, R., "Reaction of 1,3-cyclohexadiene with azodicarboxylic acid diethyl ester," *Chem. Berichte* 98:2551-2555, Verlag Chemie (1965).

STNEasy Database, Accession No. 1955:56638, English language abstract for Dannenberg, H. and Dannenberg-Von Dresler, D., "Synthesis of steranthrenes. III. 3,4-Aceperinaphthane and 6,7-aceperinaphtane," *Ann. Chem.* 585:1-15, Verlag Chemie (1954).

STNEasy Database, Accession No. 1925:19216, English language abstract for Diels, O., et al., "The endo-methylenepiperidazine resulting from cyclopentadiene and azo ester and its transformation into 1,3-diaminocyclopentane," *Ann. Chem.* 443:242-262, Verlag Chemie (1925).

Dialog File 351, Accession No. 4963457, English language abstract for EP 0 346 620 A1, published May 16, 1989 (listed on First Supplemental PTO/SB/08A form as document FP2).

Patent Abstracts of Japan, English language abstract for JP 2000-53670 A, published Feb. 22, 2000 (listed on First Supplemental PTO/SB/08A form as document FP8).

2,4,6-PHENYL-SUBSTITUTED CYCLIC KETOENOLS

This application is a 35 U.S.C. §371 U.S. National Phase filing of International Application No. PCT/EP2005/002605, filed Mar. 11, 2005, which claims the benefit of German Patent Application No. 102 004 014 620.9, filed Mar. 25, 2004.

Moreover, the invention relates to novel selective herbicidal active compound combinations comprising firstly the 2,4,6-phenyl-substituted cyclic ketoenols and secondly at least one compound which improves crop plant tolerance, which combinations can be used with particularly good results for the selective control of weeds in various crops of useful plants.

Pharmaceutical properties of 3-acylpyrrolidine-2,4-diones have already been described (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones), of which, however, no herbicidal, insecticidal or acaricidal action has been disclosed. Unsubstituted, bicyclic 3-arylpyrrolidine-2,4-dione derivatives (EP-A-355 599, EP-A-415 211 and JP-A-12-053670) and substituted monocyclic 3-arylpyrrolidine-2,4-dione derivatives (EP-A-377 893 and EP-A-442 077) having herbicidal, insecticidal or acaricidal action have been disclosed.

There have also been disclosed polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 94/01 997, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869, WO 99/55673, WO 01/17972, WO 01/23354, WO 01/74770, WO 03/062244, WO 04/024688, WO 04/007448, WO 04/080962, WO 04/065366, DE-A-10326386).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-2-one) is also described in DE-A-4 014 420. Compounds of a similar structure are known from the publication Campbell et al., J. Chem. Soc., Perkin Trans. 1, 1985, (8) 1567-76, but no insecticidal and/or acaricidal activity is mentioned. 3-Aryl-$\Delta^3$-dihydrofuranone derivatives having herbicidal, acaricidal and insecticidal properties are also known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/062244, WO 04/024688, WO 04/080962, DE-A-10326386). 3-Aryl-$\Delta^3$-dihydrothiophenone derivatives are likewise known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/062244, WO 04/080962, DE-A-10326386).

Certain phenylpyrone derivatives which are unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849), but a possible use of these compounds as pesticides has not been mentioned. Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972 and WO 01/74770, WO 03/062244, WO 04/080962, DE-A-10326386.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)), but a possible use of these compounds as pesticides has not been mentioned. 5-Phenyl-1,3-thiazine derivatives which are substituted in the phenyl ring and have herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972 and WO 01/74770, WO 03/062244, WO 04/080962, DE-A-10326386.

It is known that certain substituted 2-arylcyclopentanediones have herbicidal, insecticidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770, WO 03/062244, WO 04/080962, DE-A-10326386). Moreover, compounds having similar substitutions are known; 3-hydroxy-5,5-dimethyl-2-phenylcyclopent-2-en-1-one from the publication Micklefield et al., Tetrahedron, (1992), 7519-26, and the natural product involutin (−)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66, (1973), 584 and the Offenlegungsschrift (German Published Specification) DE-A 2 361 084, with herbicidal and acaricidal actions being mentioned.

It is known that certain substituted 2-arylcyclohexanediones have herbicidal, insecticidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770, WO 03/062244, WO 04/080962, DE-A-10326386).

It is known that certain substituted 4-arylpyrazolidine-3,5-diones have acaricidal, insecticidal and herbicidal properties (cf., for example, WO 92/16 510, EP-A-508 126, WO 96/11 574, WO 96/21 652, WO 99/47525, WO 01/17 351, WO 01/17 352, WO 01/17 353, WO 01/17 972, WO 01/17 973, WO 03/062244, WO 03/028 466, WO 04/080962, DE-A-10326386, DE-A-10331675).

However, the activity and/or activity spectrum of these compounds is, in particular at low application rates and concentrations, not always entirely satisfactory. Furthermore, these compounds are not always sufficiently well tolerated by plants.

We have now found novel compounds of the formula (I)

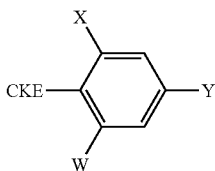
(I)

in which
W represents alkoxy, haloalkoxy, alkoxyalkoxy, alkoxybisalkoxy, bisalkoxyalkoxy or optionally substituted cycloalkylalkanediyloxy which may optionally be interrupted by heteroatoms,
X represents halogen,
Y represents alkyl,
CKE represents one of the groups

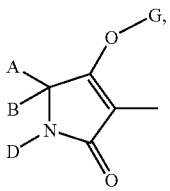
(1)

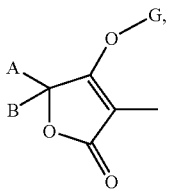
(2)

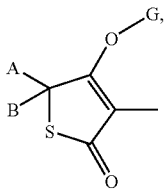
(3)

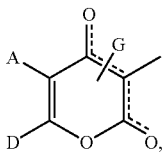
(4)

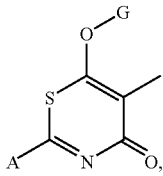
(5)

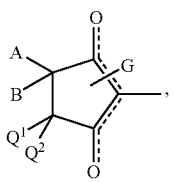
(6)

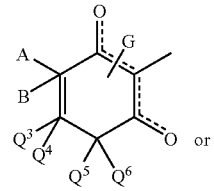
(7)

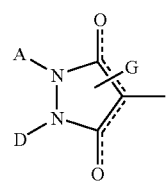
(8)

in which
A represents hydrogen, in each optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, haloalkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or an optionally substituted radical from the group consisting of alkyl, alkenyl, alkynyl, alkoxyalkyl, saturated or unsaturated cycloalkyl in which optionally one or more ring members are replaced by heteroatoms, arylalkyl, aryl, hetarylalkyl or hetaryl or A and D together with the atoms to which they are attached represent a saturated or unsaturated cycle which optionally (only in the case of CKE=1) contains at least one heteroatom and which is unsubstituted or substituted in the A,D moiety, or A and $Q^1$ together represent alkanediyl or alkenediyl optionally substituted by hydroxyl or by in each case optionally substituted alkyl, alkoxy, alkylthio, cycloalkyl, benzyloxy or aryl or $Q^1$ represents hydrogen or alkyl, $Q^2$, $Q^4$, $Q^5$ and $Q^6$ independently of one another represent hydrogen or alkyl, $Q^3$ represents hydrogen, represents optionally substituted alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated, unsubstituted or substituted cycle which optionally contains a heteroatom, G represents hydrogen (a) or represents one of the groups

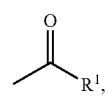
(b)

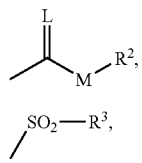
(c)

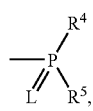
(d)

(e)

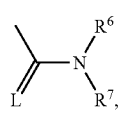
(f)

E or (g)

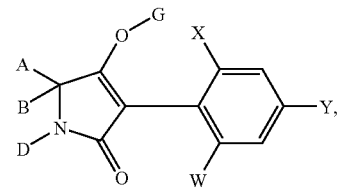

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, their preparation and use and compositions comprising them. However, for the sake of simplicity, hereinbelow only compounds of the formula (I) are referred to, although what is meant is both the pure compounds and, if appropriate, mixtures having various proportions of isomeric compounds.

Taking into consideration the meanings (1) to (8) of the group CKE, the following principle structures (I-1) to (I-8) result:

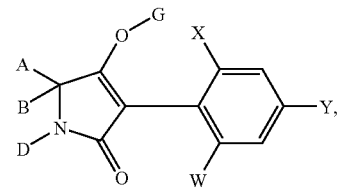
(I-1)

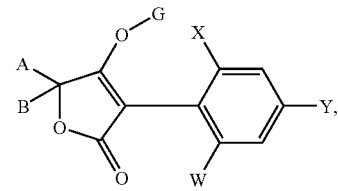
(I-2)

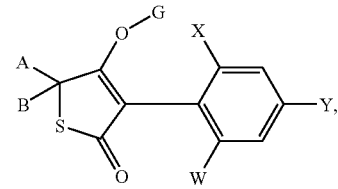
(I-3)

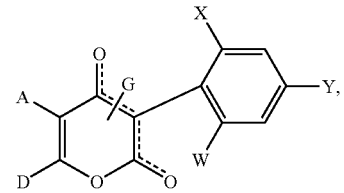
(I-4)

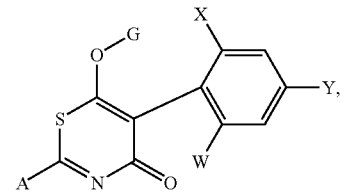
(I-5)

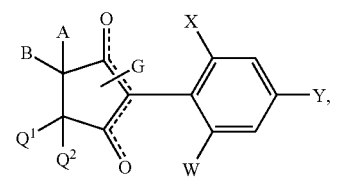
(I-6)

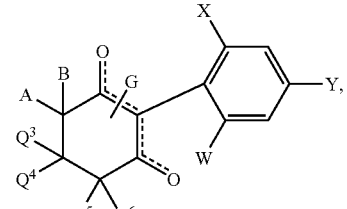
(I-7)

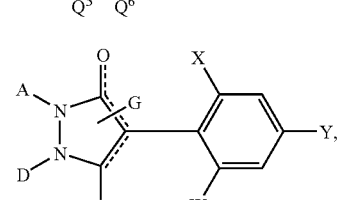
(I-8)

in which
A, B, D, G, $Q^1$, $Q^2$, $Q^3$, $Q^4$, $Q^5$, $Q^6$, W, X and Y are as defined above.

Taking into consideration the different meanings (a), (b), (c), (d), (e), (f) and (g) of the group G, the following principle structures (I-1-a) to (I-1-g) result if CKE represents the group (1)

(I-1-a):

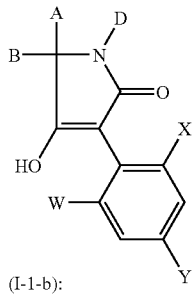

(I-1-b):

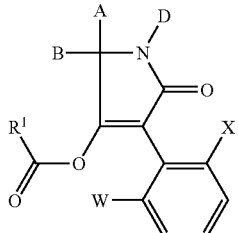

(I-1-c):

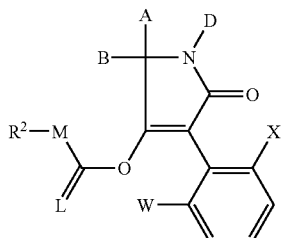

(I-1-d):

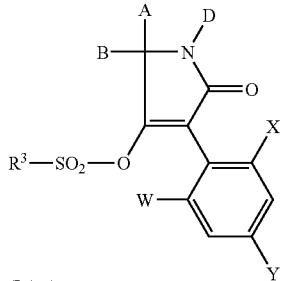

(I-1-e):

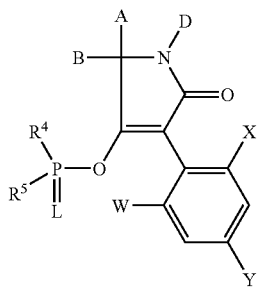

(I-1-f):

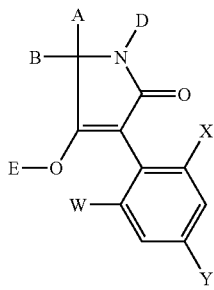

(I-1-g):

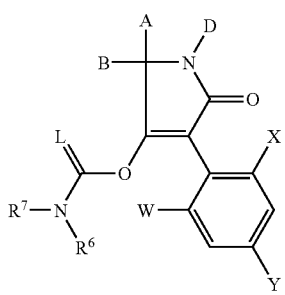

in which
A, B, D, E, L, M, W, X, Y, $R^1$, $R^2$, $R^3$, $R^4$, $R^5$, $R^6$ and $R^7$ are as defined above.

Taking into consideration the different meanings (a), (b), (c), (d), (e), (f) and (g) of the group G, the following principle structures (I-2-a) to (I-2-g) result if CKE represents the group (2)

(I-2-a):

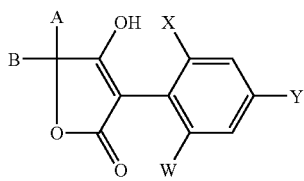

(I-2-b):

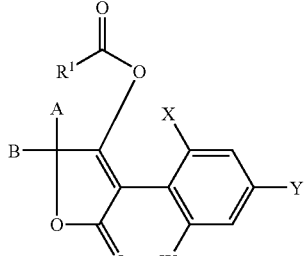

(I-2-c):

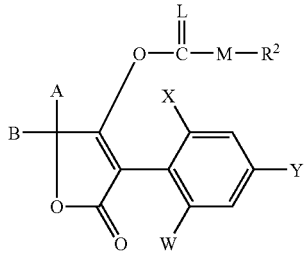

(I-2-d):
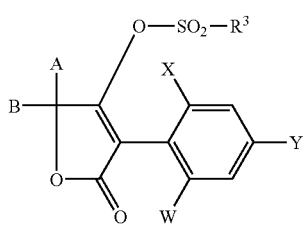
(I-2-e):
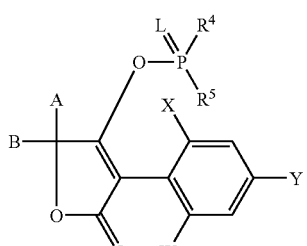
(I-2-f):
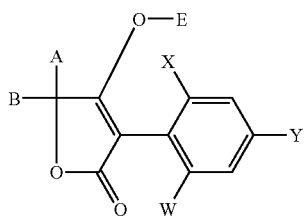
(I-2-g):
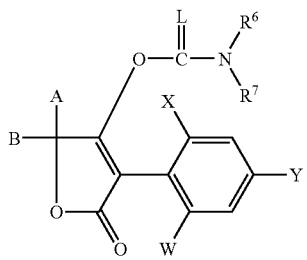
in which
A, B, E, L, M, W, X, Y, $R^1$, $R^2$, $R^3$, $R^4$, $R^5$, $R^6$ and $R^7$ are as defined above.
Taking into consideration the different meanings (a), (b), (c), (d), (e), (f) and (g) of the group G, the following principle structures (I-3-a) to (I-3-g) result if CKE represents the group (3)
(I-3-a):
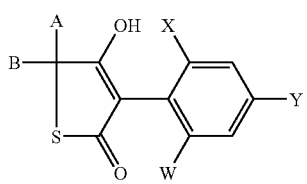
(I-3-b):
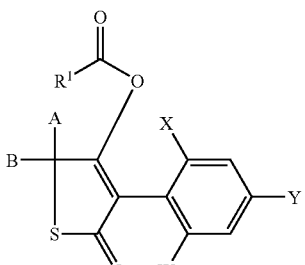
(I-3-c):
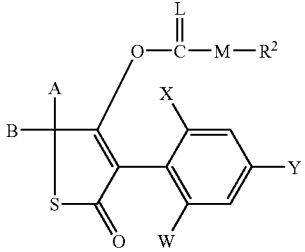
(I-3-d):
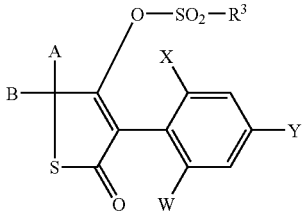
(I-3-e):
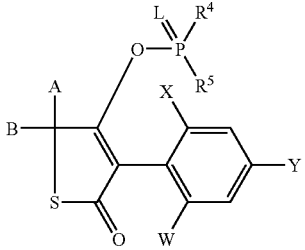
(I-3-f):
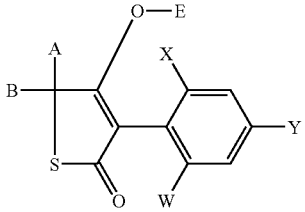
(I-3-g):
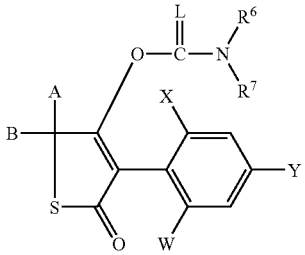

in which
A, B, E, L, M, W, X, Y, $R^1$, $R^2$, $R^3$, $R^4$, $R^5$, $R^6$ and $R^7$ are as defined above.

Depending on the position of the substituent G, the compounds of the formula (I-4) can be present in the two isomeric forms of the formulae (I-4-A) and (I-4-B)

(I-4-A)

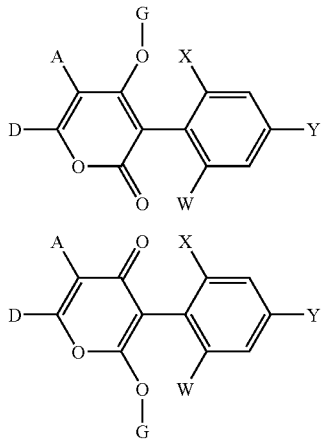

(I-4-B)

which is meant to be indicated by the broken line in the formula (I-4).

The compounds of the formulae (I-4-A) and (I-4-B) can be present both as mixtures and in the form of their pure isomers. Mixtures of the compounds of the formulae (I-4-A) and (I-4-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-4-a) to (I-4-g) result if CKE represents the group (4), (I-4-a):

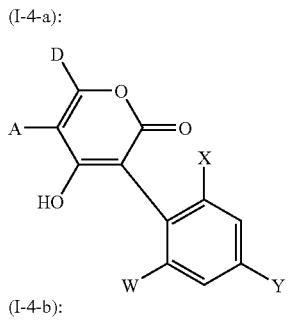

(I-4-b):

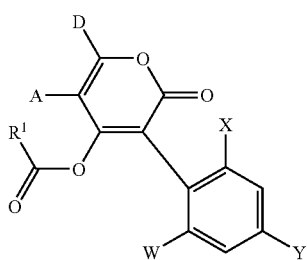

(I-4-c):

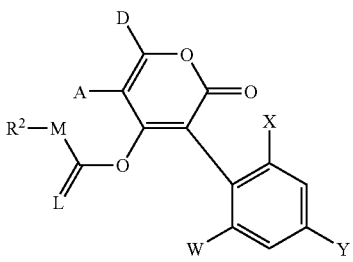

(I-4-d):

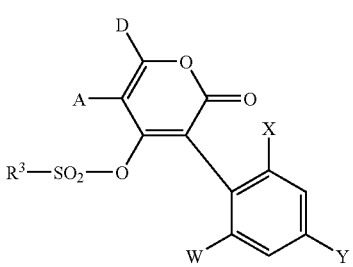

(I-4-e):

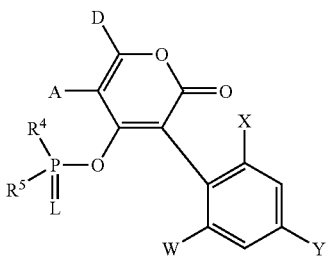

(I-4-f):

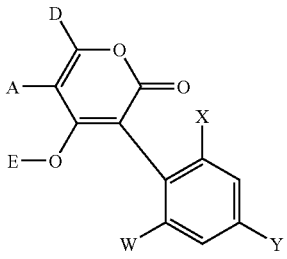

(I-4-g):

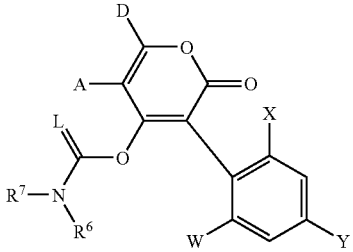

in which
A, D, E, L, M, W, X, Y, $R^1$, $R^2$, $R^3$, $R^4$, $R^5$, $R^6$ and $R^7$ are as defined above.

Taking into consideration the different meanings (a), (b), (c), (d), (e), (f) and (g) of the group G, the following principle structures (I-5-a) to (I-5-g) result if CKE represents the group (5), (I-5-a):

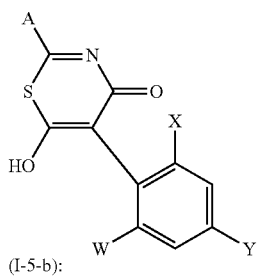

(I-5-b):

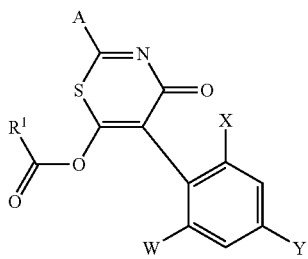

(I-5-c):

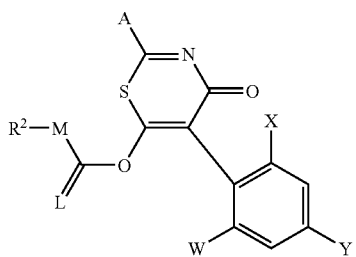

(I-5-d):

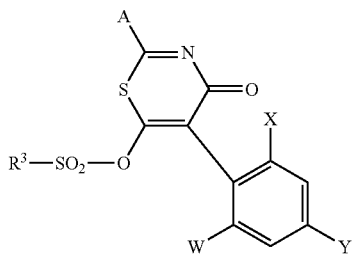

(I-5-e):

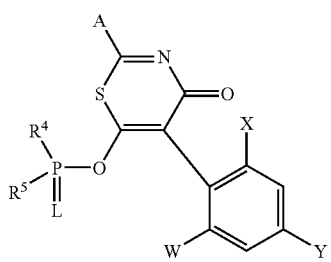

(I-5-f):

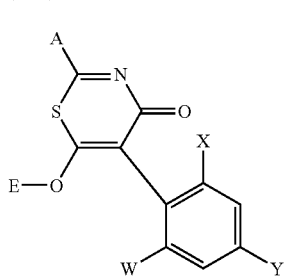

(I-5-g):

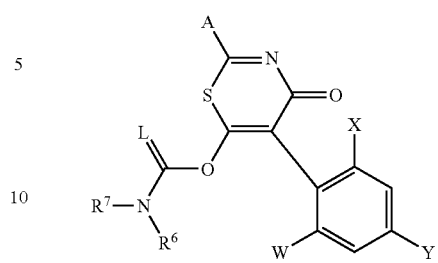

in which

A, E, L, M, W, X, Y, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B)

(I-6-A)

(I-6-B)

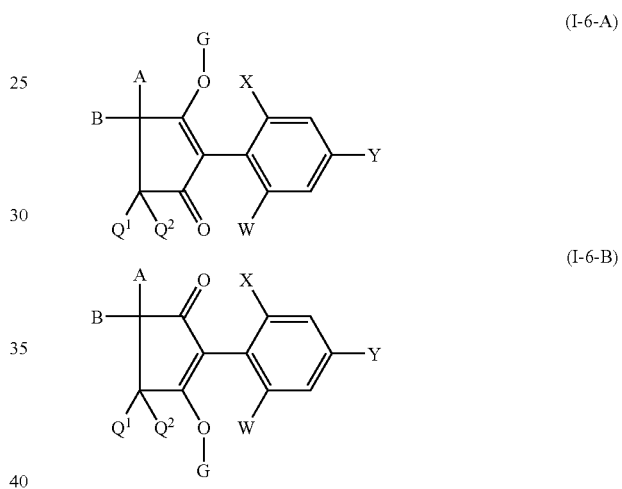

which is meant to be indicated by the broken line in the formula (I-6).

The compounds of the formulae (I-6-A) and (I-6-B) can be present both as mixtures and in the form of their pure isomers. Mixtures of the compounds of the formulae (I-6-A) and (I-6-B) can, if appropriate, be separated by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-6-a) to (I-6-g) result:

(I-6-a):

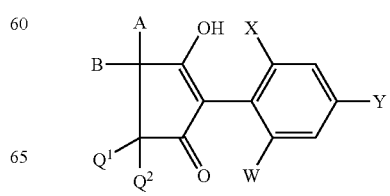

-continued (I-6-b):

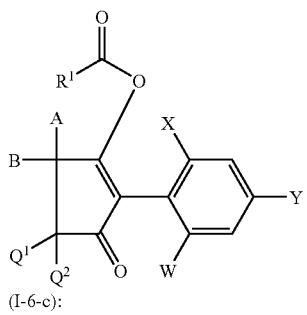

(I-6-c):

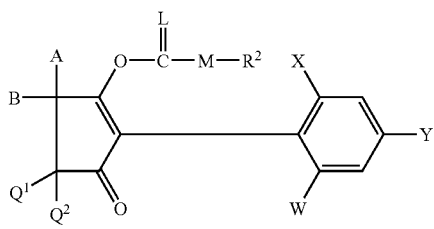

(I-6-d):

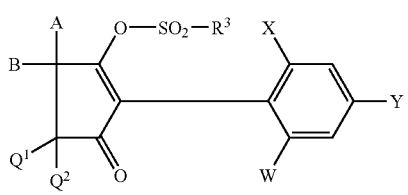

(I-6-e):

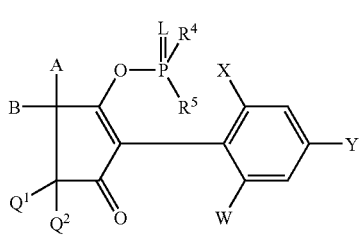

(I-6-f):

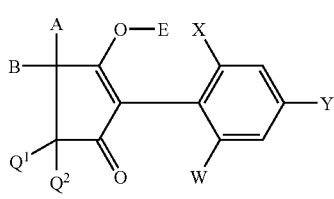

(I-6-g):

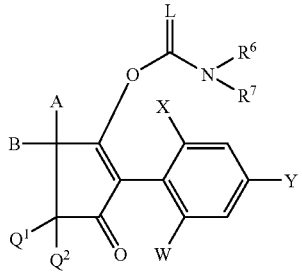

in which
A, B, $Q^1$, $Q^2$, E, L, M, W, X, Y, $R^1$, $R^2$, $R^3$, $R^4$, $R^5$, $R^6$ and $R^7$ are as defined above.

Depending on the position of the substituent G, the compounds of the formula (I-7) can be present in the two isomeric forms of the formulae (I-7-A) and (I-7-B), which is meant to be indicated by the broken line in the formula (I-7):

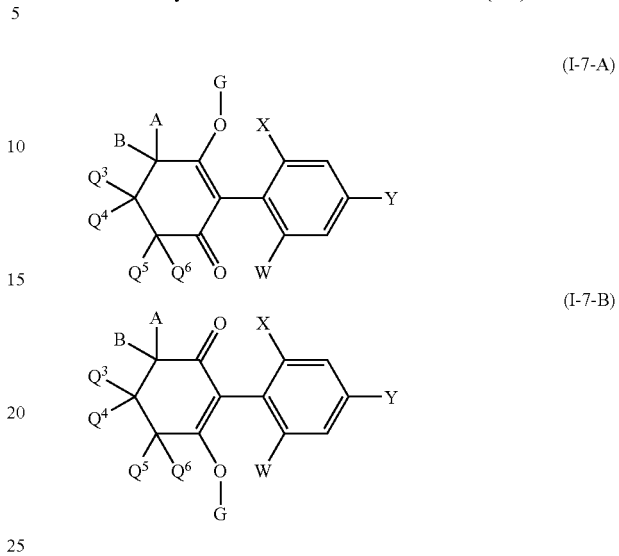

(I-7-A)

(I-7-B)

The compounds of the formulae (I-7-A) and (I-7-B) can be present both as mixtures and in the form of their pure isomers. Mixtures of the compounds of the formulae (I-7-A) and (I-7-B) can, if appropriate, be separated by physical methods, for example by chromatographic methods.

For reasons of clarity, hereinbelow only one of the possible isomers is shown in each case. This includes that the compound in question may, if appropriate, be present in the form of the isomer mixture or in the respective other isomeric form.

Taking into consideration the different meanings (a), (b), (c), (d), (e), (f) and (g) of the group G, the following principle structures (I-7-a) to (I-7-g) result:

(I-7-a):

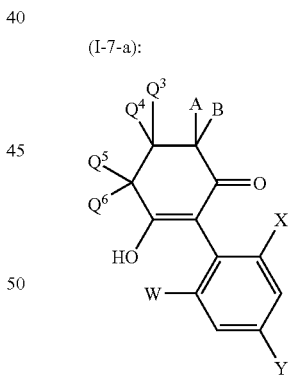

(I-7-b):

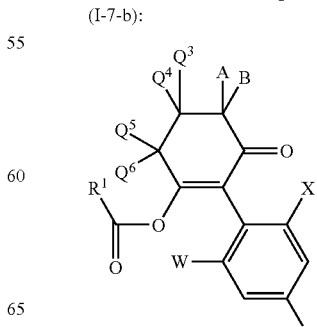

-continued (I-7-c): 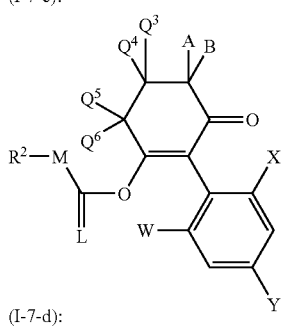

(I-7-d): 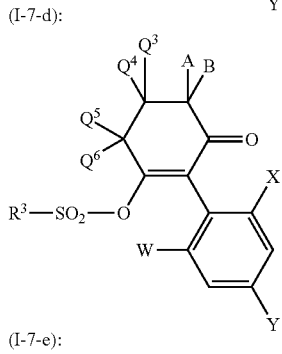

(I-7-e): 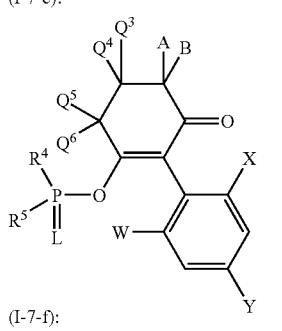

(I-7-f): 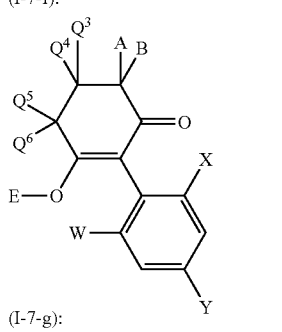

(I-7-g): 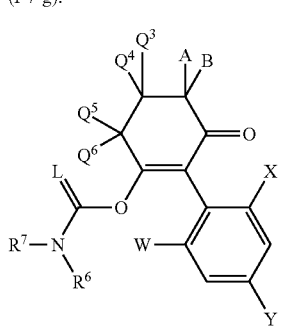

in which
A, B, E, L, M, $Q^3$, $Q^4$, $Q^5$, $Q^6$, W, X, Y, $R^1$, $R^2$, $R^3$, $R^4$, $R^5$, $R^6$ and $R^7$ are as defined above.

Depending on the position of the substituent G, the compounds of the formula (I-8) can be present in the two isomeric forms of the formulae (I-8-A) and (I-8-B)

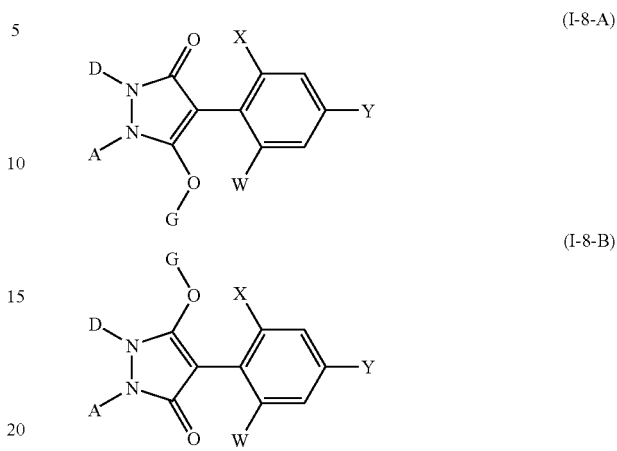

which is meant to be indicated by the broken line in formula (I-8).

The compounds of the formulae (I-8-A) and (I-8-B) can be present both as mixtures and in the form of their pure isomers. Mixtures of the compounds of the formulae (I-8-A) and (I-8-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-8-a) to (I-8-g) result if CKE represents the group (8),

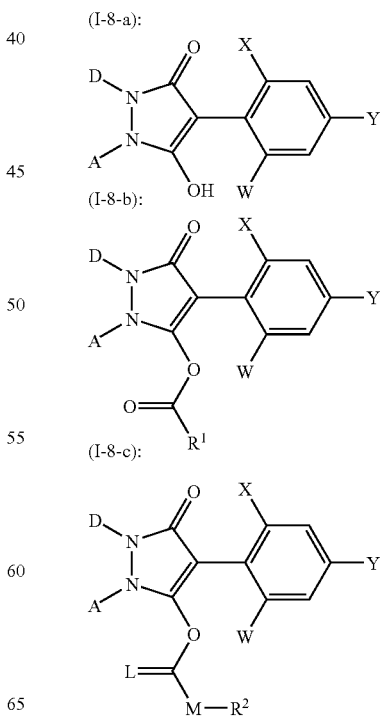

-continued (I-8-d):

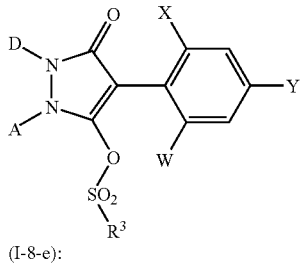

(I-8-e):

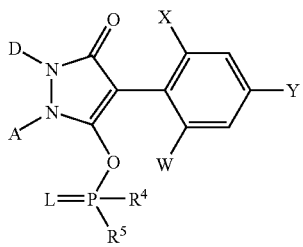

(I-8-f):

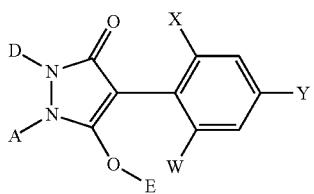

(I-8-g):

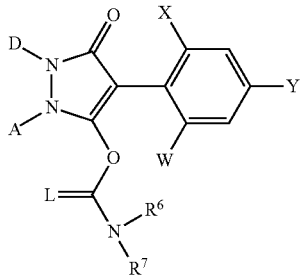

in which
A, D, E, L, M, W, X, Y, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) substituted 3-phenylpyrrolidine-2,4-diones or enols thereof of the formula (I-1-a)

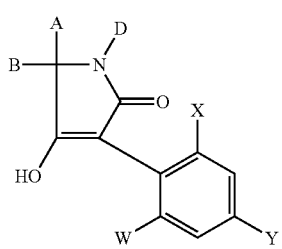

(I-1-a)

in which
A, B, D, W, X and Y are as defined above are obtained when
N-acylamino acid esters of the formula (II)

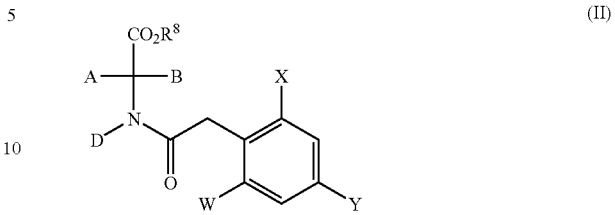

(II)

in which
A, B, D, W, X and Y are as defined above
and
$R^8$ represents alkyl (preferably $C_1$-$C_6$-alkyl)
are condensed intramolecularly in the presence of a diluent and in the presence of a base.

(B) Moreover, it has been found that substituted 3-phenyl-4-hydroxy-$\Delta^3$-dihydrofuranone derivatives of the formula (I-2-a)

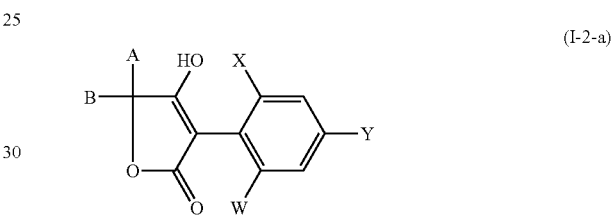

(I-2-a)

in which
A, B, W, X and Y are as defined above
are obtained when
carboxylic esters of the formula (III)

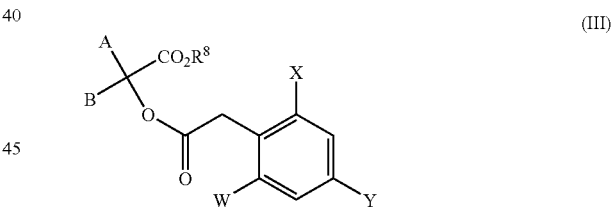

(III)

in which
A, B, W, X, Y and $R^8$ are as defined above
are condensed intramolecularly in the presence of a diluent and in the presence of a base.

(C) Furthermore, it has been found that substituted 3-phenyl-4-hydroxy-$\Delta^3$-dihydrothio-phenone derivatives of the formula (I-3-a)

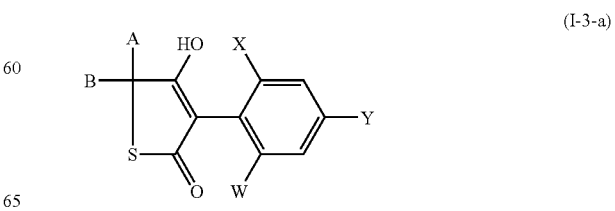

(I-3-a)

in which

A, B, W, X and Y are as defined above are obtained when

β-ketocarboxylic esters of the formula (IV)

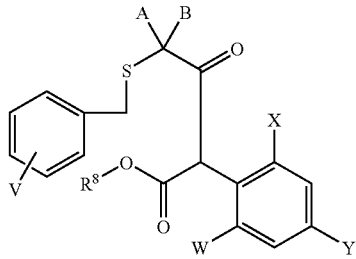
(IV)

in which

A, B, W, X, Y and $R^8$ are as defined above and

V represents hydrogen, halogen, alkyl (preferably $C_1$-$C_6$-alkyl) or alkoxy (preferably $C_1$-$C_8$-alkoxy)

are cyclized intramolecularly, if appropriate in the presence of a diluent and in the presence of an acid.

(D) Furthermore, it has been found that the novel substituted 3-phenylpyrone derivatives of the formula (I-4-a)

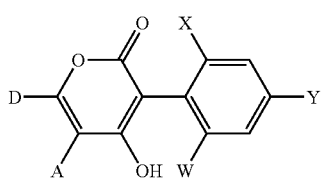
(I-4-a)

in which

A, D, W, X and Y are as defined above are obtained when carbonyl compounds of the formula (V)

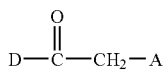
(V)

in which

A and D are as defined above or silylenol ethers thereof of the formula (Va)

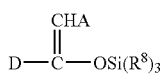
(Va)

in which

A, D and $R^8$ are as defined above are reacted with ketene acid halides of the formula (VI)

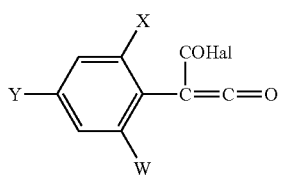
(VI)

in which

W, X and Y are as defined above and

Hal represents halogen (preferably chlorine or bromine), if appropriate in the presence of a diluent and if appropriate in the presence of an acid acceptor.

Furthermore, it has been found (E) that the novel substituted phenyl-1,3-thiazine derivatives of the formula (I-5-a)

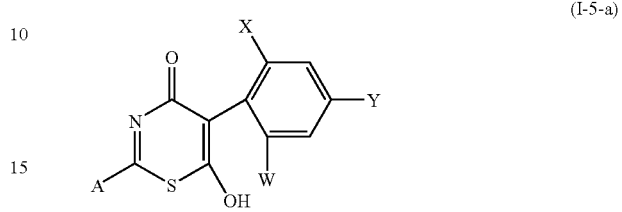
(I-5-a)

in which

A, W, X and Y are as defined above are obtained when thioamides of the formula (VII)

(VII)

in which

A is as defined above are reacted with ketene acid halides of the formula (VI)

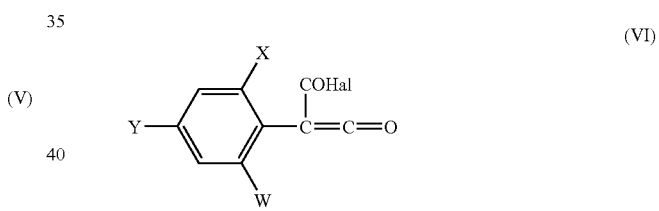
(VI)

in which

Hal, W, X and Y are as defined above, if appropriate in the presence of a diluent and if appropriate in the presence of an acid acceptor.

Furthermore, it has been found (F) that compounds of the formula (I-6-a)

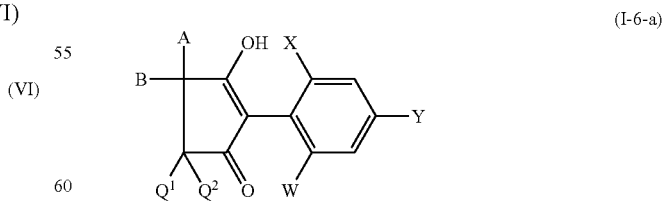
(I-6-a)

in which

A, B, $Q^1$, $Q^2$, W, X and Y are as defined above are obtained when ketocarboxylic esters of the formula (VIII)

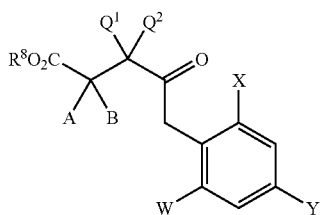

in which
A, B, Q¹, Q², W, X and Y are as defined above and
R⁸ represents alkyl (in particular $C_1$-$C_8$-alkyl)
are cyclized intramolecularly, if appropriate in the presence of a diluent and if appropriate in the presence of a base.

Moreover, it has been found
(G) that compounds of the formula (I-7-a)

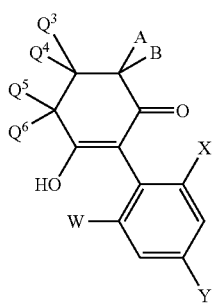

in which
A, B, Q³, Q⁴, Q⁵, Q⁶, W, X and Y are as defined above
are obtained when
6-aryl-5-ketohexanoic esters of the formula (IX)

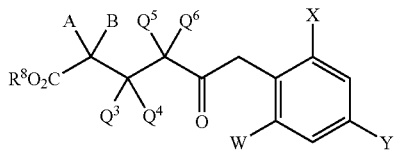

in which
A, B, Q³, Q⁴, Q⁵, Q⁶, W, X and Y are as defined above
and
R⁸ represents alkyl (preferably $C_1$-$C_6$-alkyl)
are condensed intramolecularly in the presence of a diluent and in the presence of a base.
(H) Furthermore, is has been found that the compounds of the formula (I-8-a)

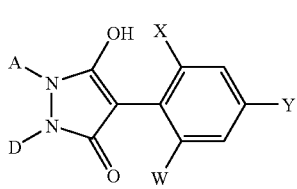

in which
A, D, W, X and Y are as defined above
are obtained when compounds of the formula (X)

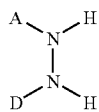

in which
A and D are as defined above
α) are reacted with compounds of the formula (VI)

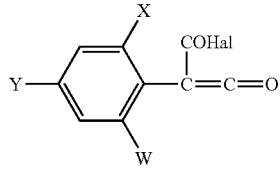

in which
Hal, X, Y and W are as defined above,
if appropriate in the presence of a diluent and if appropriate in the presence of an acid acceptor, or
β) are reacted with compounds of the formula (XI)

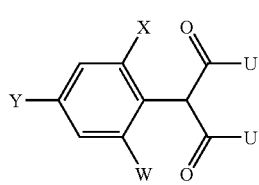

in which
W, X and Y are as defined above
and U represents $NH_2$ or $O—R^8$, where $R^8$ is as defined above,
if appropriate in the presence of a diluent and if appropriate in the presence of a base, or
γ) are reacted with compounds of the formula (XII)

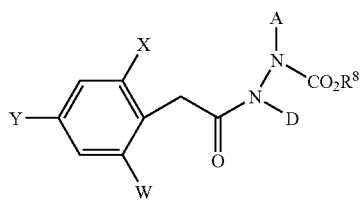

in which
A, D, W, X, Y and R⁸ are as defined above,
if appropriate in the presence of a diluent and if appropriate in the presence of a base.

Moreover, it has been found
(I) that the compounds of the formulae (I-1-b) to (I-8-b) shown above in which A, B, D, Q¹, Q², Q³, Q⁴, Q⁵, Q⁶, R¹, W, X and Y are as defined above are obtained when compounds of the formulae (I-1-a) to (I-8-a) shown above in which A, B, D, Q¹, Q², Q³, Q⁴, Q⁵, Q⁶, W, X and Y are as defined above are in each case (α) reacted with acid halides of the formula (XIII)

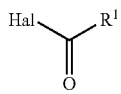

(XIII)

in which
R¹ is as defined above and
Hal represents halogen (in particular chlorine or bromine)
or
(β) reacted with carboxylic anhydrides of the formula (XIV)

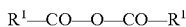
R¹—CO—O—CO—R¹  (XIV)

in which
R¹ is as defined above,
if appropriate in the presence of a diluent and if appropriate in the presence of an acid binder;

(J) that the compounds of the formulae (I-1-c) to (I-8-c) shown above in which A, B, D, $Q^1$, $Q^2$, $Q^3$, $Q^4$, $Q^5$, $Q^6$, $R^2$, M, W, X and Y are as defined above and L represents oxygen are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case reacted with chloroformic esters or chloroformic thioesters of the formula (XV)

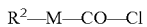
R²—M—CO—Cl  (XV)

in which
R² and M are as defined above,
if appropriate in the presence of a diluent and if appropriate in the presence of an acid binder;

(K) that compounds of the formulae (I-1-c) to (I-8-c) shown above in which A, B, D, $Q^1$, $Q^2$, $Q^3$, $Q^4$, $Q^5$, $Q^6$, $R^2$, M, W, X and Y are as defined above and L represents sulphur are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case reacted with chloromonothioformic esters or chlorodithioformic esters of the formula (XVI)

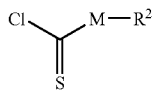

(XVI)

in which
M and R² are as defined above,
if appropriate in the presence of a diluent and if appropriate in the presence of an acid binder
and (L) that compounds of the formulae (I-1-d) to (I-8-d) shown above in which A, B, D, $Q^1$, $Q^2$, $Q^3$, $Q^4$, $Q^5$, $Q^6$, $R^3$, W, X and Y are as defined above are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case reacted with sulphonyl chlorides of the formula (XVII)

R³—SO₂—Cl  (XVII)

in which
R³ is as defined above,
if appropriate in the presence of a diluent and if appropriate in the presence of an acid binder, (M) that compounds of the formulae (I-1-e) to (I-8-e) shown above in which A, B, D, L, $Q^1$, $Q^2$, $Q^3$, $Q^4$, $Q^5$, $Q^6$, $R^4$, $R^5$, W, X and Y are as defined above are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case
reacted with phosphorus compounds of the formula (XVIII)

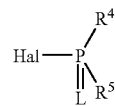

(XVIII)

in which
L, R⁴ and R⁵ are as defined above and
Hal represents halogen (in particular chlorine or bromine),
if appropriate in the presence of a diluent and if appropriate in the presence of an acid binder, (N) that compounds of the formulae (I-1-f) to (I-8-f) shown above in which A, B, D, E, $Q^1$, $Q^2$, $Q^3$, $Q^4$, $Q^5$, $Q^6$, W, X and Y are as defined above are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case
reacted with metal compounds or amines of the formulae (XIX) and (XX), respectively,

Me(OR¹⁰)ₜ  (XIX)

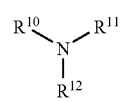

(XX)

in which
Me represents a mono- or divalent metal (preferably an alkali metal or alkaline earth metal, such as lithium, sodium, potassium, magnesium or calcium),
t represents the number 1 or 2 and
R¹⁰, R¹¹, R¹² independently of one another represent hydrogen or alkyl (preferably $C_1$-$C_8$-alkyl),
if appropriate in the presence of a diluent, (O) that compounds of the formulae (I-1-g) to (I-8-g) shown above in which A, B, D, L, $Q^1$, $Q^2$, $Q^3$, $Q^4$, $Q^5$, $Q^6$, $R^6$, $R^7$, W, X and Y are as defined above are obtained when compounds of the formulae (I-1-a) to (I-8-a) shown above in which A, B, D, $Q^1$, $Q^2$, $Q^3$, $Q^4$, $Q^5$, $Q^6$, W, X and Y are as defined above are in each case (α) reacted with isocyanates or isothiocyanates of the formula (XXI)

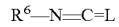
R⁶—N=C=L  (XXI)

in which
R⁶ and L are as defined above,
if appropriate in the presence of a diluent and if appropriate in the presence of a catalyst, or (β) reacted with carbamoyl chlorides or thiocarbamoyl chlorides of the formula (XXII)

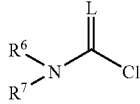
(XXII)

in which

L, $R^6$ and $R^7$ are as defined above, if appropriate in the presence of a diluent and if appropriate in the presence of an acid binder, (P) that compounds of the formulae (I-1-a) to (I-8-a) shown above in which A, B, D, $Q^1$, $Q^2$, $Q^3$, $Q^4$, $Q^5$, $Q^6$, W, X and Y are as defined above are obtained when compounds of the formulae (I-1-a') to (I-8-a') shown above in which A, B, D, $Q^1$, $Q^2$, $Q^3$, $Q^4$, $Q^5$, $Q^6$, X and Y are as defined above and W' preferably represents bromine

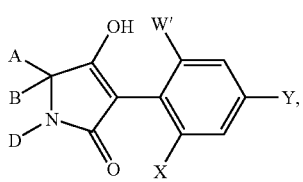
(I-1-a')

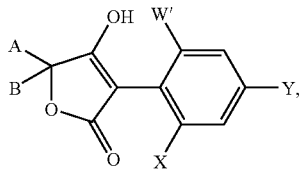
(I-2-a')

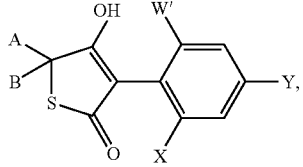
(I-3-a')

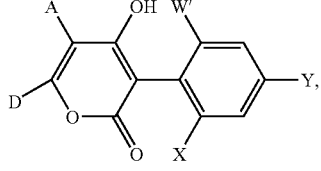
(I-4-a')

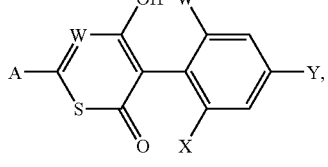
(I-5-a')

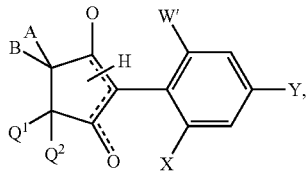
(I-6-a')

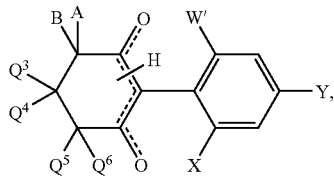
(I-7-a')

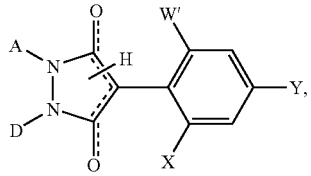
(I-8-a')

are reacted with alcohols of the formula

W—OH in which
W is as defined above, if appropriate in the presence of a diluent, a Cu(I) salt (for example CuBr, CuI) and a strong base (for example sodium hydride, potassium tert-butoxide).

Furthermore, it has been found that the novel compounds of the formula (I) are highly active as pesticides, preferably as insecticides, acaricides and herbicides.

Surprisingly, it has now also been found that certain substituted cyclic ketoenols, when used jointly with the compounds which improve crop plant tolerance (safeners/antidotes) described below, are extremely effective in preventing damage to the crop plants and can be used especially advantageously as combination products with a broad range of activity for the selective control of unwanted plants in crops of useful plants, such as, for example, in cereals, but also in maize, soybeans and rice.

The invention also relates to selective herbicidal compositions with an effective content of an active compound combination comprising, as components, a') at least one substituted cyclic ketoenol of the formula (I) in which CKE, W, X and Y are as defined above
and
(b') at least one compound which improves crop plant tolerance and which is selected from the following group of compounds:
4-dichloroacetyl-1-oxa-4-aza-spiro[4.5]-decane (AD-67, MON-4660), 1-dichloroacetylhexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloroquinolin-8-oxy-acetate (cloquintocet-mexyl—cf. also related compounds in EP-A-86750, EP-A-94349, EP-A-191736, EP-A492366), 3-(2-chloro-benzyl)-1-(1-methyl-1-phenyl-ethyl)-urea (cumyluron), α-(cyanomethoximino)-phenylacetonitrile (cyometrinil), 2,4-dichlorophenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl-acetamide (dichlormid), 4,6-dichloro-2-phenylpyrimidine (fenclorim), ethyl 1-(2,4-dichloro-phenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4- trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)-ethyl-3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 2-propenyl-1-oxa-4-azaspiro[4.5]decane 4-carbodithioate (MG-838), 1,8-naphthalic anhydride, α-(1,3-dioxolan-2-yl-methoxyimino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chlorophenoxy)-butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl) 5-phenyl-1H-pyrazole-3-carboxylate (cf also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluorophenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinoxalin-8-oxy-acetate, ethyl 5-chloro-quinolin-8-oxy-acetate, allyl 5-chloro-quinoxalin-8-oxy-acetate, 2-oxo-prop-1-yl 5-chloro-quinolin-8-oxy-acetate, diethyl 5-chloro-quinolin-8-oxy-malonate, diallyl 5-chloro-quinoxalin-8-oxy-malonate, diethyl 5-chloro-quinolin-8-oxy-malonate (cf. also related compounds in EP-A-582198), 4-carboxy-chroman-4-yl-acetic acid (AC-304415, cf. EP-A-613618), 4-chloro-phenoxy-acetic acid, 3,3'-dimethyl-4-methoxy-benzophenone, 1-bromo-4-chloromethylsulphonyl-benzene, 1-[4-(N-2-methoxybenzoyl-sulphamoyl)-phenyl]-3-methyl-urea (alias N-(2-methoxy-benzoyl)-4-[(methylamino-carbonyl)-amino]-benzenesulphonamide), 1-[4-(N-2-methoxybenzoylsulphamoyl)-phenyl]-3,3-dimethyl-urea, 1-[4-(N-4,5-dimethylbenzoylsulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropylaminocarbonyl)-benzenesulphonamide, and/or one of the following compounds (defined by general formulae)

of the general formula (IIa)

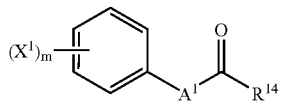

(IIa)

or of the general formula (IIb)

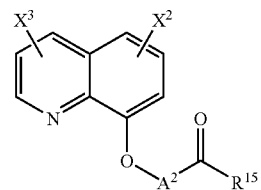

(IIb)

or of the formula (IIc)

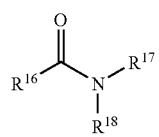

(IIc)

where m is 0, 1, 2, 3, 4 or 5, $A^1$ represents one of the divalent heterocyclic groups outlined hereinbelow,

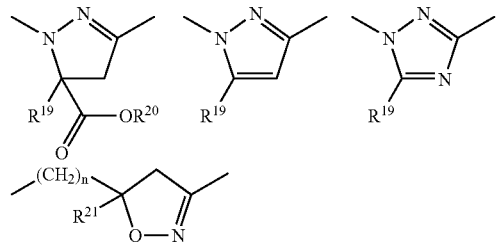

n is 0, 1, 2, 3, 4 or 5, $A^2$ represents alkanediyl having 1 or 2 carbon atoms which is optionally substituted by $C_1$-$C_4$-alkyl and/or $C_1$-$C_4$-alkoxy-carbonyl and/or $C_1$-$C_4$-alkenyloxy-carbonyl, $R^{14}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)amino, $R^{15}$ represents hydroxyl, mercapto, amino, $C_1$-$C_7$-alkoxy, $C_1$-$C_6$-alkenyloxy, $C_1$-$C_6$-alkenyloxy-$C_1$-$C_6$-alkoxy, $C_1$-$C_6$-alkylthio, $C_1$-$C_6$-alkylamino or di-($C_1$-$C_4$-alkyl)amino, $R^{16}$ represents $C_1$-$C_4$-alkyl which is optionally substituted in each case by fluorine, chlorine and/or bromine, $R^{17}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, $R^{18}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, $R^{17}$ and $R^{18}$ together also represent $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are bonded, form a 5- or 6-membered carbocycle, $R^{19}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $R^{20}$ represents hydrogen, or represents $C_1$-$C_6$-alkyl, $C_3$-$C_6$-cycloalkyl or tri($C_1$-$C_4$-alkyl)silyl, each of which is optionally substituted by hydroxyl, cyano, halogen or $C_1$-$C_4$-alkoxy, $R^{21}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds (defined by general formulae)
of the general formula (IId)

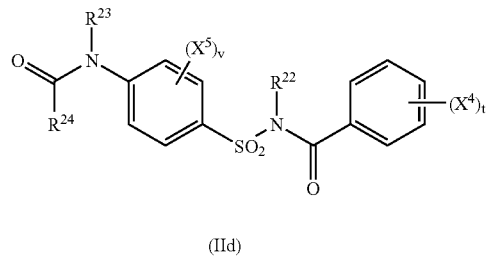

(IId)

or of the general formula (IIe)

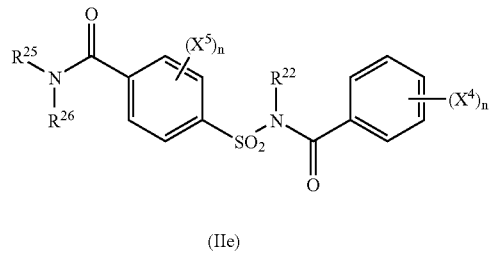

(IIe)

where
t is 0, 1, 2, 3, 4 or 5,
v is 0, 1, 2, 3, 4 or 5,
$R^{22}$ represents hydrogen or $C_1$-$C_4$-alkyl,
$R^{23}$ represents hydrogen or $C_1$-$C_4$-alkyl,
$R^{24}$ represents hydrogen, or represents $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)amino, each of which is optionally substituted by cyano, halogen or $C_1$-$C_4$-alkoxy, or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{25}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, $R^{26}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, or represents phenyl which is optionally substituted by nitro, cyano, halogen, $C_1$-$C_4$-alkyl, $C_1$-$C_4$-haloalkyl, $C_1$-$C_4$-alkoxy or $C_1$-$C_4$-haloalkoxy, or together with $R^{25}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

The formula (I) provides a general definition of the compounds according to the invention. Preferred substituents or ranges of the radicals given in the formulae mentioned hereinabove and hereinbelow are illustrated below:

W preferably represents $C_1$-$C_6$-alkoxy, $C_1$-$C_6$-haloalkoxy, $C_1$-$C_4$-alkoxy-$C_2$-$C_4$-alkoxy, $C_1$-$C_4$-alkoxy-bis-$C_2$-$C_4$-alkoxy or $C_3$-$C_6$-cycloalkyl-$C_1$-$C_2$-alkanediyloxy which is optionally mono- to trisubstituted by fluorine, chlorine, $C_1$-$C_3$-alkyl or $C_1$-$C_3$-alkoxy and in which optionally one methylene group of the ring may be interrupted by oxygen or sulphur, X preferably represents halogen,
Y preferably represents $C_1$-$C_4$-alkyl,
CKE preferably represents one of the groups

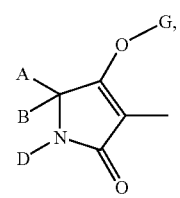

(1)

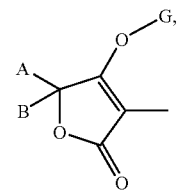

(2)

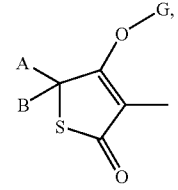

(3)

-continued

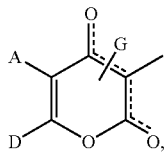
(4)

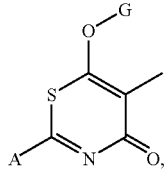
(5)

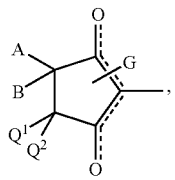
(6)

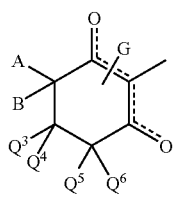
(7)

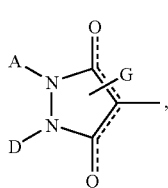
(8)

A preferably represents hydrogen or in each case optionally halogen-substituted $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, optionally halogen-, $C_1$-$C_6$-alkyl- or $C_1$-$C_6$-alkoxy-substituted $C_3$-$C_8$-cycloalkyl in which optionally one or two not directly adjacent ring members are replaced by oxygen and/or sulphur or represents in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl or naphthyl, hetaryl having 5 to 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, B preferably represents hydrogen, $C_1$-$C_2$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen or phenyl or A, B and the carbon atom to which they are attached preferably represent $C_3$-$C_6$-cycloalkyl which is substituted by an alkylenedithioyl or by an alkylenedioxyl or by an alkylenediyl group which optionally contains one or two not directly adjacent oxygen and/or sulphur atoms and which is optionally substituted by $C_1$-$C_4$-alkyl, which, together with the carbon atom to which it is attached, forms a further five- to eight-membered ring or A, B and the carbon atom to which they are attached preferably represent $C_3$-$C_8$-cycloalkyl or $C_5$-$C_8$-cycloalkenyl in which two substituents together with the carbon atoms to which they are attached represent in each case optionally $C_1$-$C_6$-alkyl-, $C_1$-$C_6$-alkoxy- or halogen-substituted $C_2$-$C_6$-alkanediyl, $C_2$-$C_6$-alkenediyl or $C_4$-$C_6$-alkanedienediyl in which optionally one methylene group is replaced by oxygen or sulphur, D preferably represents hydrogen, in each case optionally halogen-substituted $C_1$-$C_{12}$-alkyl, $C_3$-$C_8$-alkenyl, $C_3$-$C_8$-alkynyl, $C_1$-$C_{10}$-alkoxy-$C_2$-$C_8$-alkyl, optionally halogen-, $C_1$-$C_4$-alkyl-, $C_1$-$C_4$-alkoxy- or $C_1$-$C_4$-haloalkyl-substituted $C_3$-$C_8$-cycloalkyl in which optionally one ring member is replaced by oxygen or sulphur or in each case optionally halogen-, $C_1$-$C_6$-alkyl-, $C_1$-$C_6$-haloalkyl-, $C_1$-$C_6$-alkoxy-, $C_1$-$C_6$-haloalkoxy-, cyano- or nitro-substituted phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl), or A and D together preferably represent in each case optionally substituted $C_3$-$C_6$-alkanediyl or $C_3$-$C_6$-alkenediyl in which optionally (only in the case of CKE=(1)) one methylene group is replaced by a carbonyl group, oxygen or sulphur, possible substituents being in each case:

halogen, hydroxyl, mercapto or in each case optionally halogen-substituted $C_1$-$C_{10}$-alkyl, $C_1$-$C_6$-alkoxy, $C_1$-$C_6$-alkylthio, $C_3$-$C_7$-cycloalkyl, phenyl or benzyloxy, or a further $C_3$-$C_6$-alkanediyl grouping, $C_3$-$C_6$-alkenediyl grouping or a butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D together with the atoms to which they are attached then represent, for example, the groups AD-1 to AD-10 mentioned below) which may contain oxygen or sulphur, or which optionally contains one of the following groups

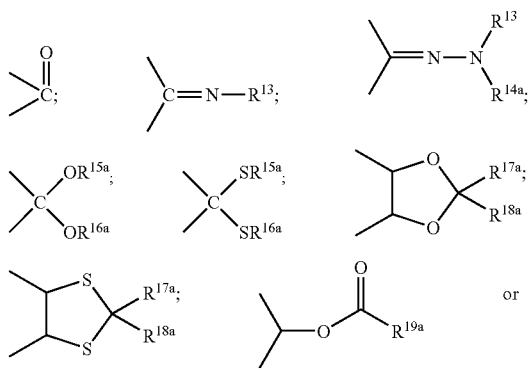

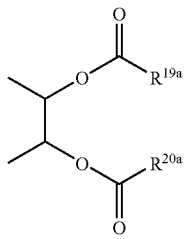

or

A and $Q^1$ together preferably represent $C_3$-$C_6$-alkanediyl or $C_4$-$C_6$-alkenediyl, each of which is optionally mono- or disubstituted by identical or different substituents from the group consisting of halogen, hydroxyl, of $C_1$-$C_{10}$-alkyl, $C_1$-$C_6$-alkoxy, $C_1$-$C_6$-alkylthio; $C_3$-$C_7$-cycloalkyl each of which is optionally mono- to trisubstituted by identical or different halogen, and of benzyloxy and phenyl, each of which is optionally mono- to trisubstituted by identical or different substituents from the group consisting of halogen, $C_1$-$C_6$-alkyl and $C_1$-$C_6$-alkoxy, which $C_3$-$C_6$-alkanediyl or $C_4$-$C_6$-alkenediyl moreover optionally contains one of the groups below

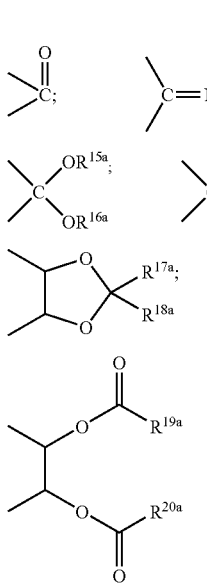

or is bridged by a $C_1$-$C_2$-alkanediyl group or by an oxygen atom or $Q^1$ preferably represents hydrogen or $C_1$-$C_4$-alkyl, $Q^2$, $Q^4$, $Q^5$ and $Q^6$ independently of one another preferably represent hydrogen or $C_1$-$C_4$-alkyl, $Q^3$ preferably represents hydrogen, $C_1$-$C_6$-alkyl, $C_1$-$C_6$-alkoxy-$C_1$-$C_2$-alkyl, $C_1$-$C_6$-alkylthio-$C_1$-$C_2$-alkyl, optionally $C_1$-$C_4$-alkyl- or $C_1$-$C_4$-alkoxy-substituted $C_3$-$C_8$-cycloalkyl in which optionally one methylene group is replaced by oxygen or sulphur or represents phenyl which is optionally substituted by halogen, $C_1$-$C_4$-alkyl, $C_1$-$C_4$-alkoxy, $C_1$-$C_2$-haloalkyl, $C_1$-$C_2$-haloalkoxy, cyano or nitro, or $Q^3$ and $Q^4$ together with the carbon atom to which they are attached preferably represent a $C_3$-$C_7$-ring which is optionally substituted by $C_1$-$C_4$-alkyl, $C_1$-$C_4$-alkoxy or $C_1$-$C_2$-haloalkyl and in which optionally one ring member is replaced by oxygen or sulphur, G preferably represents hydrogen (a) or represents one of the groups (b)

(c)
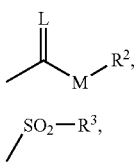

(d)
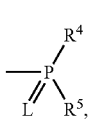

(e)
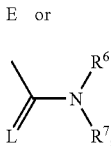

(f)
E or (g)

in particular (a), (b), (c) or (g),
in which
E represents a metal ion equivalent or an ammonium ion,
L represents oxygen or sulphur and
M represents oxygen or sulphur, $R^1$ preferably represents in each case optionally halogen-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl or optionally halogen-, $C_1$-$C_6$-alkyl- or $C_1$-$C_6$-alkoxy-substituted $C_3$-$C_8$-cycloalkyl in which optionally one or more (preferably not more than two) not directly adjacent ring members are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl (for example pyrazolyl, thiazolyl, pyridyl, pyrimidyl, furanyl or thienyl), represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents in each case optionally halogen-substituted $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, R³ preferably represents optionally halogen-substituted C₁-C₈-alkyl or represents in each case optionally halogen-, C₁-C₆-alkyl-, C₁-C₆-alkoxy-, C₁-C₄-haloalkyl-, C₁-C₄-haloalkoxy-, cyano- or nitro-substituted phenyl or benzyl, R⁴ and R⁵ independently of one another preferably represent in each case optionally halogen-substituted C₁-C₈-alkyl, C₁-C₈-alkoxy, C₁-C₈-alkylamino, di-(C₁-C₈-alkyl)amino, C₁-C₈-alkylthio, C₂-C₈-alkenylthio, C₃-C₇-cycloalkylthio or represent in each case optionally halogen-, nitro-, cyano-, C₁-C₄-alkoxy-, C₁-C₄-haloalkoxy-, C₁-C₄-alkylthio-, C₁-C₄-haloalkylthio-, C₁-C₄-alkyl- or C₁-C₄-haloalkyl-substituted phenyl, phenoxy or phenylthio, R⁶ and R⁷ independently of one another preferably represent hydrogen, represent in each case optionally halogen-substituted C₁-C₈-alkyl, C₃-C₈-cycloalkyl, C₁-C₈-alkoxy, C₃-C₈-alkenyl, C₁-C₈-alkoxy-C₁-C₈-alkyl, represent optionally halogen-, C₁-C₈-haloalkyl-, C₁-C₈-alkyl- or C₁-C₈-alkoxy-substituted phenyl, represent optionally halogen-, C₁-C₈-alkyl-, C₁-C₈-haloalkyl- or C₁-C₈-alkoxy-substituted benzyl or together represent an optionally C₁-C₄-alkyl-substituted C₃-C₆-alkylene radical in which optionally one carbon atom is replaced by oxygen or sulphur, R¹³ preferably represents hydrogen, represents in each case optionally halogen-substituted C₁-C₈-alkyl or C₁-C₈-alkoxy, represents optionally halogen-, C₁-C₄-alkyl- or C₁-C₄-alkoxy-substituted C₃-C₈-cycloalkyl in which optionally one methylene group is replaced by oxygen or sulphur or represents in each case optionally halogen-, C₁-C₆-alkyl-, C₁-C₆-alkoxy-, C₁-C₄-haloalkyl-, C₁-C₄-haloalkoxy-, nitro- or cyano-substituted phenyl, phenyl-C₁-C₄-alkyl or phenyl-C₁-C₄-alkoxy, R¹⁴ᵃ preferably represents hydrogen or C₁-C₈-alkyl, or R¹³ and R¹⁴ᵃ together preferably represent C₄-C₆-alkanediyl, R¹⁵ᵃ and R¹⁶ᵃ are identical or different and preferably represent C₁-C₆-alkyl, or R¹⁵ᵃ and R¹⁶ᵃ together preferably represent a C₂-C₄-alkanediyl radical which is optionally substituted by C₁-C₆-alkyl, C₁-C₆-haloalkyl or by optionally halogen-, C₁-C₆-alkyl-, C₁-C₄-haloalkyl-, C₁-C₆-alkoxy-, C₁-C₄-haloalkoxy-, nitro- or cyano-substituted phenyl, R¹⁷ᵃ and R¹⁸ᵃ independently of one another preferably represent hydrogen, represent optionally halogen-substituted C₁-C₈-alkyl or represent optionally halogen-, C₁-C₆-alkyl-, C₁-C₆-alkoxy-, C₁-C₄-haloalkyl-, C₁-C₄-haloalkoxy-, nitro- or cyano-substituted phenyl, or R¹⁷ᵃ and R¹⁸ᵃ together with the carbon atom to which they are attached preferably represent a carbonyl group or represent optionally halogen-, C₁-C₄-alkyl- or C₁-C₄-alkoxy-substituted C₅-C₇-cycloalkyl in which optionally one methylene group is replaced by oxygen or sulphur, R¹⁹ᵃ and R²⁰ᵃ independently of one another preferably represent C₁-C₁₀-alkyl, C₂-C₁₀-alkenyl, C₁-C₁₀-alkoxy, C₁-C₁₀-alkylamino, C₃-C₁₀-alkenylamino, di-(C₁-C₁₀-alkyl)amino or di-(C₃-C₁₀-alkenyl)amino.

In the radical definitions mentioned as being preferred, halogen represents fluorine, chlorine, bromine and iodine, in particular fluorine, chlorine and bromine.

W particularly preferably represents C₁-C₄-alkoxy, C₁-C₄-haloalkoxy, C₁-C₃-alkoxy-C₂-C₃-alkoxy, C₁-C₂-alkoxy-bis-C₂-C₃-alkoxy or C₃-C₆-cycloalkyl-C₁-C₂-alkanediyloxy in which optionally one methylene group of the ring may be replaced by oxygen, X particularly preferably represents chlorine or bromine, Y particularly preferably represents methyl, ethyl or propyl, CKE particularly preferably represents one of the groups

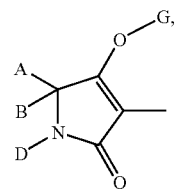

(1)

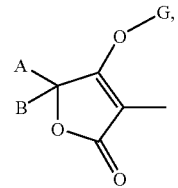

(2)

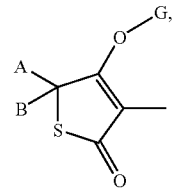

(3)

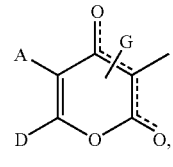

(4)

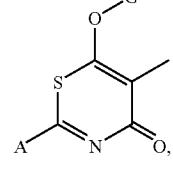

(5)

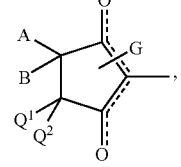

(6)

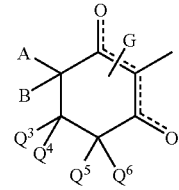

(7)

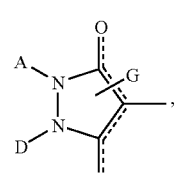

(8)

A particularly preferably represents hydrogen, represents C₁-C₆-alkyl or C₁-C₄-alkoxy-C₁-C₂-alkyl, each of which is optionally mono- to trisubstituted by fluorine or chlorine, represents $C_3$-$C_6$-cycloalkyl which is optionally mono- to disubstituted by $C_1$-$C_2$-alkyl or $C_1$-$C_2$-alkoxy or (but not in the case of the compounds of the formulae (I-3), (I-4), (I-6) and (I-7)) represents phenyl or benzyl, each of which is optionally mono- to disubstituted by fluorine, chlorine, bromine, $C_1$-$C_4$-alkyl, $C_1$-$C_2$-haloalkyl, $C_1$-$C_4$-alkoxy or $C_1$-$C_2$-haloalkoxy, cyano or nitro, B particularly preferably represents hydrogen, $C_1$-$C_4$-alkyl or $C_1$-$C_2$-alkoxy-$C_1$-$C_2$-alkyl, or A, B and the carbon atom to which they are attached particularly preferably represent saturated or unsaturated $C_5$-$C_7$-cycloalkyl in which optionally one ring member is replaced by oxygen or sulphur and which is optionally mono- to disubstituted by $C_1$-$C_6$-alkyl, trifluoromethyl or $C_1$-$C_6$-alkoxy, with the proviso that in this case $Q^3$ particularly preferably represents hydrogen or methyl, or A, B and the carbon atom to which they are attached particularly preferably represent $C_5$-$C_6$-cycloalkyl which is substituted by an alkylenedithiol group or by an alkylenedioxyl group or by an alkylenediyl group which optionally contains one or two not directly adjacent oxygen or sulphur atoms and which is optionally substituted by methyl or ethyl, which group, together with the carbon atom to which it is attached, forms a further five- or six-membered ring, with the proviso that in this case $Q^3$ particularly preferably represents hydrogen or methyl, A, B and the carbon atom to which they are attached particularly preferably represent $C_3$-$C_6$-cycloalkyl or $C_5$-$C_6$-cycloalkenyl in which two substituents together with the carbon atoms to which they are attached represent in each case optionally $C_1$-$C_2$-alkyl- or $C_1$-$C_2$-alkoxy-substituted $C_2$-$C_4$-alkanediyl, $C_2$-$C_4$-alkenediyl or butadienediyl, with the proviso that in this case $Q^3$ particularly preferably represents hydrogen or methyl, D particularly preferably represents hydrogen, represents $C_1$-$C_6$-alkyl, $C_3$-$C_6$-alkenyl or $C_1$-$C_4$-alkoxy-$C_2$-$C_3$-alkyl, each of which is optionally mono- to trisubstituted by fluorine, represents $C_3$-$C_6$-cycloalkyl which is optionally mono- to disubstituted by $C_1$-$C_4$-alkyl, $C_1$-$C_4$-alkoxy or $C_1$-$C_2$-haloalkyl and in which optionally one methylene group is replaced by oxygen or (but not in the case of the compounds of the formula (I-1)) represents phenyl or pyridyl, each of which is optionally mono- to disubstituted by fluorine, chlorine, bromine, $C_1$-$C_4$-alkyl, $C_1$-$C_4$-haloalkyl, $C_1$-$C_4$-alkoxy or $C_1$-$C_4$-haloalkoxy, or A and D together particularly preferably represent optionally mono- to disubstituted $C_3$-$C_5$-alkanediyl in which optionally (only in the case of CKE=(1)) one methylene group may be replaced by oxygen or sulphur, possible substituents being $C_1$-$C_2$-alkyl or $C_1$-$C_2$-alkoxy, or A and D (in the case of the compounds of the formula (I-1)) together with the atoms to which they are attached particularly preferably represent one of the groups AD-1 to AD-10:

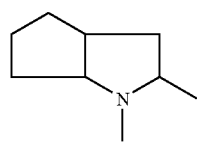 AD-1

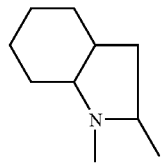 AD-2

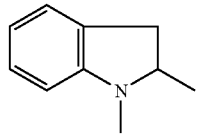 AD-3

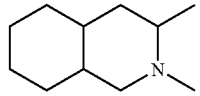 AD-4

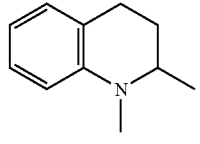 AD-5

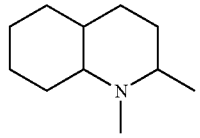 AD-6

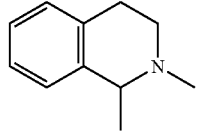 AD-7

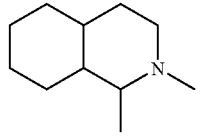 AD-8

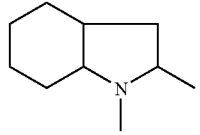 AD-9

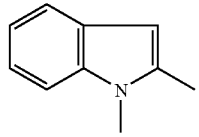 AD-10 or

A and $Q^1$ together particularly preferably represent $C_3$-$C_4$-alkanediyl which is optionally mono- or disubstituted by identical or different substituents from the group consisting of $C_1$-$C_2$-alkyl and $C_1$-$C_2$-alkoxy or $Q^1$ particularly preferably represents hydrogen, $Q^2$ particularly preferably represents hydrogen, $Q^4$, $Q^5$ and $Q^6$ independently of one another particularly preferably represent hydrogen or $C_1$-$C_3$-alkyl, $Q^3$ particularly preferably represents hydrogen, $C_1$-$C_4$-alkyl or $C_3$-$C_6$-cycloalkyl which is optionally mono- to disubstituted by methyl or methoxy, or Q³ and Q⁴ together with the carbon to which they are attached particularly preferably represent a saturated $C_5$-$C_6$-ring which is optionally substituted by $C_1$-$C_2$-alkyl or $C_1$-$C_2$-alkoxy and in which optionally one ring member is replaced by oxygen or sulphur, with the proviso that in this case A particularly preferably represents hydrogen or methyl, or G particularly preferably represents hydrogen (a) or represents one of the groups

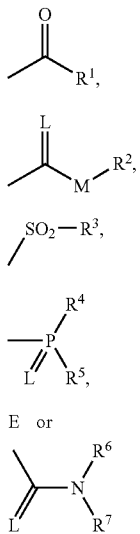

in particular (a), (b) or (c),
in which
E represents a metal ion equivalent or an ammonium ion,
L represents oxygen or sulphur and
M represents oxygen or sulphur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or $C_3$-$C_6$-cycloalkyl which is optionally mono- to disubstituted by fluorine, chlorine, $C_1$-$C_2$-alkyl or $C_1$-$C_2$-alkoxy and in which optionally one or two not directly adjacent ring members are replaced by oxygen,
represents phenyl which is optionally mono- to disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine,
represents $C_3$-$C_6$-cycloalkyl which is optionally monosubstituted by $C_1$-$C_2$-alkyl or $C_1$-$C_2$-alkoxy or
represents phenyl or benzyl, each of which is optionally mono- to disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine or represents phenyl which is optionally monosubstituted by fluorine, chlorine, bromine, $C_1$-$C_4$-alkyl, $C_1$-$C_4$-alkoxy, trifluoromethyl, trifluoromethoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio or represents phenyl, phenoxy or phenylthio, each of which is optionally monosubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, represents phenyl which is optionally monosubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent a $C_4$-$C_5$-alkylene radical which is optionally substituted by methyl or ethyl and in which optionally one methylene group is replaced by oxygen or sulphur.

In the radical definitions mentioned as being particularly preferred, halogen represents fluorine, chlorine and bromine, in particular fluorine and chlorine.

W very particularly preferably represents methoxy, ethoxy, n-propoxy, isopropoxy, n-butoxy, isobutoxy, sec-butoxy, methoxyethoxy, ethoxyethoxy, cyclopropylmethoxy, cyclopentyl-methoxy or cyclohexylmethoxy, X very particularly preferably represents chlorine or bromine, Y very particularly preferably represents methyl or ethyl, CKE very particularly preferably represents one of the groups

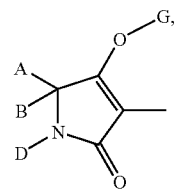

(1)

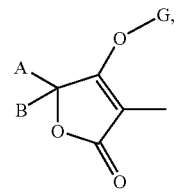

(2)

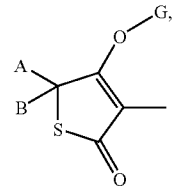

(3)

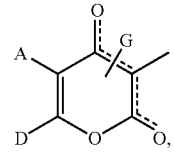

(4)

-continued (5)

[Structure with A-S-C(=N)-C(=O) ring system with OG substituent]

(6)

[Cyclopentane-dione structure with A, B, Q¹, Q² substituents and G group]

(7)

[Cyclohexane-dione structure with A, B, Q³, Q⁴, Q⁵, Q⁶ substituents and G group]

(8)

[Pyrazoline-dione structure with A, D on N atoms and G group]

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl and (only in the case of the compounds of the formula (I-5)) represents phenyl which is optionally monosubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl or ethyl, or A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy or butoxy, with the proviso that in this case $Q^3$ very particularly preferably represents hydrogen, or A, B and the carbon atom to which they are attached very particularly preferably represent $C_6$-cycloalkyl which is substituted by an alkylenedioxyl group having two not directly adjacent oxygen atoms, with the proviso that in this case $Q^3$ very particularly preferably represents hydrogen, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, with the proviso that in this case $Q^3$ very particularly preferably represents hydrogen, D very particularly preferably represents hydrogen, represents $C_1$-$C_4$-alkyl, $C_3$-$C_4$-alkenyl or $C_1$-$C_4$-alkoxy-$C_2$-$C_3$-alkyl, each of which is optionally mono- to trisubstituted by fluorine, represents cyclopropyl, cyclopentyl or cyclohexyl or (but not in the case of the compounds of the formula (I-1)) represents phenyl or pyridyl, each of which is optionally monosubstituted by fluorine, chlorine, methyl, ethyl, n-propyl, isopropyl, methoxy, ethoxy or trifluoromethyl, or A and D together very particularly preferably represent $C_3$-$C_5$-alkanediyl which is optionally monosubstituted by methyl or methoxy and in which optionally (only in the case of CKE=(1)) one carbon atom is replaced by oxygen or sulphur, or represents the group AD-1, A and $Q^1$ together very particularly preferably represent $C_3$-$C_4$-alkanediyl which is optionally mono- or disubstituted by methyl or methoxy, or $Q^1$ very particularly preferably represents hydrogen, $Q^2$ very particularly preferably represents hydrogen, $Q^4$, $Q^5$ and $Q^6$ independently of one another very particularly preferably represent hydrogen or methyl, $Q^3$ very particularly preferably represents hydrogen, methyl, ethyl or propyl, or $Q^3$ and $Q^4$ together with the carbon to which they are attached very particularly preferably represent a saturated $C_5$-$C_6$-ring which is optionally monosubstituted by methyl or methoxy, with the proviso that in this case A very particularly preferably represents hydrogen, G very particularly preferably represents hydrogen (a) or represents one of the groups (b)

[Structure: C(=O)R¹]

(c)

[Structure: C(=L)-M-R²]

(d)

[Structure: SO₂-R³] or (f)

E in which

E represents an ammonium ion,

L represents oxygen or sulphur and

M represents oxygen or sulphur, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl or represents $C_3$-$C_6$-cyclopropyl which is optionally monosubstituted by fluorine, chlorine, methyl or methoxy or represents $C_1$-$C_4$-alkyl which is monosubstituted by chlorine, represents phenyl which is optionally monosubstituted by fluorine, chlorine, bromine, cyano, nitro, methyl, methoxy, trifluoromethyl or trifluoromethoxy, $R^2$ very particularly preferably represents phenyl or benzyl, $C_1$-$C_8$-alkyl, $C_2$-$C_6$-alkenyl or $C_1$-$C_4$-alkoxy-$C_2$-$C_3$-alkyl, each of which is optionally mono- to trisubstituted by fluorine, $R^3$ very particularly preferably represents $C_1$-$C_6$-alkyl.

W most preferably represents methoxy, ethoxy, n-propoxy, methoxyethoxy or cyclopropylmethoxy, X most preferably represents chlorine,
Y most preferably represents methyl,
CKE most preferably represents one of the groups

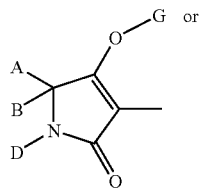
(1)

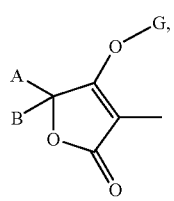
(2)

A most preferably represents methyl, isopropyl, isobutyl or cyclopropyl,
B most preferably represents hydrogen, methyl or ethyl, or
A, B and the carbon atom to which they are attached most preferably represent saturated $C_5$-$C_6$-cycloalkyl in which optionally one ring atom is replaced by oxygen and which is optionally monosubstituted by methyl or methoxy,
D most preferably represents hydrogen, methyl or ethyl,
G most preferably represents hydrogen (a) or represents one of the groups

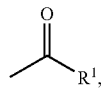
(b)

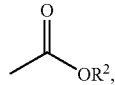
(c)

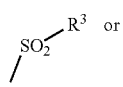
(d)

(E) (f)

E represents an ammonium ion,
$R^1$ most preferably represents $C_1$-$C_6$-alkyl, $C_1$-$C_2$-alkoxy-$C_1$-alkyl, $C_3$-$C_6$-cycloalkyl (especially cyclopropyl or cyclohexyl), $C_1$-$C_4$-alkyl which is monosubstituted by chlorine or represents phenyl which is optionally monosubstituted by chlorine,
$R^2$ most preferably represents $C_1$-$C_8$-alkyl, $C_3$-$C_6$-alkenyl or benzyl,
$R^3$ most preferably represents $C_1$-$C_6$-alkyl.

The general or preferred radical definitions or illustrations given above can be combined with one another as desired, i.e. including combinations between the respective ranges and preferred ranges. They apply both to the end products and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Saturated or unsaturated hydrocarbon radicals, such as alkyl, alkanediyl or alkenyl, can in each case be straight-chain or branched as far as this is possible, including in combination with heteroatoms, such as, for example, in alkoxy.

Optionally substituted radicals can, unless stated otherwise, be mono- or polysubstituted, wherein the case of polysubstitution the substituents can be identical or different.

In addition to the compounds mentioned in the Preparation Examples, the following compounds of the formula (I-1-a) may be specifically mentioned:

TABLE 1

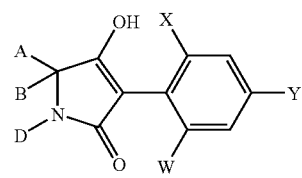

$W = OCH_3, X = Cl, Y = CH_3$.

| A | B | D |
|---|---|---|
| $CH_3$ | H | H |
| $C_2H_5$ | H | H |
| $C_3H_7$ | H | H |
| i-$C_3H_7$ | H | H |
| $C_4H_9$ | H | H |
| i-$C_4H_9$ | H | H |
| s-$C_4H_9$ | H | H |
| t-$C_4H_9$ | H | H |
| $CH_3$ | $CH_3$ | H |
| $C_2H_5$ | $CH_3$ | H |
| $C_3H_7$ | $CH_3$ | H |
| i-$C_3H_7$ | $CH_3$ | H |
| $C_4H_9$ | $CH_3$ | H |
| i-$C_4H_9$ | $CH_3$ | H |
| s-$C_4H_9$ | $CH_3$ | H |
| t-$C_4H_9$ | $CH_3$ | H |
| $C_2H_5$ | $C_2H_5$ | H |
| $C_3H_7$ | $C_3H_7$ | H |
| cyclopropyl | $CH_3$ | H |
| cyclopentylmethyl | $CH_3$ | H |
| cyclohexylmethyl | $CH_3$ | H |
| —$(CH_2)_2$— | | H |
| —$(CH_2)_4$— | | H |
| —$(CH_2)_5$— | | H |
| —$(CH_2)_6$— | | H |
| —$(CH_2)_7$— | | H |
| —$(CH_2)_2$—O—$(CH_2)_2$— | | H |
| —$CH_2$—O—$(CH_2)_3$— | | H |
| —$(CH_2)_2$—S—$(CH_2)_2$— | | H |

TABLE 1-continued

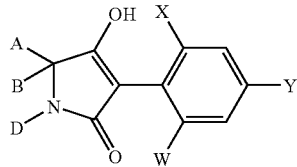

W = OCH₃, X = Cl, Y = CH₃.

| A | B | D |
|---|---|---|
| | —CH₂—CHCH₃—(CH₂)₃— | H |
| | —(CH₂)₂—CHCH₃—(CH₂)₂— | H |
| | —(CH₂)₂—CHC₂H₅—(CH₂)₂— | H |
| | —(CH₂)₂—CHC₃H₇—(CH₂)₂— | H |
| | —(CH₂)₂—CHi-C₃H₇—(CH₂)₂— | H |
| | —(CH₂)₂—CHOCH₃—(CH₂)₂— | H |
| | —(CH₂)₂—CHOC₂H₅—(CH₂)₂— | H |
| | —(CH₂)₂—CHOC₃H₇—(CH₂)₂— | H |
| | —(CH₂)₂—CHOi-C₃H₇—(CH₂)₂— | H |
| | —(CH₂)₂—C(CH₃)₂—(CH₂)₂— | H |
| | —CH₂—(CHCH₃)₂—(CH₂)₂— | H |
| | —CH₂—CH—(CH₂)₂—CH— with —CH₂— bridge | H |
| | —CH₂—CH—CH—CH₂— with (CH₂)₄ bridge | H |
| | —CH₂—CH—CH—(CH₂)₂— with (CH₂)₃ bridge | H |
| | indane-fused | H |
| | tetralin-fused | H |
| | —(CH₂)₃— | H |
| | —(CH₂)₄— | H |
| | —CH₂—CHCH₃—CH₂— | H |
| | —CH₂—CH₂—CHCH₃— | H |
| | —CH₂—S—CH₂— | H |
| | —CH₂—S—(CH₂)₂— | H |
| | —(CH₂)₂—S—CH₂— | H |
| | —CH₂—CH—CH— with (CH₂)₃ bridge | H |
| H | CH₃ | H |
| H | C₂H₅ | H |
| H | C₃H₇ | H |
| H | i-C₃H₇ | H |
| H | cyclopropyl | H |
| H | cyclopentyl | H |
| H | cyclohexyl | H |

TABLE 1-continued

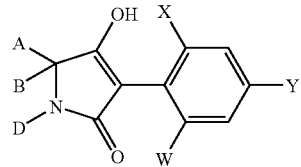

W = OCH₃, X = Cl, Y = CH₃.

| A | B | D |
|---|---|---|
| CH₃ | CH₃ | H |
| CH₃ | C₂H₅ | H |
| CH₃ | C₃H₇ | H |
| CH₃ | i-C₃H₇ | H |
| CH₃ | cyclopropyl | H |
| CH₃ | cyclopentyl | H |
| CH₃ | cyclohexyl | H |
| C₂H₅ | CH₃ | H |
| C₂H₅ | C₂H₅ | H |

Table 2: A, B and D are as shown in Table 1
W=OCH₃; X=Br; Y=CH₃

Table 3: A, B and D are as shown in Table 1
W=OC₂H₅; X=Cl; Y=CH₃.

Table 4: A, B and D are as shown in Table 1
W=OC₂H₅; X=Br; Y=CH₃.

In addition to the compounds mentioned in the Preparation Examples, the following compounds of the formula (I-2-a) may be specifically mentioned:

TABLE 5

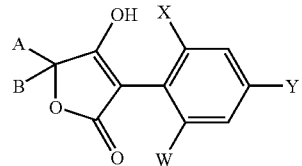

W = OCH₃, X = Cl, Y = CH₃.

| A | B |
|---|---|
| CH₃ | H |
| C₂H₅ | H |
| C₃H₇ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |

TABLE 5-continued

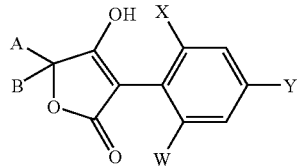

W = OCH₃, X = Cl, Y = CH₃.

| A | B |
|---|---|
| C₂H₅ | C₂H₅ |
| C₃H₇ | C₃H₇ |
| cyclopropyl | CH₃ |
| cyclopentyl | CH₃ |
| cyclohexyl | CH₃ |
| —(CH₂)₂— | |
| —(CH₂)₄— | |
| —(CH₂)₅— | |
| —(CH₂)₆— | |
| —(CH₂)₇— | |
| —(CH₂)₂—O—(CH₂)₂— | |
| —CH₂—O—(CH₂)₃— | |
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| —(CH₂)₂—S—(CH₂)₂— | |
| —CH₂—CHCH₃—(CH₂)₃— | |
| —(CH₂)₂—CHCH₃—(CH₂)₂— | |
| —(CH₂)₂—CHC₂H₅—(CH₂)₂— | |
| —(CH₂)₂—CHC₃H₇—(CH₂)₂— | |
| —(CH₂)₂—CHOi-C₃H₇—(CH₂)₂— | |
| —(CH₂)₂—CHOCH₃—(CH₂)₂— | |
| —(CH₂)₂—CHOC₂H₅—(CH₂)₂— | |
| —(CH₂)₂—CHOC₃H₇—(CH₂)₂— | |
| —(CH₂)₂—CHi-C₃H₇—(CH₂)₂— | |
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |

TABLE 5-continued

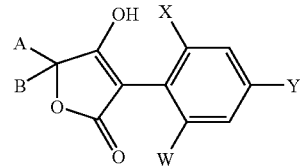

W = OCH₃, X = Cl, Y = CH₃.

| A | B |
|---|---|
| C₄H₉ | CH₃ |
| i-C₄H₉ | CH₃ |
| s-C₄H₉ | CH₃ |
| t-C₄H₉ | CH₃ |
| —(CH₂)₂—C(CH₃)₂—(CH₂)₂— | |
| —CH₂—(CHCH₃)₂—(CH₂)₂— | |
| —CH₂—CH—(CH₂)₂—CH— with bridging CH₂ | |
| —CH₂—CH—CH—CH₂— with (CH₂)₄ bridge | |
| —CH₂—CH—CH—(CH₂)₂— with (CH₂)₃ bridge | |
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| indanyl | |
| tetrahydronaphthyl | |

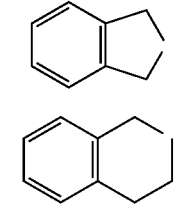

Table 6: A and B are as shown in Table 5
W=OCH₃; X=Br; Y=CH₃.

Table 7: A and B are as shown in Table 5
W=OC₂H₅; X=Cl; Y=CH₃.

Table 8: A and B are as shown in Table 5
W=OC₂H₅; X=Br; Y=CH₃.

Preferred meanings of the groups mentioned above in connection with the compounds improving crop plant tolerance ("herbicide safeners") of the formulae (IIa), (IIb), (IIc), (IId) and (IIe) are defined hereinbelow.

m preferably represents the numbers 0, 1, 2, 3 or 4.

A¹ preferably represents one of the divalent heterocyclic groups outlined hereinbelow

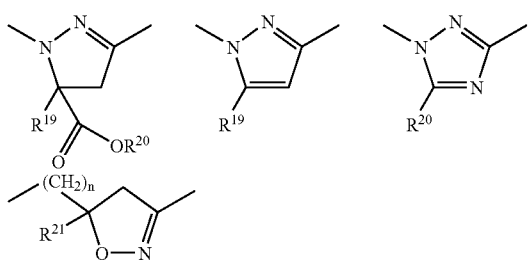

n preferably represents the numbers 0, 1, 2, 3 or 4.

$A^2$ preferably represents methylene or ethylene, each of which is optionally substituted by methyl, ethyl, methoxycarbonyl or ethoxycarbonyl.

$R^{14}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{15}$ preferably represents hydroxyl, mercapto, amino, methoxy, ethoxy, n- or i-propoxy, n-, i-, s- or t-butoxy, 1-methylhexyloxy, allyloxy, 1-allyloxymethylethoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{16}$ preferably represents methyl, ethyl, n- or i-propyl, each of which is optionally substituted by fluorine, chlorine and/or bromine.

$R^{17}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl.

$R^{18}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl, or $R^{17}$ and $R^{18}$ together also represent one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the carbon atom to which they are bonded, form a 5- or 6-membered carbocycle.

$R^{19}$ preferably represents hydrogen, cyano, fluorine, chlorine, bromine, or represents methyl, ethyl, n- or i-propyl, cyclopropyl, cyclobutyl, cyclopentyl, cyclohexyl or phenyl, each of which is optionally substituted by fluorine, chlorine and/or bromine.

$R^{20}$ preferably represents hydrogen, or represents methyl, ethyl, n- or i-propyl, n-, i-, s- or t-butyl, optionally substituted by hydroxyl, cyano, fluorine, chlorine, methoxy, ethoxy, n- or i-propoxy.

$R^{21}$ preferably represents hydrogen, cyano, fluorine, chlorine, bromine, or represents methyl, ethyl, n- or i-propyl, n-, i-, s- or t-butyl, cyclopropyl, cyclobutyl, cyclopentyl, cyclohexyl or phenyl, each of which is optionally substituted by fluorine, chlorine and/or bromine.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

t preferably represents the numbers 0, 1, 2, 3 or 4.

v preferably represents the numbers 0, 1, 2, 3 or 4.

$R^{22}$ preferably represents hydrogen, methyl, ethyl, n- or i-propyl.

$R^{23}$ preferably represents hydrogen, methyl, ethyl, n- or i-propyl.

$R^{24}$ preferably represents hydrogen, or represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, each of which is optionally substituted by cyano, fluorine, chlorine, methoxy, ethoxy, n- or i-propoxy, or represents cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, each of which is optionally substituted by cyano, fluorine, chlorine, bromine, methyl, ethyl, n- or i-propyl.

$R^{25}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl.

$R^{26}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl, or represents phenyl which is optionally substituted by nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, or together with $R^{25}$ represents butane-1,4-diyl(trimethylene), pentane-1,5-diyl, 1-oxabutane-1,4-diyl or 3-oxapentane-1,5-diyl, each of which is optionally substituted by methyl or ethyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table which follows.

TABLE

Examples of the compounds of the formula (IIa)

| Example No. | (Positions) $(X^1)_m$ | $A^1$ | $R^{14}$ |
|---|---|---|---|
| IIa-1 | (2) Cl, (4) Cl | [pyrazoline with H3C and C(O)OCH3] | OCH3 |
| IIa-2 | (2) Cl, (4) Cl | [pyrazoline with H3C and C(O)OC2H5] | OCH3 |
| IIa-3 | (2) Cl, (4) Cl | [pyrazoline with H3C and C(O)OCH3] | OC2H5 |
| IIa-4 | (2) Cl, (4) Cl | [pyrazoline with H3C and C(O)OC2H5] | OC2H5 |
| IIa-5 | (2) Cl | [pyrazole with phenyl] | OCH3 |
| IIa-6 | (2) Cl, (4) Cl | [pyrazole with phenyl] | OCH3 |
| IIa-7 | (2) F | [pyrazole with phenyl] | OCH3 |
| IIa-8 | (2) F | [pyrazole with 2-Cl-phenyl] | OCH3 |
| IIa-9 | (2) Cl, (4) Cl | [triazole with CCl3] | OC2H5 |
| IIa-10 | (2) Cl, (4) CF3 | [triazole with phenyl] | OCH3 |
| IIa-11 | (2) Cl | [pyrazole with 2-F-phenyl] | OCH3 |
| IIa-12 | — | [isoxazoline with phenyl] | OC2H5 |

TABLE-continued

Examples of the compounds of the formula (IIa)

(IIa)

$(X^1)_m$—[phenyl ring with positions 2,3,4]—$A^1$—C(=O)—$R^{14}$

| Example No. | (Positions) $(X^1)_m$ | $A^1$ | $R^{14}$ |
|---|---|---|---|
| IIa-13 | (2) Cl, (4) Cl | 1-methyl-3-methyl-pyrazol-5-yl (H₃C at 5-position) | $OC_2H_5$ |
| IIa-14 | (2) Cl, (4) Cl | 1-methyl-3-methyl-pyrazol-5-yl ($C_3H_7$-i at 5-position) | $OC_2H_5$ |
| IIa-15 | (2) Cl, (4) Cl | 1-methyl-3-methyl-pyrazol-5-yl ($C_4H_9$-t at 5-position) | $OC_2H_5$ |
| IIa-16 | (2) Cl, (4) Cl | 5-ethyl-3-methyl-4,5-dihydroisoxazol-5-yl (CH₂ linker) | $OC_2H_5$ |
| IIa-17 | (2) Cl, (4) Cl | 5-methyl-3-methyl-4,5-dihydroisoxazol-5-yl | $OC_2H_5$ |
| IIa-18 | — | 5-methyl-5-phenyl-3-methyl-4,5-dihydroisoxazol-5-yl | OH |

Examples of the compounds of the formula (IIb) which are very particularly preferred as herbicide safeners according to the invention are listed in the table which follows.

TABLE (IIb)

[Quinoline ring with $X^3$ at position 4, $X^2$ at position 5, and 8-O—$A^2$—C(=O)—$R^{15}$]

Examples of the compounds of the formula (IIb)

| Example No. | (Position) $X^2$ | (Position) $X^3$ | $A^2$ | $R^{15}$ |
|---|---|---|---|---|
| IIb-1 | (5) Cl | — | $CH_2$ | OH |
| IIb-2 | (5) Cl | — | $CH_2$ | $OCH_3$ |
| IIb-3 | (5) Cl | — | $CH_2$ | $OC_2H_5$ |
| IIb-4 | (5) Cl | — | $CH_2$ | $OC_3H_7$-n |
| IIb-5 | (5) Cl | — | $CH_2$ | $OC_3H_7$-i |
| IIb-6 | (5) Cl | — | $CH_2$ | $OC_4H_9$-n |
| IIb-7 | (5) Cl | — | $CH_2$ | $OCH(CH_3)C_5H_{11}$-n |
| IIb-8 | (5) Cl | (2) F | $CH_2$ | OH |
| IIb-9 | (5) Cl | (2) Cl | $CH_2$ | OH |
| IIb-10 | (5) Cl | — | $CH_2$ | $OCH_2CH=CH_2$ |
| IIb-11 | (5) Cl | — | $CH_2$ | $OC_4H_9$-i |
| IIb-12 | (5) Cl | — | $CH_2$ | $OCH(CH_3)CH_2OCH_2CH=CH_2$ |
| IIb-13 | (5) Cl | — | $CH(CH_3)$ | $CH_2OCH_2CH=CH_2$ (with allyloxy group) |
| IIb-14 | (5) Cl | — | $CH(C_2H_5)$ | $OC_2H_5$ |
| IIb-15 | (5) Cl | — | $CH(CH_3)$ | $OCH_3$ |

Examples of the compounds of the formula (IIc) which are very particularly preferred as herbicide safeners according to the invention are listed in the table which follows.

TABLE

Examples of the compounds of the formula (IIc)

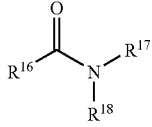

| Example No. | R^16 | N(R^17, R^18) |
|---|---|---|
| IIc-1 | $CHCl_2$ | $N(CH_2CH=CH_2)_2$ |
| IIc-2 | $CHCl_2$ | 2,2-dimethyl-3-methyl-oxazolidine |
| IIc-3 | $CHCl_2$ | 2,2,5-trimethyl-3-methyl-oxazolidine |
| IIc-4 | $CHCl_2$ | spiro cyclohexane oxazolidine |
| IIc-5 | $CHCl_2$ | 2,2-dimethyl-5-phenyl-3-methyl-oxazolidine |
| IIc-6 | $CHCl_2$ | 3,4-dimethyl-benzoxazine |
| IIc-7 | $CHCl_2$ | 2,2-dimethyl-5-(2-furyl)-3-methyl-oxazolidine |

Examples of the compounds of the formula (IId) which are very particularly preferred as herbicide safeners according to the invention are listed in the table which follows.

TABLE 5

Examples of the compounds of the formula (IId)

(IId)

| Example No. | $R^{22}$ | $R^{23}$ | $R^{24}$ | (Positions) $(X^4)_t$ | (Positions) $(X^5)_v$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ (5) $CH_3$ | — |
| IId-7 | H | H | $C_2H_5$ | (2) $OCH_3$ (5) $CH_3$ | — |
| IId-8 | H | H | $C_3H_7$-n | (2) $OCH_3$ (5) $CH_3$ | — |
| IId-9 | H | H | $C_3H_7$-i | (2) $OCH_3$ (5) $CH_3$ | — |
| IId-10 | H | H | cyclopropyl | (2) $OCH_3$ (5) $CH_3$ | — |
| IId-11 | H | H | $OCH_3$ | (2) $OCH_3$ (5) $CH_3$ | — |
| IId-12 | H | H | $OC_2H_5$ | (2) $OCH_3$ (5) $CH_3$ | — |
| IId-13 | H | H | $OC_3H_7$-i | (2) $OCH_3$ (5) $CH_3$ | — |
| IId-14 | H | H | $SCH_3$ | (2) $OCH_3$ (5) $CH_3$ | — |
| IId-15 | H | H | $SC_2H_5$ | (2) $OCH_3$ (5) $CH_3$ | — |
| IId-16 | H | H | $SC_3H_7$-i | (2) $OCH_3$ (5) $CH_3$ | — |
| IId-17 | H | H | $NHCH_3$ | (2) $OCH_3$ (5) $CH_3$ | — |
| IId-18 | H | H | $NHC_2H_5$ | (2) $OCH_3$ (5) $CH_3$ | — |
| IId-19 | H | H | $NHC_3H_7$-i | (2) $OCH_3$ (5) $CH_3$ | — |
| IId-20 | H | H | N-methyl-cyclopropylamino | (2) $OCH_3$ (5) $CH_3$ | — |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2-O-CH_3$ | (2) $OCH_3$ | — |

Examples of the compounds of the formula (IIe) which are very particularly preferred as herbicide safeners according to the invention are listed in the table which follows.

TABLE (IIe)

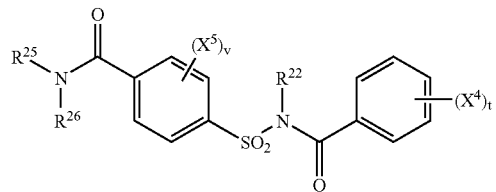

Examples of the compounds of the formuls (IIe)

| Example No. | $R^{22}$ | $R^{25}$ | $R^{26}$ | (Positions) $(X^4)_t$ | (Positions) $(X^5)_v$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | ▲ | (2) $OCH_3$ | — |
| IIe-6 | H | $CH_3$ | $CH_3$ | (2) $OCH_3$ | — |
| IIe-7 | H | H | $CH_3$ | (2) $OCH_3$ (5) $CH_3$ | — |
| IIe-8 | H | H | $C_2H_5$ | (2) $OCH_3$ (5) $CH_3$ | — |
| IIe-9 | H | H | $C_3H_7$-n | (2) $OCH_3$ (5) $CH_3$ | — |
| IIe-10 | H | H | $C_3H_7$-i | (2) $OCH_3$ (5) $CH_3$ | — |
| IIe-11 | H | H | ▲ | (2) $OCH_3$ (5) $CH_3$ | — |
| IIe-12 | H | $CH_3$ | $CH_3$ | (2) $OCH_3$ (5) $CH_3$ | — |

Cloquintocet-mexyl, fenchlorazol-ethyl, isoxadifen-ethyl, mefenpyr-diethyl, furilazole, fenclorim, cumyluron, dymron, dimepiperate and the compounds IIe-5 and IIe-11 are most preferred as the compound which improves crop plant tolerance [component (b')], with cloquintocet-mexyl and mefenpyr-diethyl being especially preferred.

Examples of the selectively herbicidal combinations according to the invention of in each case one active compound of the formula (I) and in each case one of the above-defined safeners are listed in the table which follows.

TABLE

Examples of the combinations according to the invention

| Active compounds of the formula (I) | Safener |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-2 | cloquintocet-mexyl |
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-2 | IIe-5 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-7 | cloquintocet-mexyl |
| I-7 | fenchlorazole-ethyl |
| I-7 | isoxadifen-ethyl |
| I-7 | mefenpyr-diethyl |
| I-7 | furilazole |
| I-7 | fenclorim |
| I-7 | cumyluron |
| I-7 | daimuron/dymron |
| I-7 | dimepiperate |
| I-7 | IIe-5 |
| I-7 | IIe-11 |
| I-8 | cloquintocet-mexyl |
| I-8 | fenchlorazole-ethyl |
| I-8 | isoxadifen-ethyl |
| I-8 | mefenpyr-diethyl |
| I-8 | furilazole |
| I-8 | fenclorim |
| I-8 | cumyluron |
| I-8 | daimuron/dymron |
| I-8 | dimepiperate |
| I-8 | IIe-5 |
| I-8 | IIe-11 |

The compounds of the general formula (IIa) to be used according to the invention as safener are known and/or can be prepared by methods known per se (cf. WO-A-91/07874, WO-A-95/07897).

The compounds of the general formula (IIb) to be used according to the invention as safener are known and/or can be prepared by methods known per se (cf. EP-A-191736).

The compounds of the general formula (IIc) to be used according to the invention as safener are known and/or can be prepared by methods known per se (cf. DE-A-2218097, DE-A-2350547).

The compounds of the general formula (IId) to be used according to the invention as safener are known and/or can be prepared by methods known per se (cf. DE-A-19621522/U.S. Pat. No. 6,235,680).

The compounds of the general formula (IIe) to be used according to the invention as safener are known and/or can be prepared by methods known per se (cf. WO-A-99/66795/U.S. Pat. No. 6,251,827).

Surprisingly, it has now been found that the above-defined active compound combinations of substituted ketoenols of the general formula (I) and safeners (antidotes) from the above group (b') are not only very well tolerated by useful plants, but also have a particularly high herbicidal activity and can be used in a variety of crops, in particular in cereals (mainly wheat), but also in soybeans, potatoes, maize and rice, for the selective control of weeds.

It must be considered as surprising that, from a multiplicity of known safeners or antidotes which are capable of antagonizing the damaging effect of a herbicide on the crop plants, it is precisely the abovementioned compounds of group (b') which are capable of virtually completely compensating for the harmful effect of substituted cyclic ketoenols of the formula (I) on the crop plants without adversely affecting the herbicidal activity towards the weeds to a substantial degree.

What must be emphasized in this context is the particularly advantageous activity of the particularly and most preferred combination partners from group (b'), in particular with regard to leaving cereal plants, such as, for example, wheat, barley and rye, but also maize and rice, as crop plants unharmed.

The active compound combinations according to the invention can be used, for example, in the following plants:

Using, for example, according to process (A), ethyl N-(2-chloro-4-methyl-6-methoxyphenyl-acetyl)-1-aminocyclohexanecarboxylate as starting material, the course of the process according to the invention can be represented by the reaction scheme below:

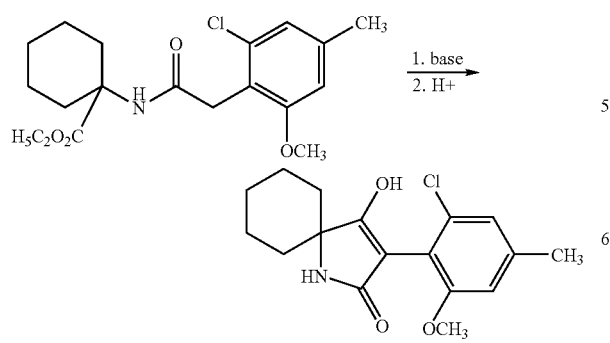

Using, for example, according to process (B), ethyl O-(2-chloro-4-methyl-6-methoxyphenylacetyl)-2-hydroxyisobutyrate, the course of the process according to the invention can be represented by the reaction scheme below:

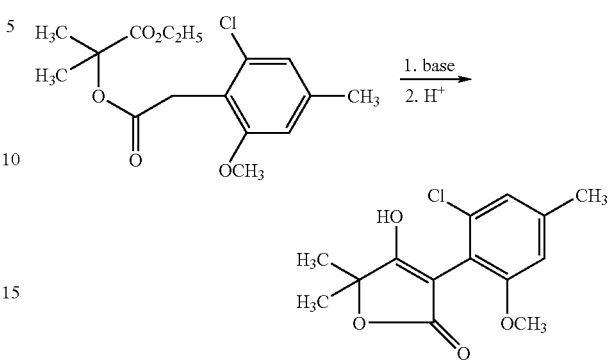

Using, for example, according to process (C), ethyl 2-(2-chloro-4-methyl-6-methoxyphenyl)-4-(4-methoxy)benzylmercapto-4-methyl-3-oxovalerate, the course of the process according to the invention can be represented by the reaction scheme below:

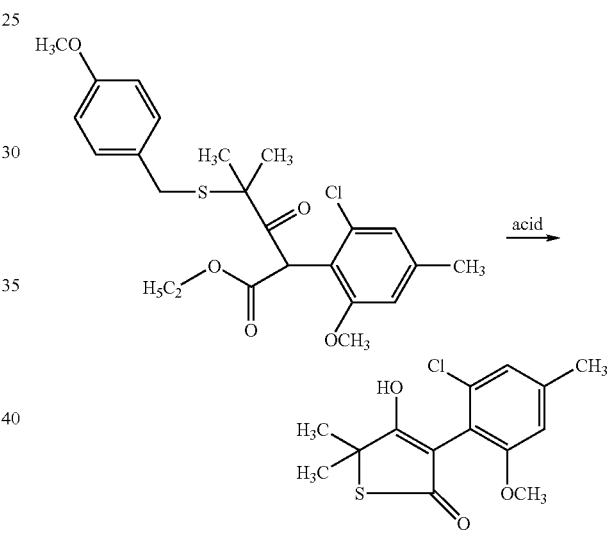

Using, for example, according to process (D), chlorocarbonyl 2-chloro-4-methyl-6-methoxyphenyl) ketene and acetone as starting materials, the course of the process according to the invention can be represented by the reaction scheme below:

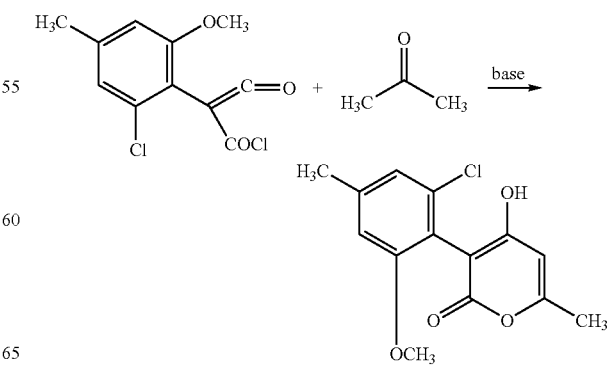

Using, for example, according to process (E), chlorocarbonyl 2-(2-chloro-4-methyl-6-methoxyphenyl)ketene and thiobenzamide as starting materials, the course of the process according to the invention can be represented by the reaction scheme below:

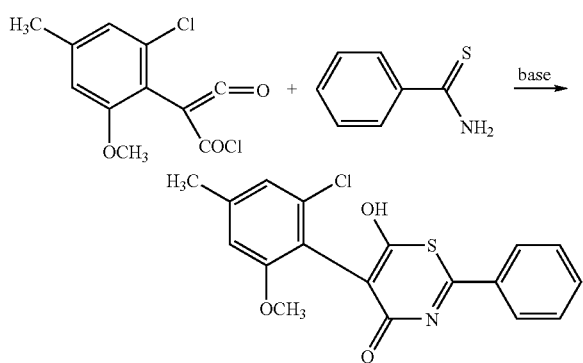

Using, for example, according to process (F), ethyl 5-(2-chloro-4-methyl-6-methoxyphenyl)-2,3-tetramethylene-4-oxovalerate, the course of the process according to the invention can be represented by the reaction scheme below:

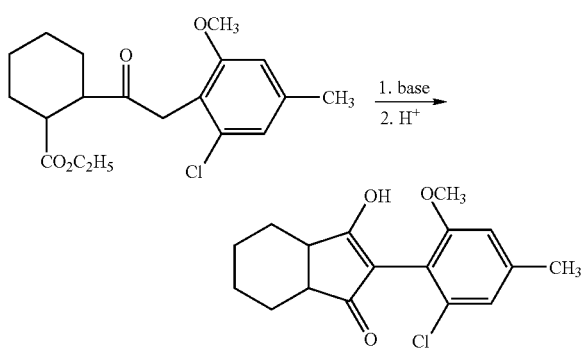

Using, for example, according to process (G), ethyl 5-[(2-chloro-4-methyl-6-methoxy)phenyl]-2,2-dimethyl-5-oxohexanoate, the course of the process according to the invention can be represented by the reaction scheme below:

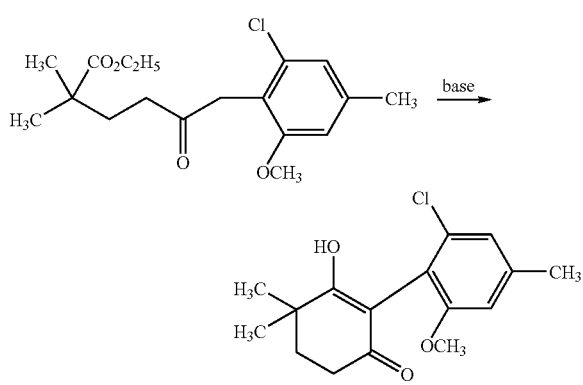

Using, for example, according to process (Hα), hexahydropyridazine and chlorocarbonyl 2-chloro-4-methyl-6-methoxyphenyl] ketene as starting materials, the course of the process according to the invention can be represented by the reaction scheme below:

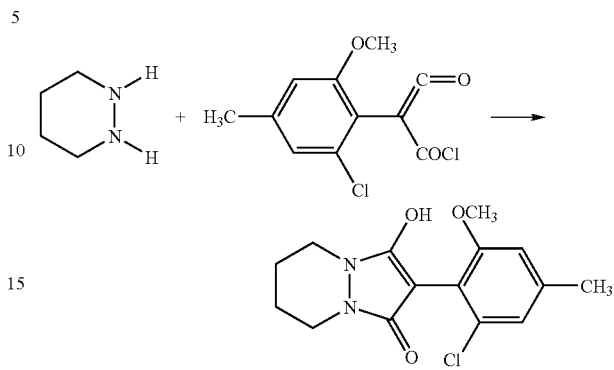

Using, for example, according to process (Hβ), hexahydropyridazine and dimethyl (2-chloro-4-methyl-6-methoxy)phenylmalonate as starting materials, the course of the process according to the invention can be represented by the reaction scheme below:

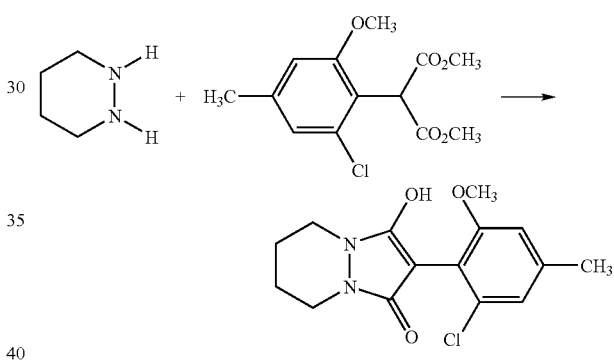

Using, for example, according to process (Hγ), 1-ethoxycarbonyl-2-[(2-chloro-4-methyl-6-methoxy)phenylacetyl] hexahydropyridazine as starting material, the course of the reaction can be represented by the scheme below:

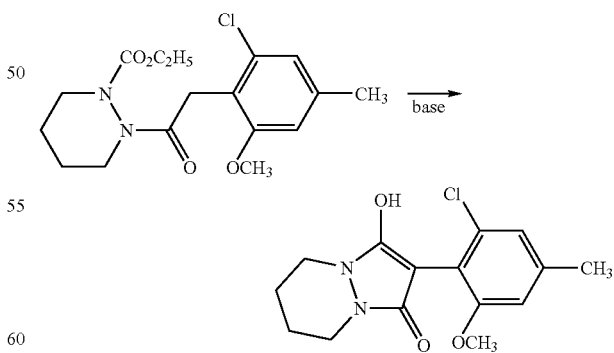

Using, for example, according to process (Iα), 3-(2-chloro-4-methyl-6-methoxyphenyl)-5,5-dimethylpyrrolidine-2,4-dione and pivaloyl chloride as starting materials, the course of the process according to the invention can be represented by the reaction scheme below:

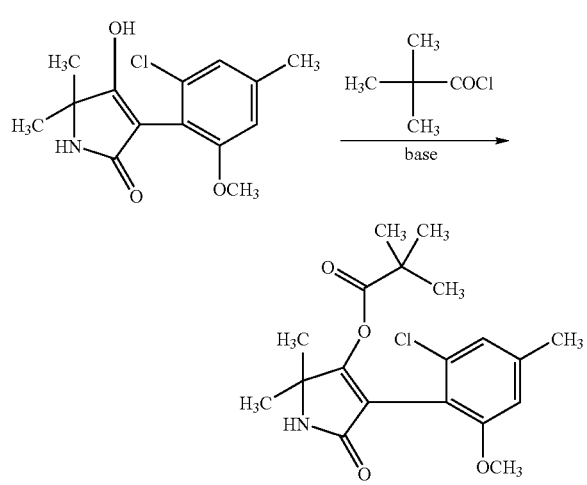

Using, for example, according to process (Iβ), 3-(2-chloro-4-methyl-6-methoxyphenyl)-4-hydroxy-5-phenyl-Δ³-dihydrofuran-2-one and acetic anhydride as starting materials, the course of the process according to the invention can be represented by the reaction below:

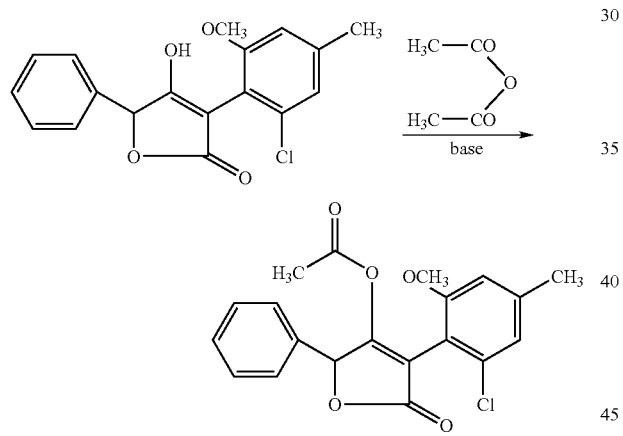

Using, for example, according to process (J), 8-[(2-chloro-4-methyl-6-methoxy)phenyl]-1-azabicyclo-(4,3,0¹,⁶)-nonane-7,9-dione and ethoxyethyl chloroformate as starting materials, the course of the process according to the invention can be represented by the reaction scheme below:

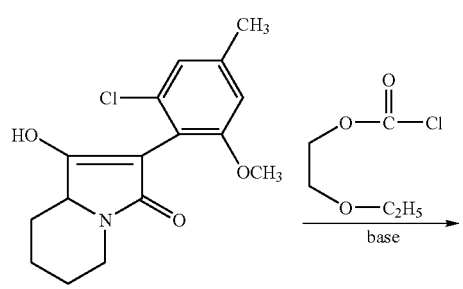

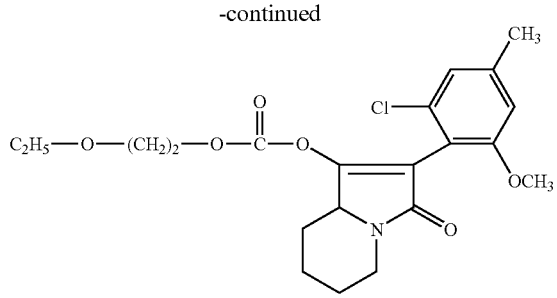

Using, for example, according to process (K), 3-(2-chloro-4-methyl-6-methoxyphenyl)-4-hydroxy-5-methyl-6-(3-pyridyl)pyrone and methyl chloromonothioformate as starting materials, the course of the reaction can be represented as follows:

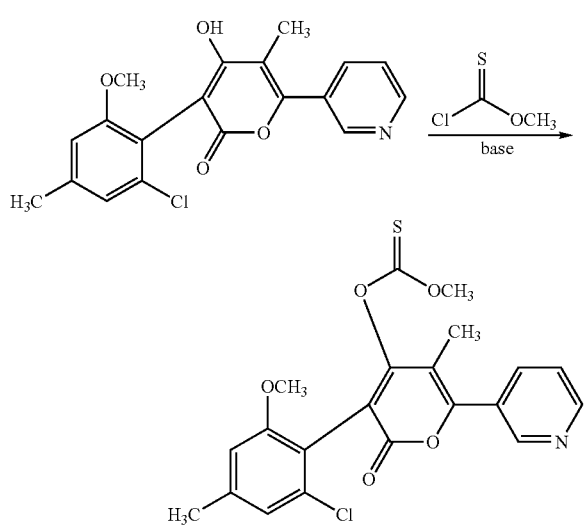

Using, for example, according to process (L), 3-(2-chloro-4-methyl-6-methoxyphenyl)-5,5-pentamethylenepyrrolidine-2,4-dione and methanesulphonyl chloride as starting materials, the course of the reaction can be represented by the reaction scheme below:

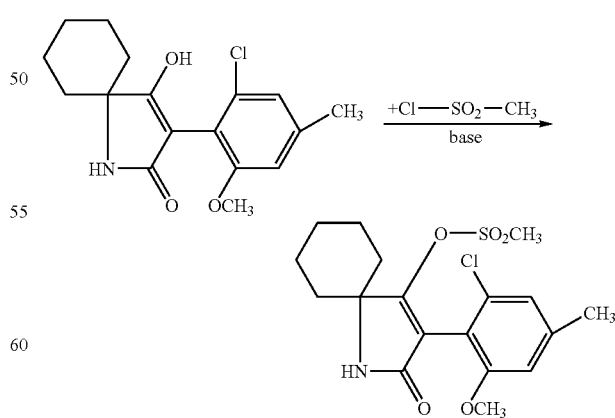

Using, for example, according to process (M), 3-(2-chloro-4-methyl-6-methoxyphenyl)-4-hydroxy-5,5-dimethyl-Δ³-dihydrofuran-2-one and 2,2,2-trifluoroethyl methanethiophosphonyl chloride as starting materials, the course of the reaction can be represented by the reaction scheme below:

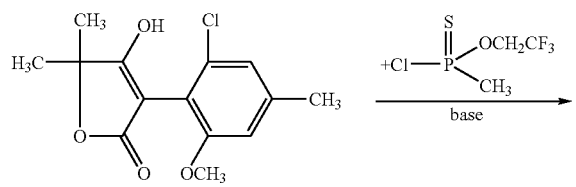

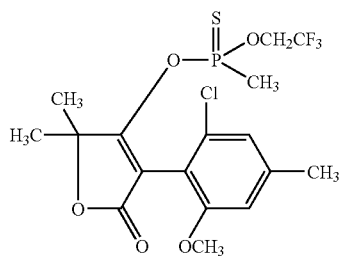

Using, for example, according to process (N), 3-(2-chloro-4-methyl-6-methoxyphenyl)-5-cyclopropyl-5-methylpyrrolidine-2,4-dione and NaOH as components, the course of the process according to the invention can be represented by the reaction scheme below:

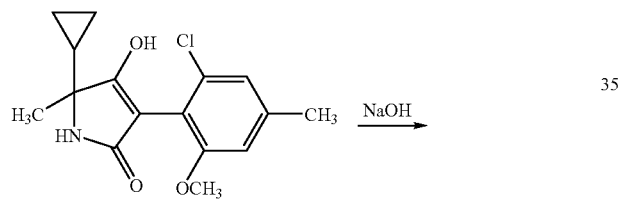

Using, for example, according to process (O), variant α, 3-(2-chloro-4-methyl-6-methoxyphenyl)-4-hydroxy-5-tetramethylene-$\Delta^3$-dihydrofuran-2-one and ethyl isocyanate as starting materials, the course of the reaction can be represented by the reaction scheme below:

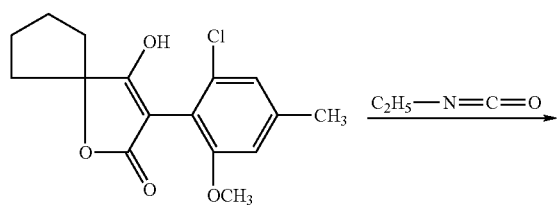

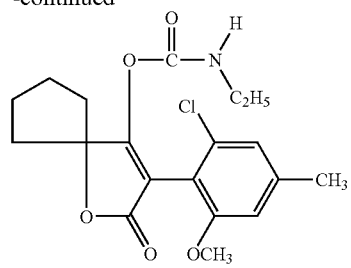

Using, for example, according to process (O), variant β, 3-(2-chloro-4-methyl-6-methoxyphenyl)-5-methylpyrrolidine-2,4-dione and dimethylcarbamoyl chloride as starting materials, the course of the reaction can be represented by the scheme below:

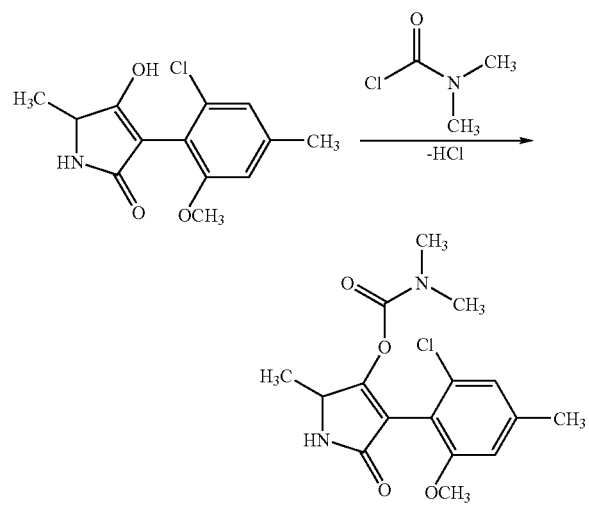

The compounds, required as starting materials in the process (a) according to the invention, of the formula (II)

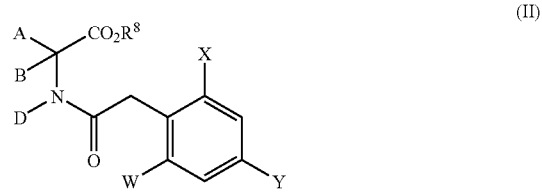

in which
A, B, D, W, X, Y and $R^8$ are as defined above
are novel.

The acylamino acid esters of the formula (II) are obtained, for example, when amino acid derivatives of the formula (XXIII)

in which
A, B, R⁸ and D are as defined above
are acylated with substituted phenylacetic acid derivatives of the formula (XXIV)

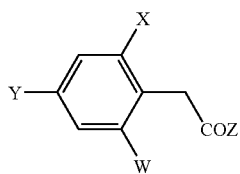

(XXIV)

in which
W, X and Y are as defined above and
Z represents a leaving group introduced by reagents that activate carboxylic acids, such as carbonyldiimidazole, carbonyldiimides (such as, for example, dicyclohexylcarbonyldiimide), phosphorylating reagents (such as, for example, POCl₃, BOP—Cl), halogenating agents, for example thionyl chloride, oxalyl chloride, phosgene or chloroformic esters
(Chem. Reviews 52, 237-416 (1953); Bhattacharya, Indian J. Chem. 6, 341-5, 1968)
or when acylamino acids of the formula (XXV)

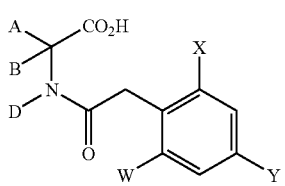

(XXV)

in which
A, B, D, W, X and Y are as defined above
are esterified (Chem. Ind. (London) 1568 (1968)).

The compounds of the formula (XXV)

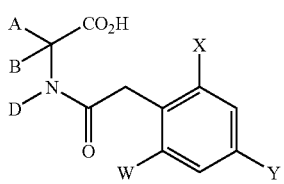

(XXV)

in which
A, B, D, W, X and Y are as defined above
are novel.

The compounds of the formula (XXV) are obtained when amino acids of the formula (XXVI)

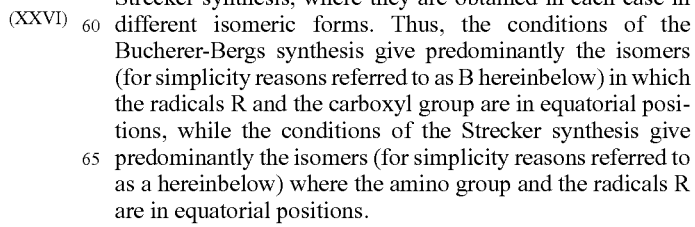

(XXVI)

in which
A, B and D are as defined above
are acylated with substituted phenyl acetic acid derivatives of the formula (XXIV)

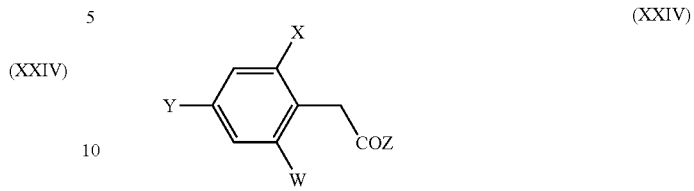

(XXIV)

in which
W, X and Y are as defined above and
Z is as defined above,
for example according to Schotten-Baumann (Organikum, VEB Deutscher Verlag der Wissen-schaften, Berlin 1977, p. 505).

The compounds of the formula (XXIV) are novel. They can be prepared by processes known in principle and as shown in the Preparation Examples (see, for example, H. Henecka, Houben-Weyl, Methoden der Organischen Chemie [Methods of Organic Chemistry], Vol. 8, pp. 467-469 (1952)).

The compounds of the formula (XXIV) are obtained, for example, by reacting substituted phenyl acetic acids of the formula (XXVII)

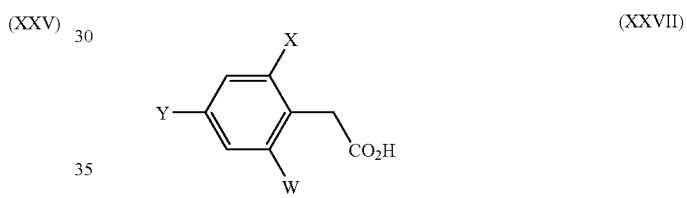

(XXVII)

in which
W, X and Y are as defined above
with halogenating agents (for example thionyl chloride, thionyl bromide, oxalyl chloride, phosgene, phosphorus trichloride, phosphorus tribromide or phosphorus pentachloride), phosphonylating reagents (such as, for example, POCl₃, BOP—Cl), carbonyldiimidazole, carbonyldiimides (for example dicyclohexylcarbonyldiimide), if appropriate in the presence of a diluent (for example optionally chlorinated aliphatic or aromatic hydrocarbons, such as toluene or methylene chloride, or ethers, for example tetrahydrofuran, dioxane, methyl tert-butyl ether), at temperatures of from −20° C. to 150° C., preferably from −10° C. to 100° C.

Some of the compounds of the formulae (XXIII) and (XXVI) are known and/or can be prepared by known processes (see, for example, Compagnon, Miocque Ann. Chim. (Paris) [14] 5, pp. 11-22, 23-27 (1970)).

The substituted cyclic aminocarboxylic acids of the formula (XXVI) in which A and B form a ring are generally obtained by means of a Bucherer-Bergs synthesis or a Strecker synthesis, where they are obtained in each case in different isomeric forms. Thus, the conditions of the Bucherer-Bergs synthesis give predominantly the isomers (for simplicity reasons referred to as B hereinbelow) in which the radicals R and the carboxyl group are in equatorial positions, while the conditions of the Strecker synthesis give predominantly the isomers (for simplicity reasons referred to as a hereinbelow) where the amino group and the radicals R are in equatorial positions.

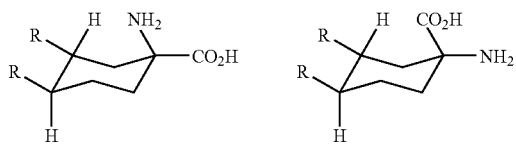

Bucherer-Bergs synthesis   Strecker synthesis
(β isomer)                 (α isomer)

(L. Munday, J. Chem. Soc. 4372 (1961); J. T. Eward, C. Jitrangeri, Can. J. Chem. 53, 3339 (1975).

Furthermore, the starting materials, used in process (A) above, of the formula (II)

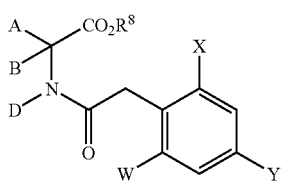

(II)

in which
A, B, D, W, X, Y and $R^8$ are as defined above
can be prepared by reacting aminonitriles of the formula (XXVIII)

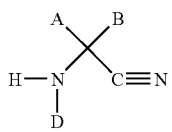

(XXVIII)

in which
A, B and D are as defined above
with substituted phenylacetic acid derivatives of the formula (XXIV)

(XXIV)

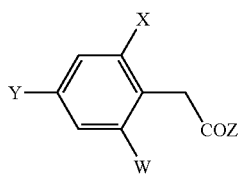

in which
W, X, Y and Z are as defined above
to give compounds of the formula (XXIX)

(XXIX)

in which
A, B, D, W, X and Y are as defined above,
which are then subjected to an acidic alcoholysis.

The compounds of the formula (XXIX) are also novel.

The compounds, required as starting materials for the process (B) according to the invention, of the formula (III)

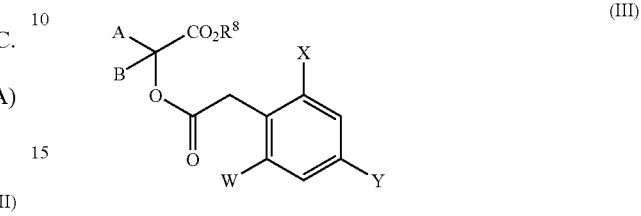

(III)

in which
A, B, W, X, Y and $R^8$ are as defined above
are novel.

They can be prepared by methods known in principle.

Thus, the compounds of the formula (III) are obtained, for example, when
2-hydroxycarboxylic esters of the formula (XXX-A)

(XXX-A)

in which
A, B and $R^8$ are as defined above
are acylated with substituted phenyl acetic acid derivatives of the formula (XXIV)

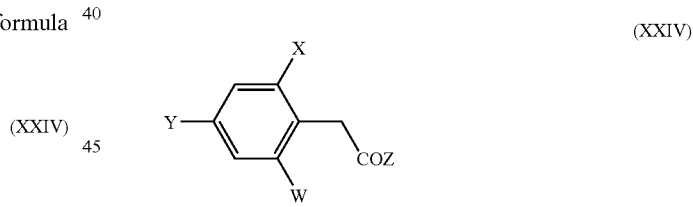

(XXIV)

in which
W, X and Y are as defined above
(Chem. Reviews 52, 237-416 (1953)).

Furthermore, compounds of the formula (III) are obtained when substituted phenylacetic acids of the formula (XXVII)

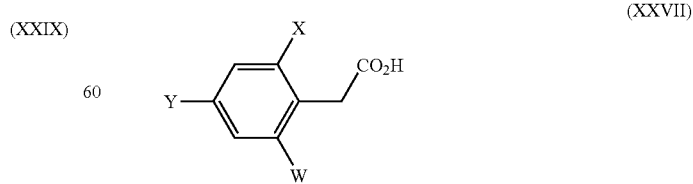

(XXVII)

in which
W, X and Y are as defined above are alkylated with α-halocarboxylic esters of the formula (XXX-B)

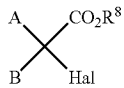
(XXX-B)

in which
A, B and $R^8$ are as defined above and
Hal represents chlorine or bromine.

The compounds of the formula (XXVII) are novel.
The compounds of the formula (XXX-B) are commercially available.
The compounds of the formula (XXVII)

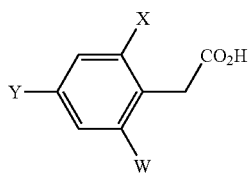
(XXVII)

in which
W, X and Y are as defined above
are obtained, for example, when phenylacetic esters of the formula (XXXI)

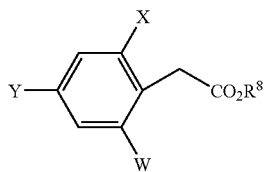
(XXXI)

in which
W, X, Y and $R^8$ are as defined above
are hydrolysed in the presence of acids or bases in the presence of a solvent under generally known standard conditions. Furthermore, phenylacetic acids of the formula (XXVII) are obtained by process (Q).
The compounds of the formula (XXXI) are novel.
The compounds of the formula (XXXI)

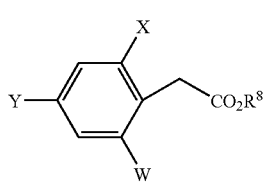
(XXXI)

in which
W, X, Y and $R^8$ are as defined above
are obtained, for example, by the process (R) described in the examples when phenylacetic esters of the formula (XXXI-a)

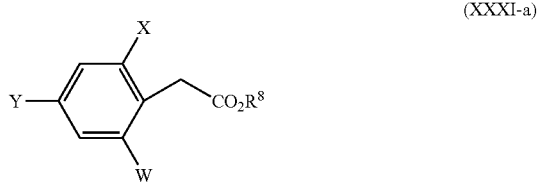
(XXXI-a)

in which
$R^8$, X and Y are as defined above and
W represents halogen (in particular bromine)
are reacted in the presence of an alcohol, in the presence of a base and, if appropriate, in the presence of a catalyst (preferably copper salts, such as, for example, copper(I) bromide).

The phenylacetic esters of the formula (XXXI-a) are known from the Application WO 96/35 664 or can be prepared by the processes described therein.

Furthermore, phenylacetic esters of the formula (XXXI) are obtained by the process (Q) described below by esterifying, according to standard methods, the phenylacetic acids of the formula (XXVII) obtained in this process.

The compounds, required as starting materials in the above process (C), of the formula (IV)

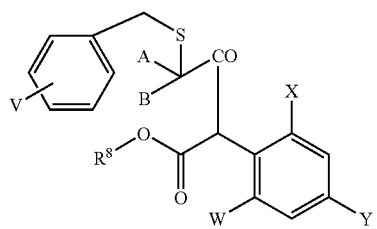
(IV)

in which
A, B, V, W, X, Y and $R^8$ are as defined above
are novel.

They can be prepared by methods known in principle.
The compounds of the formula (IV) are obtained, for example, when substituted phenylacetic esters of the formula (XXXI)

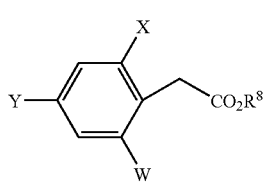
(XXXI)

in which
W, X, Y and $R^8$ are as defined above are acylated with 2-benzylthiocarbonyl halides of the formula (XXXII)

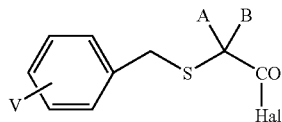

(XXXII)

in which
A, B and V are as defined above and
Hal represents halogen (in particular chlorine or bromine)
in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXII) are known, and/or they can be prepared by known processes (J. Antibiotics (1983), 26, 1589).

The halocarbonyl ketenes of the formula (VI) required as starting materials for the above processes (D), (E) and (H-α) are novel. They can be prepared by methods known in principle (cf., for example, Org. Prep. Proced. Int., 7, (4), 155-158, 1975 and DE-A-1 945 703). Thus, for example, the compounds of the formula (VI)

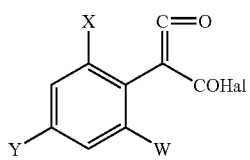

(VI)

in which
W, X and Y are as defined above and
Hal represents chlorine or bromine
are obtained when
substituted phenylmalonic acids of the formula (XXXIII)

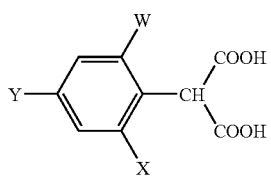

(XXXIII)

in which
W, X and Y are as defined above
are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methylstearylformamide or triphenylphosphine and, if appropriate in the presence of bases, such as, for example, pyridine or triethylamine.

The substituted phenylmalonic acids of the formula (XXXIII) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (XXXIII)

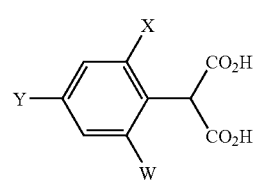

(XXXIII)

in which
W, X and Y are as defined above
are obtained when phenylmalonic acid derivatives of the formula (XI)

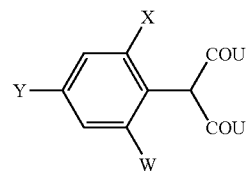

(XI)

in which
W, X and Y are as defined above and
U represents $OR^8$ or $NH_2$,
where
$R^8$ is as defined above,
are initially hydrolysed in the presence of a base and a solvent and then carefully acidified (EP-A-528 156, WO 96/35 664, WO 97/02 243).

The malonic acid derivatives of the formula (XI)

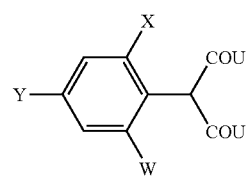

(XI)

in which
W, X and Y are as defined above and
U represents $OR^8$ or $NH_2$, where $R^8$ is as defined above
are novel.

They can be prepared by generally known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds, required as starting materials for the process (D) according to the invention, of the formula (V)

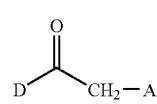

(V)

in which
A and D are as defined above or their silyl enol ethers of the formula (Va)

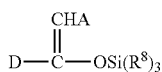
(Va)

in which
A, D and $R^8$ are as defined above
are compounds which are commercially available, generally known or obtainable by known processes.

The preparation of the ketene acid chlorides of the formula (VI) required as starting materials for carrying out the process (E) according to the invention has already been described above. The thioamides, required for carrying out the process (E) according to the invention, of the formula (VII)

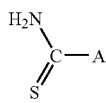
(VII)

in which
A is as defined above
are compounds which are generally known in organic chemistry.

The compounds, required as starting materials for the above process (F), of the formula (VIII)

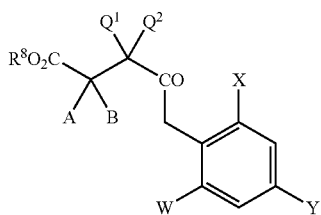
(VIII)

in which
A, B, $Q^1$, $Q^2$, W, X, Y and $R^8$ are as defined above
are novel.

They can be prepared by methods known in principle.
The 5-aryl-4-ketocarboxylic esters of the formula (VIII) are obtained, for example, when 5-aryl-4-ketocarboxylic acids of the formula (XXXIV)

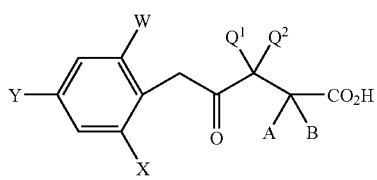
(XXXIV)

in which
W, X, Y, A, B, $Q^1$ and $Q^2$ are as defined above
are esterified (cf., for example, Organikum, 15th edition, Berlin, 1977, page 499) or alkylated (see Preparation Example).

The 5-aryl-4-ketocarboxylic acids of the formula (XXXIV)

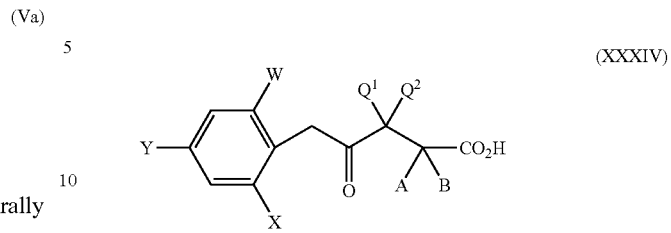
(XXXIV)

in which
A, B, $Q^1$, $Q^2$, W, X and Y are as defined above
are novel, but can be prepared by methods known in principle (WO 96/01 798, WO 97/14667, WO 98/39281).

The 5-aryl-4-ketocarboxylic acids of the formula (XXXIV) are obtained, for example, when 2-phenyl-3-oxoadipic esters of the formula (XXXV)

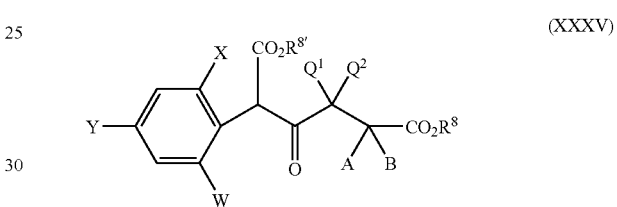
(XXXV)

in which
A, B, $Q^1$, $Q^2$, W, X and Y are as defined above and
$R^8$ and $R^{8'}$ represent alkyl (in particular $C_1$-$C_8$-alkyl) and in which,
if the compound of the formula (XXXVII-a) is used, $R^8$ represents hydrogen
are decarboxylated, if appropriate in the presence of a diluent and if appropriate in the presence of a base or an acid (cf., for example, Organikum, 15th edition, Berlin, 1977, pages 519 to 521).

The compounds of the formula (XXXV)

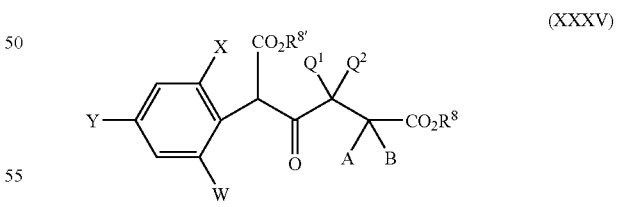
(XXXV)

in which
A, B, $Q^1$, $Q^2$, W, X, Y, $R^8$, $R^8$ are as defined above and in which,
if the compound of the formula (XXXVII-a) is used, $R^8$ represents hydrogen
are novel.

The compounds of the formula (XXXV) are obtained, for example, when dicarboxylic semiester chlorides of the formula (XXXVI),

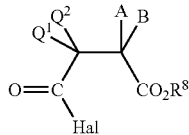
(XXXVI)

in which
A, B, $Q^1$, $Q^2$ and $R^8$ are as defined above and
Hal represents chlorine or bromine
or carboxylic anhydrides of the formula (XXXVII-a)

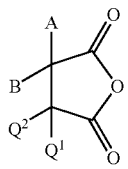
(XXXVII-a)

in which
A, B, $Q^1$ and $Q^2$ are as defined above
are acylated with a phenylacetic ester of the formula (XXXI)

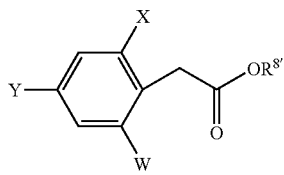
(XXXI)

in which
W, X, Y and $R^{8'}$ are as defined above
in the presence of a diluent and in the presence of an acid (cf., for example, M. S. Chambers, E. J. Thomas, D. J. Williams, J. Chem. Soc. Chem. Commun., (1987), 1228, cf. also the Preparation Examples).

Some of the compounds of the formulae (XXXVI) and (XXXVII-a) are known compounds of organic chemistry, and/or they can be prepared in a simple manner by methods known in principle.

The compounds, required as starting materials for the above process (G), of the formula (IX)

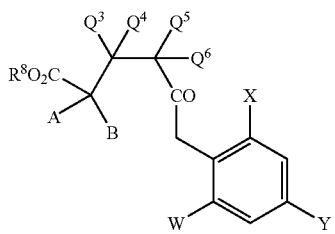
(IX)

in which
A, B, $Q^3$, $Q^4$, $Q^5$, $Q^6$, W, X, Y and $R^8$ are as defined above
are novel.

They can be prepared by methods known in principle.

The 6-aryl-5-ketocarboxylic esters of the formula (IX) are obtained, for example, when 6-aryl-5-ketocarboxylic acids of the formula (XXXVIII)

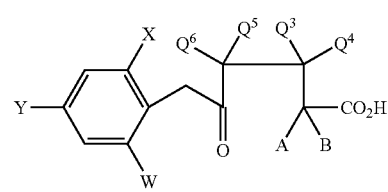
(XXXVIII)

in which
A, B, $Q^3$, $Q^4$, $Q^5$, $Q^6$, W, X and Y are as defined above
are esterified (cf., for example, Organikum, 15th edition, Berlin, 1977, page 499).

The 6-aryl-5-ketocarboxylic acids of the formula (XXXVIII)

(XXXVIII)

in which
A, B, $Q^3$, $Q^4$, $Q^5$, $Q^6$, W, X and Y are as defined above
are novel. They can be prepared by methods known in principle (WO 99/43649, WO 99/48869), for example by
hydrolysing and decarboxylating substituted 2-phenyl-3-oxoheptanedioic esters of the formula (XXXIX)

(XXXIX)

in which
A, B, $Q^3$, $Q^4$, $Q^5$, $Q^6$, W, X and Y are as defined above and
$R^8$ and $R^{8'}$ represent alkyl (preferably $C_1$-$C_6$-alkyl) and in which,
if the compound of the formula (XXXVII-b) is used, $R^8$ represents hydrogen,
if appropriate in the presence of a diluent and if appropriate in the presence of a base or an acid (cf., for example, Organikum, 15. edition, Berlin, 1977, pages 519 to 521).

The compounds of the formula (XXXIX)

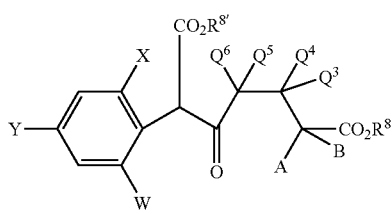
(XXXIX)

in which
A, B, Q³, Q⁴, Q⁵, Q⁶, W, X, Y, R⁸ and R⁸' are as defined above
are novel and can be obtained
by condensing dicarboxylic esters of the formula (XL)

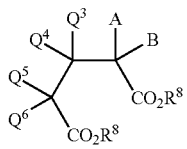
(XL)

in which
A, B, Q³, Q⁴, Q⁵, Q⁶ and R⁸ are as defined above
or carboxylic anhydrides of the formula (XXXVII-b)

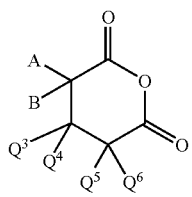
(XXXVII-b)

in which A, B, Q³, Q⁴, Q⁵, Q⁶ are as defined above
with a substituted phenylacetic ester of the formula (XXXI)

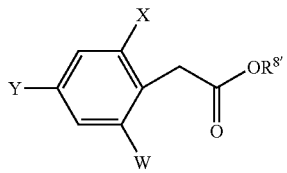
(XXXI)

in which
W, X, Y and R⁸' are as defined above
in the presence of a diluent and in the presence of a base.

Some of the compounds of the formula (XL) are known, and/or they can be prepared by known processes.

Some of the hydrazines, required as starting materials for the processes (H-α) and (H-β) according to the invention, of the formula (X)

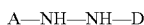
A—NH—NH—D    (X)

in which
A and D are as defined above
are known, and/or they can be prepared by methods known from the literature (cf., for example, Liebigs Ann. Chem. 585, 6 (1954); Reaktionen der organischen Synthese [Reactions of Organic Synthesis], C. Ferri, page 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds, required for the process (H-γ) according to the invention, of the formula (XII)

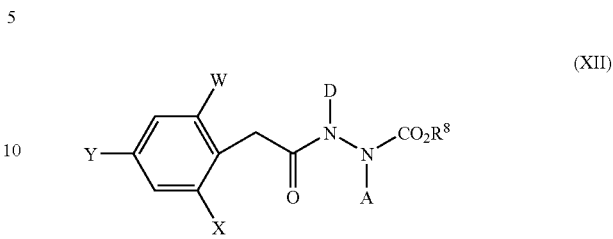
(XII)

in which
A, D, W, X, Y and R⁸ are as defined above
are novel.

The acylcarbazates of the formula (XII) are obtained, for example, when carbazates of the formula (XLI)

(XLI)

in which
A, R⁸ and D are as defined above
are acylated with substituted phenylacetic acid derivatives of the formula (XXIV)

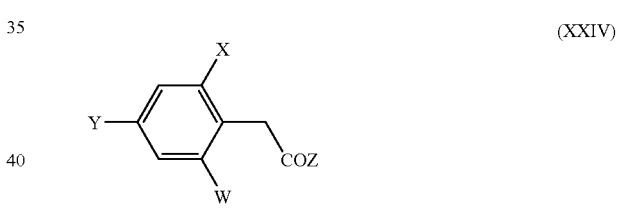
(XXIV)

in which
W, X, Y and Z are as defined above
(Chem. Reviews 52, 237-416 (1953); Bhattacharya, Indian J. Chem. 6, 341-5, 1968).

Some of the compounds of the formula (XLI) are commercially available and some are known compounds, or they can be prepared by processes of organic chemistry known in principle.

The compounds of the formula (XXVII) have already been described under the precursors for process (A), or they are described explicitly as examples in the process (Q) below.

(Q) Thus, furthermore, phenylacetic acids of the formula (XXVII),

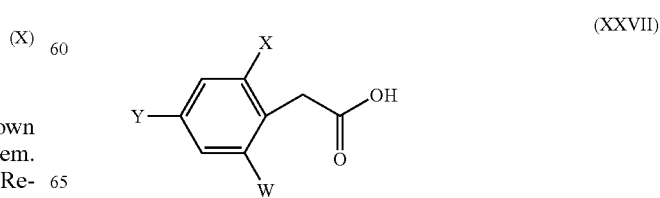
(XXVII)

in which
W, X and Y are as defined above
are obtained when phenylacetaldehydes of the formula (XLII)

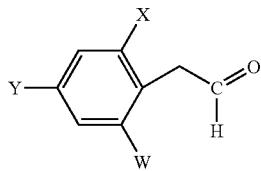
(XLII)

in which
W, X and Y are as defined above
are oxidized, if appropriate in the presence of a solvent, using suitable oxidizing agents (such as, for example, NaOCl).
The compounds of the formula (XLII) are novel.
Compounds of the formula (XLII)

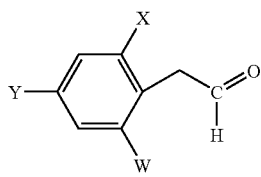
(XLII)

in which
W, X and Y are as defined above
are obtained when 3-phenylpropenes of the formula (XLIII)

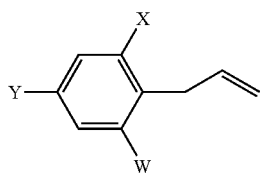
(XLIII)

in which
W, X and Y are as defined above
are ozonolysed in the presence of a solvent, and the ozonide obtained is worked up reductively using, for example, dimethyl sulphide.

The 2-alkoxy-substituted 3-phenylpropenes required for preparing the compounds of the formula (XLII) are compounds known in principle in organic chemistry and can be prepared according to standard processes by alkylating phenols with allyl halides, followed by Claisen rearrangement and subsequent alkylation (WO 96/25 395).

The acid halides of the formula (XIII), carboxylic anhydrides of the formula (XIV), chloroformic esters or chloroformic thioesters of the formula (XV), chloromonothioformic esters or chlorodithioformic esters of the formula (XVI), sulphonyl chlorides of the formula (XVII), phosphorus compounds of the formula (XVIII) and metal hydroxides, metal alkoxides or amines of the formulae (XIX) and (XX) and isocyanates of the formula (XXI) and carbamoyl chlorides of the formula (XXII) furthermore required as starting materials for carrying out the processes (I), (J), (K), (L), (M), (N) and (O) according to the invention are generally known compounds of organic or inorganic chemistry.

In addition, the compounds of the formulae (V), (VII), (XIII) to (XXII), (XXIII), (XXVI), (XXVIII), (XXX-A), (XXX-B), (XXXII), (XXXVI), (XXXVII-a), (XXXVII-b), (XL) and (XLI) are known from the patent applications cited at the outset, and/or they can be prepared by the methods given therein.

The process (A) is characterized in that compounds of the formula (II) in which A, B, D, W, X, Y and $R^8$ are as defined above are, in the presence of a base, subjected to an intramolecular condensation.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures can be varied within a relatively large range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately doubly equimolar amounts. However, it is also possible to use a relatively large excess (up to 3 mol) of one component or the other.

The process (B) is characterized in that compounds of the formula (III) in which A, B, W, X, Y and $R^8$ are as defined above are, in the presence of a diluent and in the presence of a base, subjected to an intramolecular condensation.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, V, W, X, Y and $R^8$ are as defined above are, in the presence of an acid and, if appropriate, in the presence of a diluent, subjected to intramolecular cyclization.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

If appropriate, the acid used can also serve as diluent.

Suitable acids for the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the process is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acids are employed, for example, in equimolar amounts. However, it is, if appropriate, also possible to use the acid as solvent or as catalyst.

The process (D) according to the invention is characterized in that carbonyl compounds of the formula (V) or enol ethers thereof of the formula (V-a) are reacted with ketene acid halides of the formula (VI) in the presence of a diluent and, if appropriate, in the presence of an acid acceptor.

Suitable diluents for the process (D) according to the invention are all inert organic solvents. Preference is given to using optionally halogenated hydrocarbons, such as toluene, xylene, mesitylene, chlorobenzene and dichlorobenzene, furthermore ethers, such as dibutyl ether, glycol dimethyl ether, diglycol dimethyl ether and diphenyl ether, moreover polar solvents, such as dimethyl sulphoxide, sulpholane, dimethylformamide or N-methylpyrrolidone.

Suitable acid acceptors for carrying out the process variant (D) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (D) according to the invention, the reaction temperatures can be varied within a relatively wide range. The process variant is expediently carried out at temperatures between 0° C. and 250° C., preferably between 50° C. and 220° C.

The process (D) according to the invention is expediently carried out under atmospheric pressure.

When carrying out the process (D) according to the invention, the reaction components of the formulae (V) and (VI) in which A, D, W, X and Y are as defined above and Hal represents halogen and, if appropriate, the acid acceptors are generally employed in approximately equimolar amounts. However, it is also possible to use a relatively large excess (up to 5 mol) of one component or the other.

The process (E) according to the invention is characterized in that thioamides of the formula (VII) are reacted with ketene acid halides of the formula (VI) in the presence of a diluent and, if appropriate, in the presence of an acid acceptor.

Suitable diluents for the process variant (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methylpyrrolidone.

Suitable acid acceptors for carrying out the process (E) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process (E) according to the invention, the reaction temperatures can be varied within a relatively wide range. Expediently, the process is carried out at temperatures between 0° C. and 250° C., preferably between 20° C. and 220° C.

The process (E) according to the invention is expediently carried out under atmospheric pressure.

When carrying out the process (E) according to the invention, the reaction components of the formulae (VII) and (VI) in which A, W, X and Y are as defined above and Hal represents halogen and, if appropriate, the acid acceptors are generally employed in approximately equimolar amounts. However, it is also possible to use a relatively large excess (up to 5 mol) of one component or the other.

The process (F) is characterized in that compounds of the formula (VIII) in which A, B, $Q^1$, $Q^2$, W, X, Y and $R^8$ are as defined above are, in the presence of a base, subjected to an intramolecular condensation.

Suitable diluents for the process (F) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (F) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, such as, for example, triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (F) according to the invention, the reaction temperatures can be varied within a relatively wide range. In general, the process is carried out at temperatures between −75° C. and 250° C., preferably between −50° C. and 150° C.

The process (F) according to the invention is generally carried out under atmospheric pressure.

When carrying out the process (F) according to the invention, the reaction components of the formula (VIII) and the deprotonating bases are generally employed in approximately equimolar amounts. However, it is also possible to use a relatively large excess (up to 3 mol) of one component or the other.

The process (G) is characterized in that compounds of the formula (IX) in which A, B, $Q^3$, $Q^4$, $Q^5$, $Q^6$, W, X, Y and $R^8$ are as defined above are, in the presence of bases, subjected to an intramolecular condensation.

Suitable diluents for the process (G) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (G) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, such as, for example, triethylbenzylammonium chloride, tetra-butylammonium bromide, Adogen 464 (methyltrialkyl($C_8$-$C_{10}$)ammonium chloride) or TDA 1 (tris (methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (G) according to the invention, the reaction temperatures can be varied within a relatively wide range. In general, the process is carried out at temperatures between 0° C. and 250° C., preferably between 50° C. and 150° C.

The process (G) according to the invention is generally carried out under atmospheric pressure.

When carrying out the process (G) according to the invention, the reaction components of the formula (IX) and the deprotonating bases are generally employed in approximately equimolar amounts. However, it is also possible to use a relatively large excess (up to 3 mol) of one component or the other.

The process (H-α) according to the invention is characterized in that hydrazines of the formula (X) or salts of these compounds are reacted with ketene acid halides of the formula (VI) in the presence of a diluent and, if appropriate, in the presence of an acid acceptor.

Suitable diluents for the process (H-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenyl ether, moreover polar solvents, such as dimethyl sulphoxide, sulpholane, dimethylformamide or N-methylpyrrolidone.

Suitable acid acceptors for carrying out the process variant (H-α) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (H-α) according to the invention, the reaction temperatures can be varied within a relatively wide range. The process variant is expediently carried out at temperatures between 0° C. and 250° C., preferably between 50° C. and 220° C.

The process (H-α) according to the invention is expediently carried out under atmospheric pressure.

When carrying out the process (H-α) according to the invention, the reaction components of the formulae (VI) and (X) in which A, D, W, X and Y are as defined above and Hal represents halogen and, if appropriate, the acid acceptors are generally employed in approximately equimolar amounts. However, it is also possible to use a relatively large excess (up to 5 mol) of one component or the other.

The process (H-β) is characterized in that hydrazines of the formula (X) or salts of this compound in which A and D are as defined above are, in the presence of a base, subjected to a condensation with malonic esters or malonamides of the formula (XI) in which U, W, X, Y and $R^8$ are as defined above.

Suitable diluents for the process (H-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetra-hydrofuran, dioxane, diphenyl ether, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (H-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, and which can also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

It is also possible to use tertiary amines, such as triethylamine, pyridine, diazabicyclooctane (DABCO), diazabicycloundecane (DBU), diazabicyclononene (DBN), Hünig base and N,N-dimethylaniline.

When carrying out the process (H-β) according to the invention, the reaction temperatures can be varied within a relatively wide range. In general, the process is carried out at temperatures between 0° C. and 280° C., preferably between 50° C. and 180° C.

The process (H-β) according to the invention is generally carried out under atmospheric pressure.

When carrying out the process (H-β) according to the invention, the reaction components of the formulae (XI) and (X) are generally employed in approximately equimolar amounts. However, it is also possible to use a relatively large excess (up to 3 mol) of one component or the other.

The process (H-γ) is characterized in that compounds of the formula (XII) in which A, D, W, X, Y and $R^8$ are as defined above are, in the presence of a base, subjected to an intramolecular condensation.

Suitable diluents for the process (H-γ) according to the invention are all inert organic solvents. Preference is given to using hydrocarbons, such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (H-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, and which can also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (H-γ) according to the invention, the reaction temperatures can be varied within a relatively wide range. In general, the process is carried out at temperatures between 0° C. and 250° C., preferably between 50° C. and 150° C.

The process (H-γ) according to the invention is generally carried out under atmospheric pressure.

When carrying out the process (H-γ) according to the invention, the reaction components of the formula (XII) and the deprotonating bases are generally employed in approximately doubly equimolar amounts. However, it is also possible to use a relatively large excess (up to 3 mol) of one component or the other.

The process (I-α) is characterized in that compounds of the formulae (I-1-a) to (I-8-a) are in each case reacted with carbonyl halides of the formula (XIII), if appropriate in the presence of a diluent and if appropriate in the presence of an acid binder.

Suitable diluents for the process (I-α) according to the invention are all solvents which are inert towards the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction according to the process (I-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

In the process (I-α) according to the invention, the reaction temperatures can be varied within a relatively wide range. In general, the process is carried out at temperatures between −20° C. and +150° C., preferably between 0° C. and 100° C.

When carrying out the process (I-α) according to the invention, the starting materials of the formulae (I-1-a) to (I-8-a) and the carbonyl halide of the formula (XIII) are generally each employed in approximately equivalent amounts. However, it is also possible to use a relatively large excess (up to 5 mol) of the carbonyl halide. Work-up is carried out by customary methods.

The process (I-β) is characterized in that compounds of the formulae (I-1-a) to (I-8-a) are reacted with carboxylic anhydrides of the formula (XIV), if appropriate in the presence of a diluent and if appropriate in the presence of an acid binder.

Suitable diluents for the process (I-β) according to the invention are, preferably, those diluents which are also preferred when using acid halides. Besides, it may also be possible for excess carboxylic anhydride to act simultaneously as diluent.

In process (I-β), suitable acid binders, which are added, if appropriate, are preferably those acid binders which are also preferred when using acid halides.

The reaction temperatures in the process (I-β) according to the invention can be varied within a relatively wide range. In general, the process is carried out at temperatures between −20° C. and +150° C., preferably between 0° C. and 100° C.

When carrying out the process (I-β) according to the invention, the starting materials of the formulae (I-1-a) to (I-8-a) and the carboxylic anhydride of the formula (XIV) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (J) is characterized in that compounds of the formulae (I-1-a) to (I-8-a) are in each case reacted with chloroformic esters or chloroformic thioesters of the formula (XV), if appropriate in the presence of a diluent and if appropriate in the presence of an acid binder.

Suitable acid binders for the reaction according to the process (J) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (J) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (J) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (J) according to the invention is generally carried out under atmospheric pressure.

When carrying out the process (J) according to the invention, the starting materials of the formulae (I-1-a) to (I-8-a) and the appropriate chloroformic ester or chloroformic thioester of the formula (XIII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (K) according to the invention is characterized in that compounds of the formulae (I-1-a) to (I-8-a) are in each case reacted with compounds of the formula (XVI), in the presence of a diluent and, if appropriate, in the presence of an acid binder.

In Preparation Process (K), about 1 mol of chloromonothioformic ester or chlorodithioformic ester of the formula (XVI) is reacted per mole of starting material of the formulae (I-1-a) to (I-8-a), at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by the addition of strong deprotonating agents, such as, for example, sodium hydride or potassium tert-butoxide, the further addition of acid binders can be dispensed with.

If acid binders are used, these are customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (L) according to the invention is characterized in that compounds of the formulae (I-1-a) to (I-8-a) are in each case reacted with sulphonyl chlorides of the formula (XVII), if appropriate in the presence of a diluent and if appropriate in the presence of an acid binder.

In the Preparation Process (L), about 1 mol of sulphonyl chloride of the formula (XVII) is reacted per mole of starting material of the formula (I-1-a to I-8-a), at from −20 to 150° C., preferably from 20 to 70° C.

Suitable diluents, which are added, if appropriate, are all inert polar organic solvents, such as ethers, amides, nitriles, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-8-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (M) according to the invention is characterized in that compounds of the formulae (I-1-a) to (I-8-a) are in each case reacted with phosphorus compounds of the formula (XVIII), if appropriate in the presence of a diluent and if appropriate in the presence of an acid binder.

In the Preparation Process (M), to obtain compounds of the formulae (I-1-e) to (I-8-e), 1 to 2, preferably 1 to 1.3 mol of the phosphorus compound of the formula (XVIII) are reacted to 1 mol of the compounds (I-1-a) to (I-8-a), at temperatures between 40° C. and 150° C., preferably between −10 and 110° C.

Suitable diluents, which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethyl-formamide, methylene chloride.

Suitable acid binders, which are added, if appropriate, are customary inorganic or organic bases, such as hydroxides, carbonates or amines. Examples are sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods of organic chemistry. The end products obtained are preferably purified by crystallization, chromatographic purification or by "incipient distillation", i.e. removal of the volatile components under reduced pressure.

The process (N) is characterized in that compounds of the formulae (I-1-a) to (I-8-a) are reacted with metal hydroxides or metal alkoxides of the formula (XIX) or amines of the formula (XX), if appropriate in the presence of a diluent.

Suitable diluents for the process (N) according to the invention are, preferably, ethers, such as tetrahydrofuran, dioxane, diethyl ether, or else alcohols, such as methanol, ethanol, isopropanol, and also water.

The process (N) according to the invention is generally carried out under atmospheric pressure.

The reaction temperatures are generally between −20° C. and 100° C., preferably between 0° C. and 50° C.

The process (O) according to the invention is characterized in that compounds of the formulae (I-1-a) to (I-8-a) are in each case reacted with (O-α) compounds of the formula (XXI), if appropriate in the presence of a diluent and if appropriate in the presence of a catalyst, or with (O-β) compounds of the formula (XXII), if appropriate in the presence of a diluent and if appropriate in the presence of an acid binder.

In Preparation Process (O-α), about 1 mol of isocyanate of the formula (XXI) is reacted per mole of starting material of the formulae (I-1-a) to (I-8-a), at from 0 to 100° C., preferably at from 20 to 50° C.

Suitable diluents, which are added, if appropriate, are all inert organic solvents, such as ethers, amides, nitriles, sulphones, sulphoxides.

If appropriate, catalysts may be added to accelerate the reaction. Suitable catalysts are, very advantageously, organotin compounds, such as, for example, dibutyltin dilaurate. The reaction is preferably carried out under atmospheric pressure.

In the Preparation Process (O-β), about 1 mol of carbamoyl chloride of the formula (XXII) is reacted per mole of starting material of the formulae (I-1-a) to (I-8-a), at from −20 to 150° C., preferably from 0 to 70° C.

Suitable diluents, which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-8-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The process (P) is characterized in that compounds of the formulae (I-1-a') to (I-8-a') in which A, B, D, $Q^1, Q^2, Q^3, Q^4, Q^5, Q^6$, X and Y are as defined above and W' preferably represents bromine are reacted with alcohols of the formula W—OH in which W is as defined above, in the presence of a base and a Cu(I) salt (for example CuBr or CuI).

Suitable diluents for the process (P) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methylpyrrolidone, esters, such as methyl acetate, ethyl acetate, propyl acetate, and also alcohols of the formula W—OH, such as, for example, methanol, ethanol, propanol, isopropanol, butanol, isobutanol, tert-butanol, glycol monomethyl ether or diethylene glycol monoethyl ether.

Suitable bases (deprotonating agents) for carrying out the process (P) according to the invention are all customary proton acceptors. Preference is given to using alkali metals, such as sodium or potassium. It is also possible to use alkali metal and alkaline earth metal amides and hydrides, such as sodium amide, sodium hydride and calcium hydride, and, preferably, also alkali metal alkoxides, such as sodium methoxide, sodium ethoxide, sodium isopropoxide, sodium tert-butoxide and potassium tert-butoxide.

When carrying out the process (P) according to the invention, the reaction temperatures can be varied within a relatively wide range. In general, the process is carried out at temperatures between 0° C. and 250° C., preferably between 50° C. and 150° C. The process (P) according to the invention is generally carried out under atmospheric pressure.

When carrying out the process (P) according to the invention, the reaction components of the formulae (I-1-a') to (I-8-a') are generally reacted with an excess of the alcohol W—OH and the base up to 20 mol, preferably 3 to 5 mol. The copper(I) salts are generally employed in catalytic amounts of from 0.001 to 0.5 mol, preferably from 0.01 to 0.2 mol. However, they can also be employed in equimolar amounts.

The active compounds are well tolerated by plants and have advantageous toxicity to warm-blooded species; they can be employed for controlling animal pests, in particular insects, arachnids and nematodes encountered in agriculture, forests, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps,*

*Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorphoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds or active compound combinations according to the invention may also be used in certain concentrations or application rates to act as herbicides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds or active compound combinations is carried out directly or by allowing the compounds to act on the surroundings, environment or storage space by the customary treatment methods, for example by immersion, spraying, evaporation, fogging, scattering, painting on or injection and, in the case of propagation material, in particular in the case of seeds, also by applying one or more coats.

The active compounds or active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as components in the mixtures are, for example, the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris (albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decan-3-amine; sodium tetrathiocarbonate;

and copper salts and preparations such as Bordeaux mixture; copper hydroxide; copper naphthenate; copper oxychloride; copper sulphate; cufraneb; cuprous oxide; mancopper, oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluoron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (IR-trans isomer), cyromazine, DDT, deltamethrin, demeton-S-methyl, demeton-S-methyl-sulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, *Entomophthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metarhizium anisopliae, Metarhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700; monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, spirotetramat, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma atroviride*, triflumuron, trimethacarb, vamidothion, vaniliprole, verbutin, *Verticillium lecanii*, WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds, such as herbicides, or with fertilizers and growth regulators is also possible.

When used as insecticides in their commercially available formulations and in the use forms prepared with these formulations, the active compounds according to the invention can furthermore exist in the form of a mixture with synergists. Synergists are compounds by which the activity of the active compounds is increased without it being necessary for the synergist added to be active itself.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound or active compound combination is distinguished by excellent residual action on wood and clay as well as good stability to alkali on limed substrates.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, oilseed rape, beet, sugar cane and fruit plants (with the fruits apples, pears, citrus fruits and grapes), with particular emphasis on maize, soybeans, potatoes, cotton and oilseed rape. Traits which are especially emphasized are the increased defense of the plants against insects, owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously with the compounds according to the invention or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds or active compound combinations according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the sub-class of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds or active compound combinations according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds or active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds or active compound combinations can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds or active compound combinations according to the invention have a potent insecticidal action against insects which destroy industrial materials.

The following insects may be mentioned by way of example and as being preferred, but without any limitation:
Beetles, such as
*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint. The materials to be very particularly preferably protected against attack by insects are wood and timber products.

Wood and timber products which can be protected by the composition according to the invention or mixtures comprising such a composition are to be understood as meaning, for example:
construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds or active compound combinations can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries. The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid and triflumuron,
and fungicides, such as epoxyconazole, hexaconazole, azaconazole, propiconazole, tebuconazole, cyproconazole, metconazole, imazalil, dichlofluanid, tolylfluanid, 3-iodo-2-propynylbutyl carbamate, N-octylisothiazolin-3-one and 4,5-dichloro-N-octylisothiazolin-3-one.

The compounds or active compound combinations according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdimethyldithiocarbamoylzinc ethylene-bisthiocarbamate, zinc oxide, copper(I) ethylene-bisdithiocarbamate, copper thiocyanate, copper naphthenate and tri-butyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propynyl butylcarbamate, tolylfluanid and azoles such as
azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacrb;
or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridinetriphenylborane, tetrabutyldistannoxane, 2,3,5,6-tetrachloro-4-(methylsulphonyl) pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds or active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds or active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds or active compound combinations according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds or active compound combinations according to the invention is in no way restricted to these genera, but extends in the same manner to other plants.

Depending on the concentration, the active compounds or active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantations and hop fields, on lawns, turf and pastureland, and for the selective control of weeds in annual crops.

The compounds or active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds or active compound combinations according to the invention can also be employed for controlling animal pests and fungal or bacterial plant diseases. If appropriate, they can also be used as intermediates or precursors for the synthesis of other active compounds.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron(-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluoroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insectides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additive in the formulations, mineral or vegetable oils which are tolerated by plants (for example commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.001 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, rice), maize, soybeans, potatoes, cotton, oil seed rape, beet, sugar cane and also fruit plants (with the fruits apples, pears, citrus fruits and grapevines), greater emphasis being given to maize, soybeans, potatoes, cotton and oil seed rape.

The preparation and the use of the active compounds according to the invention are illustrated by the examples below.

PREPARATION EXAMPLES

Example No. I-1-a-1

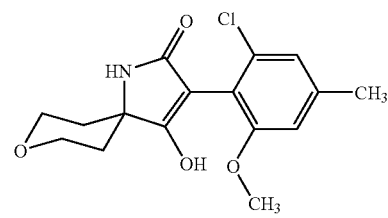

Under argon, 2.6 g of potassium tert-butoxide, 95% pure (21.6 mmol), are initially charged in 8 ml of dimethyl acetamide in a 100 ml three-necked flask fitted with thermometer and reflux condenser. At 50-60° C., 3.5 g (9.8 mmol) of the compound of Example II-1 in 10 ml of dimethylacetamide are added dropwise. The mixture is stirred for 1 h and monitored by thin-layer chromatography. The reaction mixture is stirred into 100 ml of ice-water and adjusted to pH 2 using concentrated HCl, and the precipitate is filtered off with suction. The product is purified by silica gel column chromatography (dichloromethane:ethyl acetate=5:3).

Yield: 3.15 g (98% of theory), m.p.: 193° C.

The following compounds of the formula (I-1-a) are obtained analogously to Example (I-1-a-1) and in accordance with the general statements on the preparation

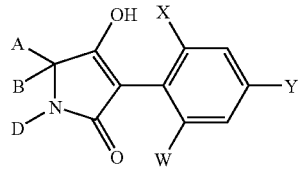

(I-1-a)

| Ex. No. | W | X | Y | D | A | B | m.p. °C. | Isomer |
|---|---|---|---|---|---|---|---|---|
| I-1-a-2 | OCH$_3$ | Cl | CH$_3$ | H | CH$_3$ | CH$_3$ | 191 | — |
| I-1-a-3 | OCH$_3$ | Cl | CH$_3$ | H | —(CH$_2$)$_2$—CHOCH$_3$—(CH$_2$)$_2$— | | 219 | β |
| I-1-a-4 | OC$_3$H$_7$ | Cl | CH$_3$ | H | —(CH$_2$)$_2$—CHOCH$_3$—(CH$_2$)$_2$— | | ** | β |
| I-1-a-5 | OC$_2$H$_5$ | Cl | CH$_3$ | H | —(CH$_2$)$_2$—CHOCH$_3$—(CH$_2$)$_2$— | | 132 | β |
| I-1-a-6 | O—(CH$_2$)$_2$O—CH$_3$ | Cl | CH$_3$ | H | —(CH$_2$)$_2$—CHOCH$_3$—(CH$_2$)$_2$— | | 130 | β |
| I-1-a-7 | O—CH$_2$—cyclopropyl | Cl | CH$_3$ | H | —(CH$_2$)$_2$—CHOCH$_3$—(CH$_2$)$_2$— | | 148 | β |
| I-1-a-8 | OCH$_3$ | Cl | CH$_3$ | H | C$_2$H$_5$ | CH$_3$ | *0.77 (m, 3 H, CH$_2$CH$_3$) 2.30 (s, 3 H, Ar—CH$_3$) | |
| I-1-a-9 | OC$_2$H$_5$ | Cl | CH$_3$ | H | cyclopropyl | CH$_3$ | 195 | |
| I-1-a-10 | OC$_2$H$_5$ | Cl | CH$_3$ | H | C$_2$H$_5$ | CH$_3$ | *0.78 (dt, 3 H, CH$_2$—CH$_3$) 2.29 (s, 3 H, Ar—CH$_3$) | |
| I-1-a-11 | OC$_2$H$_5$ | Cl | CH$_3$ | C$_2$H$_5$ | CH$_3$ | H | 107 | |
| I-1-a-12 | OCH$_3$ | Cl | CH$_3$ | H | i-C$_3$H$_7$ | CH$_3$ | *1.30 (s, 3 H, N—C(CH$_3$)—) 1.85-1.95 (m, 1 H), —CH—(CH$_3$)$_2$) | |
| I-1-a-13 | OCH$_3$ | Cl | CH$_3$ | H | i-C$_4$H$_9$ | CH$_3$ | *0.85-0.95 (m, 6 H, CH$_2$—(CH$_3$)$_2$) 1.60-1.70 (m, 2 H, CH$_2$—(CH$_3$)$_2$) | |
| I-1-a-14 | OC$_3$ | Cl | CH$_3$ | C$_2$H$_5$ | CH$_3$ | H | *1.30 (d, 3 H, CH$_2$—CH$_3$) 2.30 (s, 3 H, Ar—CH$_3$) | |
| I-1-a-15 | OCH$_3$ | Cl | CH$_3$ | H | cyclopropyl | CH$_3$ | *1.11 (m, 1 H, cyclopropyl-CH) 2.30 (s, 3 H, Ar—CH$_3$) | |

**$^1$H-NMR (400 MHz, d$_6$-DMSO): δ = 2.29 (s, 3 H, ArCH$_3$), 3.83 (m, 2 H, O—CH$_2$) ppm

*$^1$H-NMR (400 MHz, d$_6$-DMSO): δ-shifts in ppm

Example No. I-1-b-1

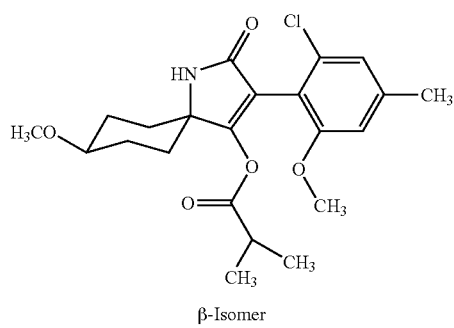

β-Isomer

Under argon, 0.7 g of the compound of Example I-1-a-3 are initially charged in 30 ml of anhydrous ethyl acetate and 0.2 g of triethylamine (2 mmol)=0.28 ml in a 100 ml three-necked flask fitted with thermometer and reflux condenser, the reaction is catalysed using 10 mg of 4-N,N-dimethylaminopyridine and, under reflux, 0.22 g (0.002 mol) of isobutyryl chloride in 2 ml of anhydrous ethyl acetate is added. The mixture is stirred for 1 hour; the reaction is monitored by thin-layer chromatography. The product is purified by silica gel column chromatography (hexane:ethyl acetate=8:2)

Yield: 0.8 g (81% of theory), m.p.: 180° C.

The following compounds of the formula (I-1-b) are obtained analogously to Example (I-1-b-1) and in accordance with the general statements on the preparation

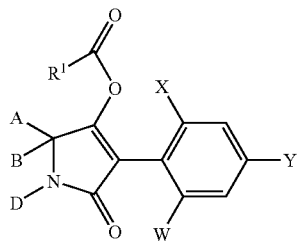

(I-1-b)

| Ex. No. | W | X | Y | D | A | B | R¹⁾ | m.p. °C. | Isomer |
|---|---|---|---|---|---|---|---|---|---|
| I-1-b-2 | OCH$_3$ | Cl | CH$_3$ | H | CH$_3$ | CH$_3$ | H$_3$CO—CH$_2$— | 191 | — |
| I-1-b-3 | OCH$_3$ | Cl | CH$_3$ | H | i-C$_4$H$_9$ | CH$_3$ | t-C$_4$H$_9$ | 154 | — |
| I-1-b-4 | OCH$_3$ | Cl | CH$_3$ | H | i-C$_4$H$_9$ | CH$_3$ | H$_3$CO—CH$_2$— | ** | — |
| I-1-b-5 | OCH$_3$ | Cl | CH$_3$ | H | —(CH$_2$)$_2$—O—(CH$_2$)$_2$— | | ▷— | 216-218 | — |
| I-1-b-6 | OCH$_3$ | Cl | CH$_3$ | H | —(CH$_2$)$_2$—O—(CH$_2$)$_2$— | | H$_3$CO—CH$_2$— | *2.30 (3 H, s, Ar—CH$_3$) 4.11 (s, 2 H, CH$_2$—O—CH$_3$) | — |
| I-1-b-7 | OCH$_3$ | Cl | CH$_3$ | H | —(CH$_2$)$_2$—CHOCH$_3$—(CH$_2$)$_2$— | | ▷— | 156-159 | β |
| I-1-b-8 | OCH$_3$ | Cl | CH$_3$ | H | —(CH$_2$)$_2$—O—(CH$_2$)$_2$— | | ClCH$_2$— | 188-207 | — |
| I-1-b-9 | OCH$_3$ | Cl | CH$_3$ | H | —(CH$_2$)$_2$—CHOCH$_3$—(CH$_2$)$_2$— | | H$_3$CO—CH$_2$— | 193-195 | — |
| I-1-b-10 | OCH$_3$ | Cl | CH$_3$ | H | —(CH$_2$)$_2$—O—(CH$_2$)$_2$— | | 2-Cl-C$_6$H$_4$—CH$_2$— | 245-247 | — |

*¹H-NMR (300 MHz, CDCl$_3$): δ-shifts in ppm

** *3.30 (s, 3 H, CH$_2$—O—CH$_3$) 4.10 (s, 2 H, CH$_2$—O—CH$_3$)

Example No. I-1-c-1

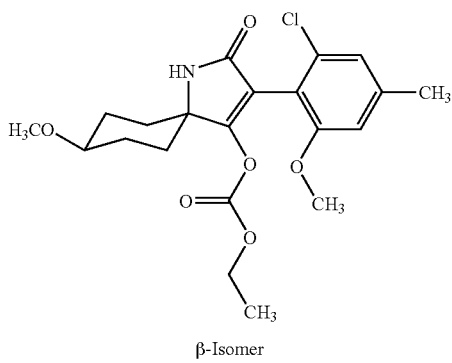

β-Isomer

Under argon 0.7 g of the compound of Example I-1-a-3 is initially charged in 30 ml of anhydrous dichloromethane and 0.2 g of triethylamine (2 mmol)=0.28 ml in a 100 ml three-necked flask fitted with thermometer and reflux condenser, and, at 20° C., 0.22 g (0.002 mol) of ethyl chloroformate in 2 ml of anhydrous dichloromethane is added. The mixture is stirred for 1 hour; the reaction is monitored by thin-layer chromatography. The product is purified by silica gel column chromatography (hexane:ethyl acetate=8:2).

Yield: 0.8 g (94% of theory), m.p.: 201° C.

The following compounds of the formula (I-1-c) are obtained analogously to Example (I-1-c-1) and in accordance with the general statements of the preparation

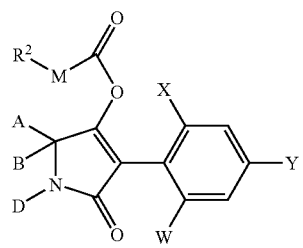

(I-1-c)

| Ex. No. | W | X | Y | D | A | B | M | $R^2$ | m.p. °C. | Isomer |
|---|---|---|---|---|---|---|---|---|---|---|
| I-1-c-2 | $OCH_3$ | Cl | $CH_3$ | H | $CH_3$ | $CH_3$ | O | $C_2H_5$ | * | — |
| I-1-c-3 | $OCH_3$ | Cl | $CH_3$ | H | i-$C_3H_7$ | $CH_3$ | O | $C_2H_5$ | +[1] | — |
| I-1-c-4 | $OCH_3$ | Cl | $CH_3$ | H | i-$C_4H_9$ | $CH_3$ | O | $C_2H_5$ | +[2] | — |
| I-1-c-5 | $OC_3H_7$ | Cl | $CH_3$ | H | —$(CH_2)_2$—$CHOCH_3$—$(CH_2)_2$— | | O | $C_2H_5$ | 195 | β |
| I-1-c-6 | $OCH_3$ | Cl | $CH_3$ | H | —$(CH_2)_2$—$CHOCH_3$—$(CH_2)_2$— | | O | $C_6H_5$—$CH_2$— | 178 | β |
| I-1-c-7 | $OCH_3$ | Cl | $CH_3$ | H | —$(CH_2)_2$—O—$(CH_2)_2$— | | O | $CH_2$=CH—$CH_2$— | 213 | — |
| I-1-c-8 | $OCH_3$ | Cl | $CH_3$ | H | —$(CH_2)_2$—O—$(CH_2)_2$— | | O | $C_6H_5$—$CH_2$— | 188-190 | — |
| I-1-c-9 | $OCH_3$ | Cl | $CH_3$ | $C_2H_5$ | $CH_3$ | H | O | $C_2H_5$ | +[3] | — |
| I-1-c-10 | $OCH_3$ | Cl | $CH_3$ | H | $C_2H_5$ | $CH_3$ | O | $C_2H_5$ | +[4] | — |

*$^1$H-NMR (400 MHz, $CDCl_3$): δ = 2.31 (s, 3 H, aryl-$CH_3$), 4.05 (q, 2 H, $CH_2O$) in ppm

**$^1$H-NMR (300 MHz, $CDCl_3$): δ-shifts in ppm

+[1]**1.15 (tr, 3 H, O—$CH_2$—$CH_3$) 4.05 (m, 2 H, O—$CH_2$—$CH_3$)

+[2]**0.90 (d, 6 H, $CH(CH_3)_2$) 3.75 (s, 3 H, Ar—O—$CH_3$)

+[3]**4.21 (ddq, 2 H, $CH_2$—O) 2.29 (s, 3 H, Ar—$CH_3$)

+[4]**2.31 (s, 3 H, Ar—$CH_3$) 4.05 (dq, 2 H, $CH_2$—O)

Example No. I-1-d-1

Example No. I-1-f-1

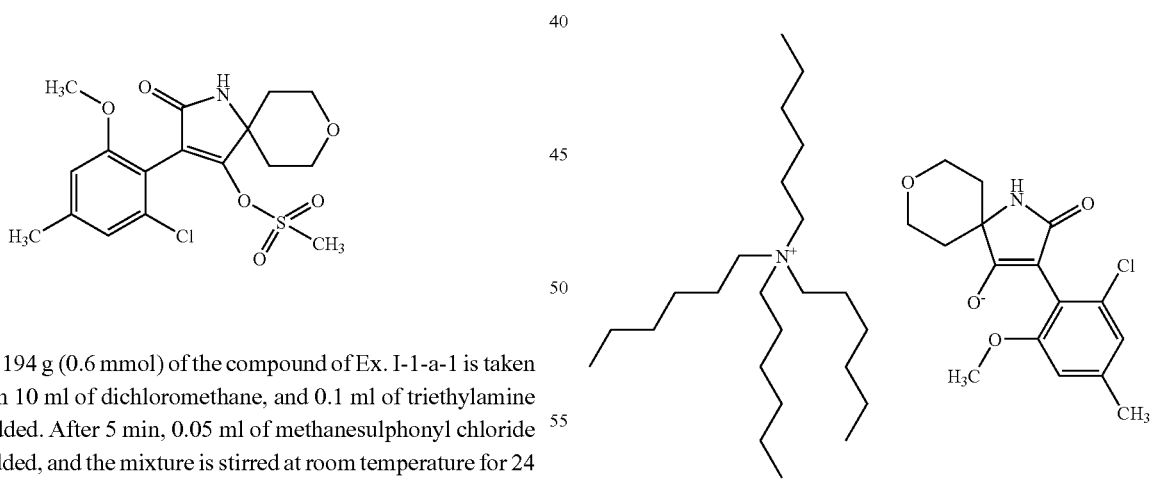

0.194 g (0.6 mmol) of the compound of Ex. I-1-a-1 is taken up in 10 ml of dichloromethane, and 0.1 ml of triethylamine is added. After 5 min, 0.05 ml of methanesulphonyl chloride is added, and the mixture is stirred at room temperature for 24 hours. 5% strength sodium bicarbonate solution is added, and the mixture is stirred for 30 min. The organic phase is separated off and dried with sodium sulphate. After evaporation to dryness, the residue is taken up in 2 ml of ethyl acetate and filtered off with suction. The filter cake is washed two more times with in each case 0.5 ml of ethyl acetate to give the desired product.

Yield: 0.105 g (44% of theory), m.p.: 221-224° C.

0.162 g (0.5 mmol) of the compounds of Ex. (I-1-a-1) is taken up in 8 ml of methanol, and, at room temperature, 0.48 ml of tetrahexylammonium hydroxide is added to this solution. The mixture is stirred at room temperature for 4 hours and then concentrated. Methanol is added to the glass-like residue obtained and distilled off, this step is repeated another three times, the residue is then taken up in dichloromethane and the solution is dried with sodium sulphate. Removal of the dichloromethane under reduced pressure gives the desired product as a glass-like substance.

Yield: 0.31 g (91% of theory)

$^1$H-NMR (300 MHz, CDCl$_3$): δ=3.01 (t broad, 8H, N—CH$_2$), 3.72 (s, 3H, OCH$_3$)

Example No. II-1

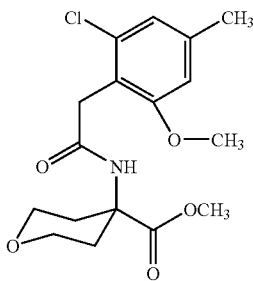

Under argon, 3.24 g (16.5 mmol) of methyl 4-aminotetrahydropyran-4-carboxylate hydrochloride are initially charged in 40 ml of anhydrous tetrahydrofuran and 4.7 ml (33 mmol) of triethylamine in a 100 ml three-necked flask fitted with thermometer and reflux condenser. The mixture is stirred for 5 min, 3.2 g of 2-chloro-6-methoxy-4-methylphenylacetic acid (15 mmol) are added and the mixture is stirred for another 15 min. 3.3 ml of triethylamine are then added, and immediately, 0.9 ml of phosphorus oxychloride is added dropwise such that the solution boils gently. The mixture is stirred under reflux for 30 min. The solvent is distilled off and the product is purified by silica gel column chromatography (dichloromethane:ethyl acetate=3:1).

Yield: 3.6 g (59% of theory), m.p.: 160° C.

Example II-8

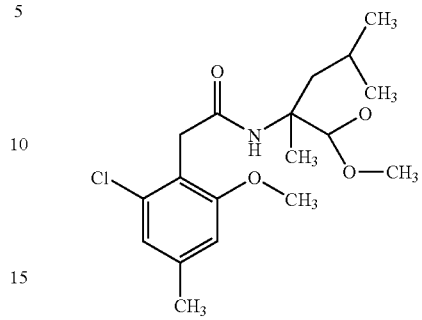

At 30-40° C., 4.8 g of the compound of Example XXIX-1 are added dropwise to 4.6 ml of concentrated sulphuric acid, and the mixture is stirred for 2 hours. After dropwise addition of 10.84 ml of methanol, the mixture is stirred at an external temperature of 40-70° C. for 5 hours and allowed to stand overnight. The reaction solution is poured into ice/H$_2$O and extracted with dichloromethane, and the extract is washed with saturated sodium bicarbonate solution, dried and concentrated using a rotary evaporator.

Yield: 3.93 g (67% of theory)

$^1$H-NMR (400 MHz, CDCl$_3$): δ=0.68, 0.80 (2d, 6H, CH$_2$—(CH$_3$)$_2$), 1.60 (dd, 2H, CH$_2$—(CH$_3$)$_2$), 3.70 (s, 2H, CH$_2$—CO), 3.85 (s, 3H, CO$_2$CH$_3$) ppm.

The following compounds of the formula (II) are obtained analogously to Example (II-1) and in accordance with the general statements on the preparation

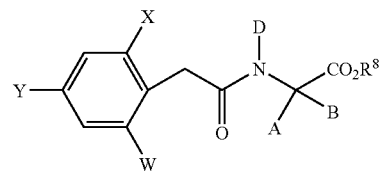

(II)

| Ex. No. | W | X | Y | D | A | B | R$^8$ | m.p. ° C. | Isomer |
|---|---|---|---|---|---|---|---|---|---|
| 11-2 | OCH$_3$ | Cl | CH$_3$ | H | CH$_3$ | CH$_3$ | CH$_3$ | 126 | — |
| 11-3 | OCH$_3$ | Cl | CH$_3$ | H | —(CH$_2$)$_2$—CHOCH$_3$—(CH$_2$)$_2$— | | CH$_3$ | 149 | β |
| 11-4 | OC$_3$H$_7$ | Cl | CH$_3$ | H | —(CH$_2$)$_2$—CHOCH$_3$—(CH$_2$)$_2$— | | CH$_3$ | 128 | β |
| 11-5 | OC$_2$H$_5$ | Cl | CH$_3$ | H | —(CH$_2$)$_2$—CHOCH$_3$—(CH$_2$)$_2$— | | CH$_3$ | 113 | β |
| 11-6 | O—CH$_2$—◁ | Cl | CH$_3$ | H | —(CH$_2$)$_2$—CHOCH$_3$—(CH$_2$)$_2$— | | CH$_3$ | 147 | β |
| 11-7 | O—(CH$_2$)—OCH$_3$ | Cl | CH$_3$ | H | —(CH$_2$)$_2$—CHOCH$_3$—(CH$_2$)$_2$— | | CH$_3$ | 112 | β |
| 11-8 | OCH$_3$ | Cl | CH$_3$ | H | —CH$_2$-i-C$_3$H$_7$ | CH$_3$ | CH$_3$ | oil | — |
| 11-9 | OCH$_3$ | Cl | CH$_3$ | H | i-C$_3$H$_7$ | CH$_3$ | CH$_3$ | *0.78, 0.85 (2 d, 6 H, CH(CH$_3$)$_2$), 3.85 (s, 3 H, CO$_2$CH$_3$) | — |
| 11-10 | OCH$_3$ | Cl | CH$_3$ | H | ◁ | CH$_3$ | CH$_3$ | 95 | — |
| 11-11 | OCH$_3$ | Cl | CH$_3$ | C$_2$H$_5$ | CH$_3$ | H | C$_2$H$_5$ | *2.29, (s, 3 H, Ar—CH$_3$), 4.11 (q, 2 H, O—CH$_2$) | |

-continued

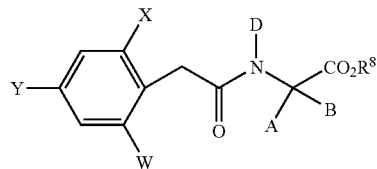

(II)

| Ex. No. | W | X | Y | D | A | B | R⁸ | m.p. °C. | Isomer |
|---|---|---|---|---|---|---|---|---|---|
| 11-12 | OCH$_3$ | Cl | CH$_3$ | H | C$_2$H$_5$ | CH$_3$ | CH$_3$ | 106-108 | — |
| 11-13 | OC$_2$H$_5$ | Cl | CH$_3$ | C$_2$H$_5$ | CH$_3$ | H | C$_2$H$_5$ | *1.46, (d, 3 H, CHCH$_3$), 2.29 (s, 3 H, Ar—CH$_3$) | |
| 11-14 | OC$_2$H$_5$ | Cl | CH$_3$ | H | △ (cyclopropyl) | CH$_3$ | CH$_3$ | 123-125 | — |
| 11-15 | OC$_2$H$_5$ | Cl | CH$_3$ | H | C$_2$H$_5$ | CH$_3$ | CH$_3$ | 85-87 | — |

* $^1$H-NMR (300 MHz, CDCl$_3$): δ-shifts in ppm

Example No. XXIX-1

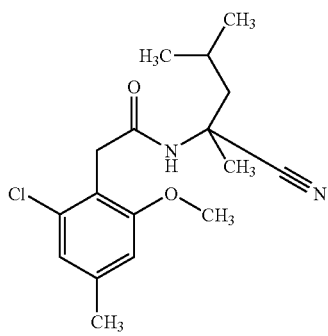

3.2 g of the compound of Example XXVII-1 and 5.44 ml of thionyl chloride are heated at 80° C. and stirred until the evolution of gas has ceased. To remove excess thionylchloride, toluene is added to the mixture and removed using a rotary evaporator, tetrahydrofuran is added and removed using a rotary evaporator and the residue is dissolved in 10 ml of tetrahydrofuran=Solution 1. At 0-10° C., Solution 1 is added dropwise to 1.88 g of 1-amino-1,4-dimethylpentanecarbonitrile in 20 ml of tetrahydrofuran and 2.48 ml of triethylamine, the reaction solution is stirred at room temperature for ~3 hours and concentrated using a rotary evaporator, the residue is dissolved in dichloromethane and the solution is washed with 0.5 M HCl, dried and concentrated using a rotary evaporator. Yield: 4.86 g (96% of theory), m.p. 131° C.

The following compounds of the formula (XXIX) are obtained analogously to Example (XXIX-1) and in accordance with the general statements of the preparation (XXIX)

(structure shown with X, Y, W on aromatic ring; —CH$_2$C(O)NH—C(A)(B)(CN))

| Ex. No. | W | X | Y | A | B | m.p. °C. |
|---|---|---|---|---|---|---|
| XXIX-2 | OCH$_3$ | Cl | CH$_3$ | i-C$_3$H$_7$ | CH$_3$ | * 0.93, 0.98 (2 d, 6 H, CH(CH$_3$)$_2$) 3.85 (s, 3 H, Ar—OCH$_3$) |
| XXIX-3 | OCH$_3$ | Cl | CH$_3$ | △ (cyclopropyl) | CH$_3$ | 132 |
| XXIX-4 | OCH$_3$ | Cl | CH$_3$ | C$_2$H$_5$ | CH$_3$ | 134-136 |
| XXIX-5 | OC$_2$H$_5$ | Cl | CH$_3$ | △ (cyclopropyl) | CH$_3$ | * 1.61, (s, 3 H, CH$_3$) 2.33 (s, 3 H, Ar—CH$_3$) |
| XXIX-6 | OC$_2$H$_5$ | Cl | CH$_3$ | C$_2$H$_5$ | CH$_3$ | * 1.73, (s, 3 H, CH$_3$) 2.32 (s, 3 H, Ar—CH$_3$) |

* $^1$-NMR (300 MHz, CDCl$_3$): δ-shifts in ppm

Example No. I-2-a-1

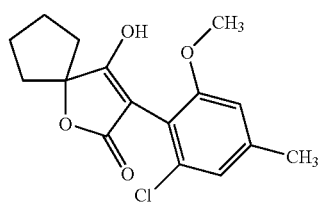

At 0-10° C., 3.9 g (11 mmol) of the compound of Example III-1, dissolved in 10 ml of dimethylformamide, are added dropwise to 1.85 g (16 mmol) of potassium tert-butoxide in 10 ml of dimethylformamide. The mixture is stirred at room temperature for 15 hours. The solvent is distilled off, the residue is stirred into water and acidified using HCl solution and the precipitate is filtered off with suction and dried.

Yield: 2.9 g (77% of theory), m.p.: 198° C.

The following compounds of the formula (I-2-a) are obtained analogously to Example (I-2-a-1) and in accordance with the general statements of the preparation

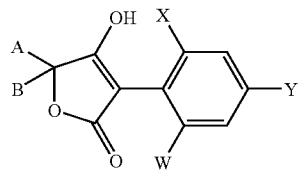
(I-2-a)

| Ex. No. | W | X | Y | A | B | m. p. ° C. |
|---|---|---|---|---|---|---|
| I-2-a-2 | OCH$_3$ | Cl | CH$_3$ | —(CH$_2$)$_2$—CHOCH$_3$—(CH$_2$)$_2$— | | 173-175 |
| I-2-a-3 | OCH$_3$ | Cl | CH$_3$ | —(CH$_2$)$_2$—O—(CH$_2$)$_2$— | | 216 |

Example No. I-2-b-1

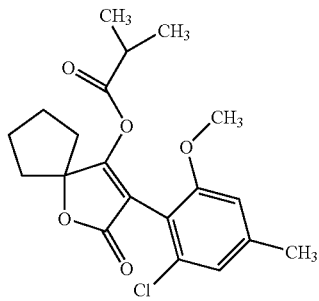

With ice cooling, 0.23 g (2.2 mmol) of isobutyryl chloride is added to 0.61 g (2 mmol) of the compound of Example I-2-a-1 in 10 ml of dichloromethane and 0.31 ml of triethylamine, and the solution is stirred overnight. The solution is washed with 10% strength citric acid and 10% strength NaOH, the phases are separated and the organic phase is dried and concentrated.

Yield: 0.85 g (oil)

$^1$H-NMR (400 MHz, CD$_3$CN): δ=2.35 (s, 3H, Ar—CH$_3$), 2.70 (m, 1H, C$\underline{H}$—(CH$_3$)$_2$), 3.75 (s, 3H, OCH$_3$) ppm.

The following compounds of the formula (I-2-b) are obtained analogously to Example (I-2-b-1) and in accordance with the general statements of the preparation

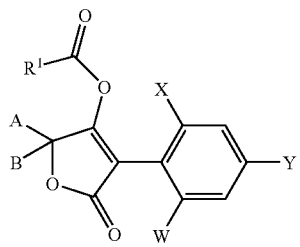
(I-2-b)

| Ex. No. | W | X | Y | A | B | m. p. ° C. |
|---|---|---|---|---|---|---|
| I-2-b-2 | OCH$_3$ | Cl | CH$_3$ | —(CH$_2$)$_2$—CHOCH$_3$—(CH$_2$)$_2$— | i-C$_3$H$_7$ | *3.30, 3.34 (2 s, 3 H, CH—OCH$_3$) 3.74, 3.75 (2 s, 3 H, Ar—OCH$_3$) |
| I-2-b-3 | OCH$_3$ | Cl | CH$_3$ | —(CH$_2$)$_2$—O—(CH$_2$)$_2$— | i-C$_3$H$_7$ | *1.07-1.19 (8 s, 6 H, CH—(CH$_3$)$_2$) 3.74, 3.76 (2 s, 3 H, Ar—OCH$_3$) |

*$^1$H-NMR (400 MHz, CD$_C$N): δ stated in ppm.

Example No. I-2-c-1

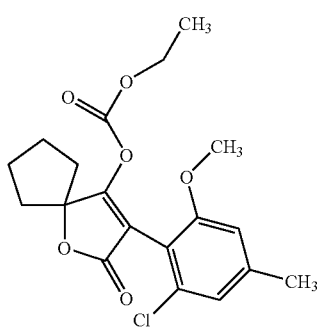

With ice cooling, 0.24 g (2.2 mmol) of ethyl chloroformate is added to 0.6 g (2 mmol) of the compound from Example I-2-a-1 in 10 ml of dichloromethane and 0.31 ml of triethylamine, and the solution is stirred at room temperature for 8 h. The solution is washed with 10% strength citric acid and 10% strength NaOH, the phases are separated and the organic phase is dried and concentrated.

Yield: 0.7 g (85% of theory)

$^{1}$H-NMR (400 MHz, CD$_3$CN): δ=1.13 (t, 3H, —O—CH$_2$CH$_3$), 4.05 (q, 2H, —O—CH$_2$CH$_3$) ppm.

The following compounds of the formula (I-2-c) are obtained analogously to Example (I-2-c-1) and in accordance with the general statements of the preparation

Example No. III-1

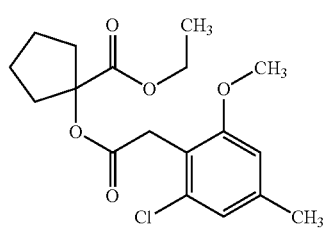

1.7 g (11 mol) of ethyl 1-hydroxycyclopentanecarboxylate and 2.6 g (11 mmol) of 2-chloro-4-methyl-6-methoxyphenylacetyl chloride are heated at 120-140° C. until the evolution of gas has ceased, and the mixture is then briefly degassed on an oil pump.

The product is used without further purification for preparing Example I-2-a-1.

Yield: 3.9 g (87% of theory)

The following compounds of the formula (III) are obtained analogously to Example (III-1) and in accordance with the general statements on the preparation

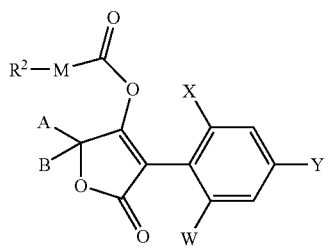

(I-2-c)

| Ex. No. | W | X | Y | A | M | R$^2$ | m. p. ° C. |
|---|---|---|---|---|---|---|---|
| I-2-c-2 | OCH$_3$ | Cl | CH$_3$ | —(CH$_2$)$_2$—CHOCH$_3$—(CH$_2$)$_2$— | O | C$_2$H$_5$ | 1.10-1.15 (6 s, 3 H, —OCH$_2$CH$_3$) 3.31, 3.32 (2 s, 3 H, CHOCH$_3$) |
| I-2-c-3 | OCH$_3$ | Cl | CH$_3$ | —(CH$_2$)$_2$—O—(CH$_2$)$_2$— | O | C$_2$H$_5$ | 3.91-3.96 (m, 2 H, —O—CH$_2$—CH$_2$) 4.05-4.07 (m, 2 H, —O—CH$_2$CH$_3$) |

* $^{1}$H-NMR (400 MHz, CD$_3$CN): δ stated in ppm.

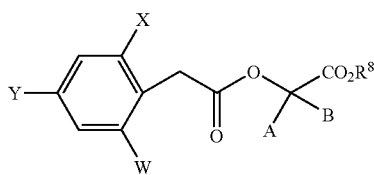

(III)

| Ex. No. | W | X | Y | A | B | R⁸ |
|---|---|---|---|---|---|---|
| III-2 | $OCH_3$ | Cl | $CH_3$ | —$(CH_2)_2$—$CHOCH_3$—$(CH_2)_2$— | | $C_2H_5$ |
| III-3 | $OCH_3$ | Cl | $CH_3$ | —$(CH_2)_2$—O—$(CH_2)_2$— | | $C_2H_5$ |

The compounds of the formula (III) were used without further purification for preparing the Examples (I-2-a).

Process R

Example (XXXI-1)

Methyl 2-chloro-4-methyl-6-methoxyphenylacetate

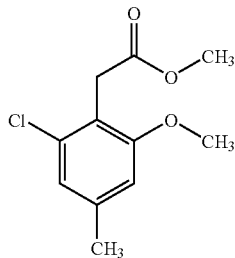

Under an atmosphere of argon, 100 g (360 mmol) of methyl 2-bromo-6-chloro-4-methylacetate, known from WO 96/35664, 10.3 g (72 mmol) of copper(I) bromide and 105 ml (1.08 ml) of methyl acetate are initially charged in 345 ml (1.80 mol) of a 30% strength sodium methoxide solution, and the mixture is heated under reflux for 12 h. After cooling of the reaction mixture, the solvent is removed under reduced pressure, the residue is taken up in 200 ml of water and 200 ml of dichloromethane are added. The phases are separated and the organic phase is washed twice with water and once with saturated sodium chloride solution. The combined organic extracts are dried over sodium sulphate, and the solvent is then removed under reduced pressure and the residue is purified by chromatography.

Yield: 75 g (91%)

¹H-NMR {400 MHz, DMSO-$d_6$}: 2.30 (s, 3H, $CH_3$); 3.60 (s, 3H $OCH_3$); 3.70 (s, 2H, $CH_2$); 3.77 (s, 3H, $OCH_3$); 6.84 (s 1H, Ph-H); 6.89 (s, 1H, Ph-H).

MS/CI: 229 (M+1).

Example (XXVII-1)

2-Chloro-4-methyl-6-methoxyphenylacetic acid

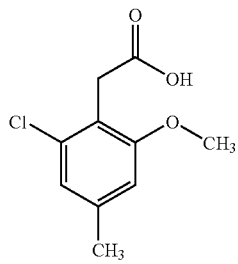

75 g (328 mmol) of methyl 2-chloro-4-methyl-6-methoxyphenylacetate according to Ex. XXXI-1 are dissolved in 750 ml of methanol and then heated at 80° C. together with 55.20 g (984 mmol) of potassium hydroxide and 250 ml of water for 12 h. The methanol is removed using a rotary evaporator, the residue is adjusted to pH 3 and the precipitated product is filtered off and dried.

Yield: 63.2 g (90%)

¹H-NMR {400 MHz, DMSO-$d_6$}: 2.30 (s, 3H, $CH_3$); 3.61 (s, 2H $CH_2$); 3.77 (s, 3H, $OCH_3$); 6.80 (s, 1H, Ph-H); 6.88 (s, 1H, Ph-H); 12.2 (s, 1H, $CO_2H$).

MS/CI: 215 (M+1).

Example (XXXI-2)

Ethyl 2-chloro-4-methyl-6-ethoxyphenylacetate

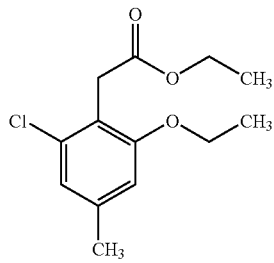

¹H-NMR {400 MHz, DMSO-$d_6$}: 1.18 (t, ³$J_{HH}$=7 Hz, 3H, $CH_3$); 1.26 (t, ³$J_{HH}$=7 Hz, 3H, $CH_3$); 2.28 (s, 3H, Ph-$CH_3$); 3.67 (s, 2H, $CH_2$); 4.02 (d, ³$J_{HH}$=7 Hz, 2H, $OCH_2$); 4.07 (d, ³$J_{HH}$=7 Hz, 2H, $OCH_2$), 6.81 (s, 1H Ph-H); 6.87 (s, 1H, Ph-H).

MS/CI: 257 (M+1).

Example (XXVII-2)

2-Chloro-4-methyl-6-ethoxyphenylacetic acid

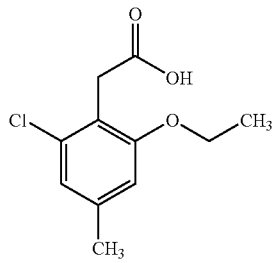

$^1$H-NMR {400 MHz, DMSO-d$_6$}: 1.27 (t, $^3$J$_{HH}$=7 Hz, 3H, CH$_3$); 2.27 (s, 3H, Ph-CH$_3$); 3.10 (s, 2H, CH$_2$); 4.02 (d, $^3$J$_{HH}$=7 Hz, 2H, OCH$_2$); 6.76 (s, 1H, Ph-H), 6.83 (s, 1H Ph-H); 12.3 (s, 1H, CO$_2$H).
MS/CI: 229 (M+1).

Example (XXXI-3)

Propyl 2-chloro-4-methyl-6-propoxyphenylacetate

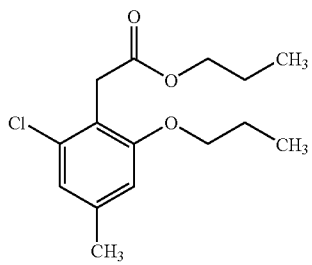

$^1$H-NMR {400 MHz, DMSO-d$_6$}: 0.88 (t, $^3$J$_{HH}$=7 Hz, 3H, CH$_3$); 0.95 (t, $^3$J$_{HH}$=7 Hz, 3H, CH$_3$); 1.54 (sext, $^3$J$_{HH}$=7 Hz, 2H, CH$_2$); 1.68 (sext, $^3$J$_{HH}$=7 Hz, 2H, CH$_2$); 2.28 (s, 3H, Ph-CH$_3$); 3.69 (s, 2H, CH$_2$); 3.92 (t, $^3$J$_{HH}$=7 Hz, 2H, OCH$_2$), 3.97 (t, $^3$J$_{HH}$=7 Hz, 2H, OCH$_2$); 6.80 (s, 1H, Ph-H); 6.86 (s, 1H, Ph-H).
MS/CI: 285 (M+1).

Example (XXVII-3)

2-Chloro-4-methyl-6-propoxyphenylacetic acid

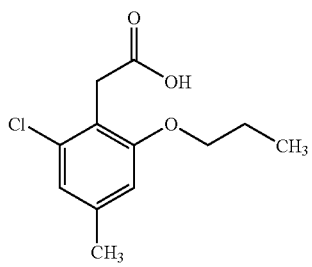

$^1$H-NMR {400 MHz, DMSO-d$_6$}: 0.95 (t, $^3$J$_{HH}$=7 Hz, 3H, CH$_3$); 1.71 (sext, $^3$J$_{HH}$=7 Hz, 2H, CH$_2$); 2.23 (s, 3H, Ph-CH$_3$); 3.61 (s, 2H, CH$_2$); 3.92 (t, $^3$J$_{HH}$=7 Hz, 2H, OCH$_2$), 6.79 (s, 1H, Ph-H); 6.85 (s, 1H, Ph-H); 12.2 (s, 1H, CO$_2$H).
MS/CI: 243 (M+1), m.p.: 116° C.

Example (XXXI-4)

Methoxyethyl 2-chloro-4-methyl-6-methoxyethoxyphenylacetate

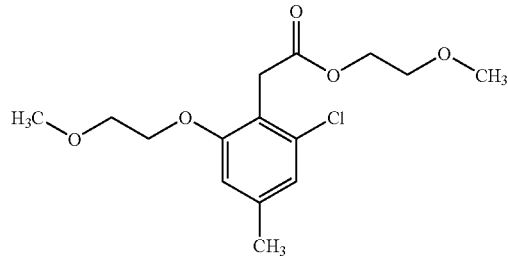

LC-MS: (ESI pos) M=317 (100)
$^1$H-NMR {400 MHz, DMSO-d$_6$}: 6.89 (s, 1H); 6.84 (s, 1H); 4.14 (m, 2H); 4.09 (m, 2H); 3.71 (s, 2H); 3.62 (m, 2H); 3.51 (m, 2H); 3.30 (s, 3H); 3.25 (s, 3H); 2.28 (s, 3H)

Example (XXVII-4)

2-Chloro-4-methyl-6-methoxyethoxyphenylacetic acid

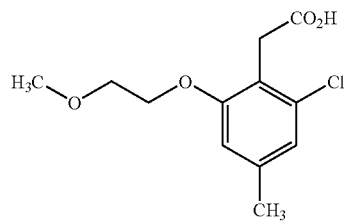

LC-MS: (ESI pos) M=258 (100)
$^1$H-NMR {400 MHz, DMSO-d$_6$}: 12.16 (s, 1H); 6.87 (s, 1H); 6.83 (s, 1H); 4.10 (m, 2H); 3.63 (m, 3H); 3.62 (s, 2H); 3.31 (s, 3H); 2.28 (s, 3H).

Example (XXXI-5)

Methyl 2-chloro-4-methyl-6-cyclopropylmethoxyphenylacetate

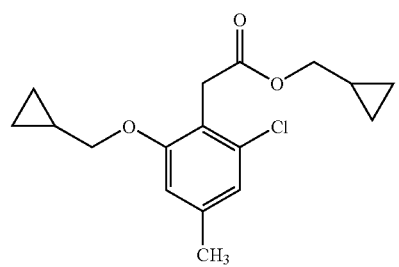

LC-MS: (ESI pos) M=309 (100)

Example (XXVII-5)

2-Chloro-4-methyl-6-cyclopropylmethoxyphenylacetic acid

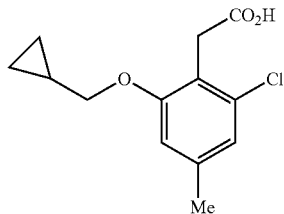

LC-MS: (ESI pos) M=255 (100)

$^1$H-NMR {400 MHz, DMSO-$d_6$}: 12.2 (s, 1H); 6.85 (s, 1H); 6.78 (s, 1H); 3.85 (d. J=6.7 Hz, 2H); 3.63 (s, 2H); 2.27 (s, 3H); 1.19 (m, 1H); 0.53 (m, 2H); 0.31 (m, 2H).

Example A

| *Aphis gossypii* Test | |
|---|---|
| Solvent: | 7 parts by weight of dimethylformamide |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

At active compound concentrations of 100 ppm, the active compounds Ex. I-2-a-1, Ex. I-2-c-3 and Ex. I-2-b-3 exhibit a kill rate against *Aphis gossypii* of ≧80% after 6 d.

Example B

| *Meloidogyne* Test | |
|---|---|
| Solvent: | 80 parts by weight of acetone |

To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action is determined in % by gall formation. 100% means that no galls were found; 0% means that the number of galls on the treated plants corresponds to that of the untreated control.

At active compound concentrations of 20 ppm, the active compounds Ex. I-1-a-3 and Ex. I-1-a-1 exhibit a kill rate against *Meloidogyne* of 100% after 14 d.

Example C

| *Myzus* Test (spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

At active compound concentrations of 500 g/ha, the active compounds Ex. I-2-a-1, Ex. I-2-a-2, Ex. I-2-c-1, Ex. I-2-b-1, Ex. I-2-c-2, Ex. I-2-c-3, Ex. I-2-b-3 and Ex. I-1-a-3 exhibit a kill rate against *Myzus persicae* of 100% after 5 d.

Example D

| *Phaedon* Test (spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of Chinese cabbage (*Brassica pekinensis*) are sprayed with a preparation of active compound of the desired concentration and, after drying, populated with larvae of the mustard beetle (*Phaedon cochleariae*).

After the desired period of time, the effect in % is determined. 100% means that all beetle larvae have been killed; 0% means that none of the beetle larvae have been killed.

At active compound concentrations of 500 g/ha, the active compounds Ex. I-2-c-2, Ex. I-2-b-2, Ex. I-1-a-3 and Ex. I-1-a-1 exhibit a kill rate against *Phaedon cochleariae* of ≧80% after 7 d.

Example E

| *Tetranychus* Test (OP resistant/spray treatment) | |
|---|---|
| Solvents: | 78 parts by weight of acetone |
| | 1.5 parts by weight of dimethylformamide |
| Emulsifier: | 0.5 part by weight of alkylaryl polyglycol ether |

To produce a suitable preparation of active compound, 1 part by weight of active compound is mixed with the stated amounts of solvents and emulsifier, and the concentrate is diluted with emulsifier-containing water to the desired concentration.

Discs of bean leaves (*Phaseolus vulgaris*) which are infested by all stages of the greenhouse red spider mite (*Tetranychus urticae*) are sprayed with a preparation of active compound having the desired concentration.

After the desired period of time, the effect in % is determined. 100% means that all spider mites have been killed; 0% means that none of the spider mites have been killed.

At active compound concentrations of 100 g/ha, the active compounds Ex. I-2-a-2, Ex. I-2-b-1, Ex. I-2-c-2, Ex. I-2-b-2, Ex. I-2-c-3, Ex. I-1-a-2 and Ex. I-1-a-3 exhibit a kill rate against *Tetranychus urticae* of ≧80% after 5 d.

Example F

1. Herbicidal Pre-emergence Action

Seeds of monocotyledonous and dicotyledonous weed and crop plants are placed into sandy loam in wood fibre pots and covered with soil. The test compounds, formulated in the form of wettable powders (WP), are then, in various dosages as aqueous suspension with a water application rate of 600 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with untreated controls (herbicidal effect in percent (%): 100% effect=the plants have died, 0% effect=like control plants).

2. Herbicidal Post-emergence Action

Seeds of monocotyledonous and dicotyledonous weed and crop plants are placed into sandy loam in wood fibre pots, covered with soil and cultivated in a greenhouse under good growth conditions. 2-3 weeks after sowing, the test plants are treated at the one-leaf stage. The test compounds, formulated as wettable powders (WP), are, in various dosages with a water application rate of 600 l/ha (converted), with 0.2% of wetting agent added, sprayed onto the green parts of the plants. After the test plants were kept in the greenhouse under optimum growth conditions for about 3 weeks, the effect of the preparations is rated visually in comparison to untreated controls (herbicidal effect in percent (%): 100% effect=the plants have died, 0% effect=like control plants).

At active compound concentrations of 320 g of a.i./ha, the active compound I-1-a-2, applied by the pre-emergence method, shows a kill rate of ≧80% against *Lolium* and *Setaria*.

At active compound concentrations of 320 g of a.i./ha, the active compounds Ex. I-2-a-2, Ex. I-2-c-2, Ex. I-2-b-2, Ex. I-2-b-1, Ex. I-1-a-2, Ex. I-1-a-3, Ex. I-1-b-2, Ex. I-2-a-3, Ex. I-1-a-1, Ex. I-1-c-2, applied by the post-emergence method, show a kill rate of ≧70% against *Avena sativa*, *Lolium* and *Setaria*.

Example G

Herbicidal Action and Safener Action, Pre-emergence or Post-emergence

Seeds of rhizome pieces of monocotyledonous and dicotyledonous harmful plants and of crop plants are placed into sandy loam in pots made of peat, covered with soil and cultivated in a greenhouse under growth conditions. In the pre-emergence application, safener and herbicide are applied after sowing, the post-emergence treatment is carried out about two to three weeks after sowing, at the three-leaf stage of the test plants. The herbicide/safener active compound combinations according to the invention, formulated as emulsion concentrates, and in parallel experiments the correspondingly formulated individual active compounds are, at various dosages at a water application rate of 300 l/ha (converted), sprayed onto the surface of the soil when applied by the pre-emergence method and onto the green parts of the plants when applied by the post-emergence method. Pre-emergence evaluation is carried out after 2-4 weeks, post-emergence evaluation is carried out after 1-3 weeks. During this time, the test plants are kept in a greenhouse under optimum growth conditions. The effect of the preparation is scored visually in comparison to untreated controls.

Container trials with cereal in the greenhouse.

Safener and herbicide were applied successively to the plants by the post-emergence method (application rates: see Tables)

TABLE 1'

| | Application rate g of a.i./ha | Summer barley observed (%) |
|---|---|---|
| Example I-1-c-1 | 100 | 60 |
| | 50 | 30 |
| | 25 | 10 |
| Example I-1-c-1 + mefenpyr | 100 + 100 | 50 |
| | 50 + 100 | 10 |
| | 25 + 100 | 0 |
| Example I-1-c-1 + isoxadifen | 100 + 100 | 40 |
| | 50 + 100 | 15 |
| | 25 + 100 | 0 |

TABLE 2'

| | Application rate g of a.i./ha | Winter wheat observed (%) |
|---|---|---|
| Example I-1-c-1 | 50 | 30 |
| | 25 | 10 |
| Example I-1-c-1 + cloquintocet | 50 + 100 | 20 |
| | 25 + 100 | 0 |
| Example I-1-c-1 + isoxadifen | 50 + 100 | 20 |
| | 25 + 100 | 0 |

TABLE 3'

| | Application rate g of a.i./ha | Summer wheat (%) | Winter wheat (%) | Summer barley (%) |
|---|---|---|---|---|
| Example I-1-a-5 | 100 | 60 | 60 | 20 |
| | 50 | 50 | 30 | 20 |
| | 25 | 20 | 10 | 10 |
| Example I-1-a-5 + mefenpyr | 100 + 100 | 50 | 30 | 10 |
| | 50 + 100 | 20 | 10 | 0 |
| | 25 + 100 | 10 | 0 | 0 |

TABLE 4'

| | Application rate g of a.i./ha | Winter wheat (%) | Summer barley (%) |
|---|---|---|---|
| Example I-1-a-5 | 100 | 60 | 20 |
| | 50 | 30 | 20 |
| | 25 | 10 | 10 |
| Example I-1-a-5 + cloquintocet | 100 + 100 | 30 | 20 |
| | 50 + 100 | 10 | 0 |
| | 25 + 100 | 0 | 0 |
| Example I-1-a-5 + isoxadifen | 50 + 100 | 20 | 10 |
| | 25 + 100 | 10 | 0 |

TABLE 5'

|  | Application rate g of a.i./ha | Summer barley (%) |
|---|---|---|
| Example I-1-b-1 | 100 | 55 |
|  | 50 | 40 |
|  | 25 | 30 |
| Example I-1-b-1 + mefenpyr | 100 + 100 | 30 |
|  | 50 + 100 | 10 |
|  | 25 + 100 | 0 |
| Example I-1-b-1 + cloquintocet | 100 + 100 | 40 |
|  | 50 + 100 | 20 |
|  | 25 + 100 | 10 |
| Example I-1-b-1 + isoxadifen | 100 + 100 | 50 |
|  | 50 + 100 | 25 |
|  | 25 + 100 | 10 |

TABLE 6'

|  | Application rate g of a.i./ha | Summer wheat (%) | Winter wheat (%) | Summer barley (%) |
|---|---|---|---|---|
| Example I-1-a-4 | 100 | 60 | 50 | 20 |
|  | 50 | 45 | 30 | 10 |
|  | 25 | 20 | 10 | 0 |
| Example I-1-a-4 + mefenpyr | 100 + 100 | 10 | 10 | 0 |
|  | 50 + 100 | 0 | 0 | 0 |
|  | 25 + 100 | 0 | 0 | 0 |
| Example I-1-a-4 + cloquintocet | 100 + 100 | 10 | 10 | 10 |
|  | 50 + 100 | 5 | 0 | 0 |
|  | 25 + 100 | 0 | 0 | 0 |

Safener and herbicide applied successively by the pre-emergence method.

TABLE 7'

|  | Application rate g of a.i./ha | Maize (%) |
|---|---|---|
| Example I-1-a-4 | 50 | 20 |
|  | 25 | 10 |
| Example I-1-a-4 + IIe-5 | 50 + 100 | 5 |
|  | 25 + 100 | 5 |

Example H

Safener Action after Seed Dressing

The number of crop plant seeds needed for each safener application rate was calculated. Based on the weight of 100 seeds, sufficient seeds were weighed into screw top glass bottles approximately twice the volume of the seeds.

The prospective safeners were formulated as wettable powders or water-dispersible granules. These formulations were weighed out so that the required application rates (g of a.i./kg of seed) were obtained. The samples were added to the seeds in the bottles, followed by sufficient water to produce a seed dressing. The bottles were closed and then placed in an overhead shaker (set at medium speed for a period of up to one hour) so that the seeds were evenly coated with the seed dressing. The bottles were opened and the seeds were used in the pre-emergence tests.

Pre-emergence Application of Herbicides

The safener-treated seeds and untreated seeds as controls were sown in a sandy loam soil in round pots having a diameter of 7 to 13 cm and covered with approximately 0.5 to 1 cm of a 1:1 mix of sandy loam soil and sand. The herbicides, as liquid (for example emulsifiable concentrates) or dry (for example wettable powders) formulations, were diluted to the required concentrations using deionized water and applied to the soil surface using a track sprayer calibrated to deliver 300 liters of spray solution per hectare.

The pots were placed under good growing conditions in a greenhouse, and a visual assessment of the herbicidal effects was made 3 to 4 weeks after the application of the herbicide. The assessment was on a percentage basis in comparison to untreated control plants (0%=no damage, 100%=complete kill).

Herbicide application by the pre-emergence method, safener-dressed:

TABLE 8'

|  | Application rate g of a.i./ha | Maize (%) |
|---|---|---|
| Example I-1-c-1 | 25 | 35 |
| Example I-1-c-1 + IIe-5 | 25 0.5 g/kg seed | 15 |

TABLE 9'

|  | Application rate g of a.i./ha | Maize (%) |
|---|---|---|
| Example I-1-a-5 | 50 | 20 |
|  | 25 | 20 |
| Example I-1-a-5 + IIe-5 | 50 + 0.5 g/kg seed | 10 |
|  | 25 + 0.5 g/kg seed | 5 |

TABLE 10'

|  | Application rate g of a.i./ha | Maize (%) |
|---|---|---|
| Example I-1-a-4 | 50 | 20 |
|  | 25 | 10 |
| Example I-1-a-4 + IIe-5 | 50 + 0.5 g/kg seed | 15 |
|  | 25 + 0.5 g/kg seed | 0 |

Example I

| Critical concentration test/soil insects - treatment of transgenic plants | |
|---|---|
| Test insect: | *Diabrotica balteata* - larvae in soil |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the appropriate test insects are placed into the treated soil. After a further 7 days, the efficacy of the active compound is determined by counting the maize plants that have emerged (1 plant=20% activity).

Example J

| Heliothis virescens Test - treatment of transgenic plants | |
|---|---|
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp., USA) are treated by being dipped into the preparation of active compound of the desired concentration and are populated with the tobacco bud worm *Heliothis virescens* while the leaves are still moist.

After the desired period of time, the kill of the insects is determined.

The invention claimed is:

1. A compound of formula (I)

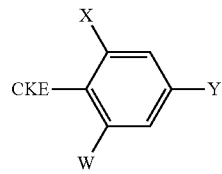

in which

W represents methoxy, ethoxy, n-propoxy, methoxyethoxy or cyclopropylmethoxy,
X represents chlorine,
Y represents methyl,
CKE represents the group

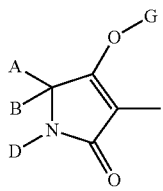

A represents methyl, ethyl, isopropyl, isobutyl or cyclopropyl,
B represents hydrogen, methyl or ethyl, or
A, B and the carbon atom to which they are attached represent saturated $C_5$-$C_6$-cycloalkyl in which optionally one ring atom is replaced by oxygen and which is optionally monosubstituted by methyl or methoxy,
D represents hydrogen, methyl or ethyl,
G represents hydrogen (a) or represents one of the groups

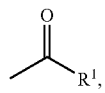

(b)

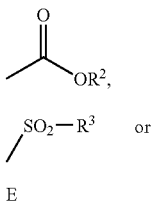

(c)

(d)

(f)

E represents an ammonium ion,
$R^1$ represents $C_1$-$C_6$-alkyl, $C_1$-$C_2$-alkoxy-$C_1$-alkyl, $C_3$-$C_6$-cycloalkyl, $C_1$-$C_4$-alkyl which is monosubstituted by chlorine or represents phenyl which is optionally monosubstituted by chlorine,
$R^2$ represents $C_1$-$C_8$-alkyl, $C_3$-$C_6$-alkenyl or benzyl,
$R^3$ represents $C_1$-$C_6$-alkyl.

2. A process for preparing a compound of the formula (I) according to claim 1, comprising
(A) obtaining a compound of the formula (I-1-a)

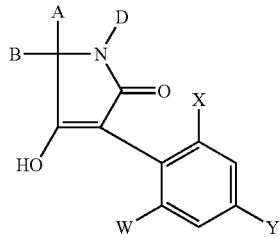

in which
A, B, D, W, X and Y are as defined in claim 1, by the intramolecular condensation of a compound of the formula (II)

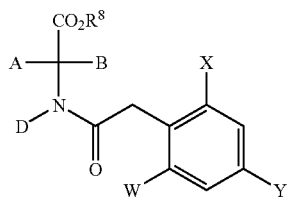

in which
A, B, D, W, X and Y are as defined in claim 1,
and
$R^8$ represents alkyl,
in the presence of a diluent and in the presence of a base,
(I) obtaining a compound of the formula (I-1-b)

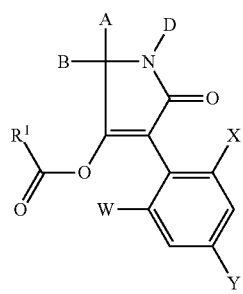

in which A, B, D, R¹, W, X and Y are as defined in claim 1, by the reaction of a compound of the formula (I-1-a) in which A, B, D, W, X and Y are as defined in claim 1

(a) is reacted with an acid halide of the formula (XIII)

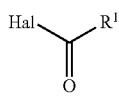
(XIII)

in which
R¹ is as defined in claim 1 and
Hal represents halogen,
or
(b) with a carboxylic anhydride of the formula (XIV)

(XIV)

in which
R¹ is as defined in claim 1,
optionally in the presence of a diluent and optionally in the presence of an acid binder,
(J) obtaining a compound of the formula (I-1-c)

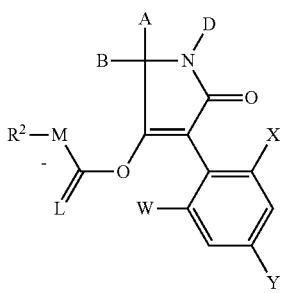

in which A, B, D, R², W, X and Y are as defined in claim 1, M represents oxygen, and L represents oxygen, by the reaction of a compound of the formula (I-1-a) in which A, B, D, W, X and Y are as defined in claim 1 with a chloroformic ester of the formula (XV)

(XV)

in which
R² is as defined in claim 1, and M is defined above, optionally in the presence of a diluent and optionally in the presence of an acid binder,
(L) obtaining a compound of the formula (I-1-d)

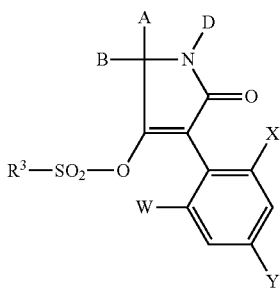

in which A, B, D, R³, W, X and Y are as defined in claim 1, by the reaction of a compound of the formula (I-1-a) in which A, B, D, W, X and Y are as defined above, with a sulphonyl chloride of the formula (XVII)

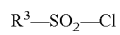
(XVII)

in which
R³ is as defined in claim 1,
optionally in the presence of a diluent and optionally in the presence of an acid binder,
(N) obtaining a compound of the formula (I-1-f)

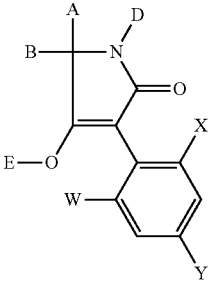

in which A, B, D, E, W, X and Y are as defined in claim 1, by the reaction of a compound of the formula (I-1-a) in which A, B, D, W, X and Y are as defined in claim 1 with an amine of the formula (XX),

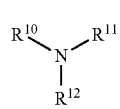
(XX)

in which
R¹⁰, R¹¹, R12 independently of one another represent hydrogen or alkyl, optionally in the presence of a diluent,
(P) obtaining a compound of the formula (I-1-a) in which A, B, D, W, X and Y are as defined above, by the reaction of a compound of the formula (I-1-a') in which A, B, D, X and Y are as defined above and W' represents bromine

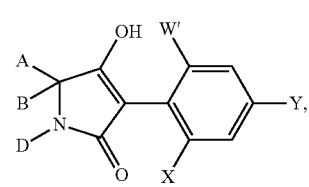
(I-1-a')

with an alcohol of the formula

in which
W is as defined in claim 1, optionally in the presence of a solvent, a Cu(I) salt and a strong base.

3. A pesticide or herbicide comprising at least one compound of the formula (I) according to claim 1.

4. A method for controlling animal pests or unwanted vegetation comprising contacting a compound of the formula (I) according to claim 1 with the pests or their habitat.

5. A process for preparing pesticides or herbicides comprising mixing at least one compound of the formula (I) according to claim 1 with an extender or a surfactant or a combination thereof.

* * * * *